US011633341B2

(12) United States Patent
Schauer et al.

(10) Patent No.: US 11,633,341 B2
(45) Date of Patent: Apr. 25, 2023

(54) DENTAL VARNISHES THAT RELEASE SPECIFICALLY TARGETED ANTIMICROBIAL PEPTIDES AND/OR FLUORIDE

(71) Applicant: C3 Jian, LLC, Marina Del Rey, CA (US)

(72) Inventors: Evan Schauer, Los Angeles, CA (US); Miroslav Baudys, Marina Del Rey, CA (US); Brian C. Varnum, Santa Monica, CA (US); Christopher W. Kaplan, Los Angeles, CA (US); Randal H. Eckert, Ellensburg, WA (US); Jay Turetzky, Downey, CA (US); Angela Soriaga, Culver City, CA (US)

(73) Assignee: C3 Jian, LLC, Marina Del Rev, CA (US)

( * ) Notice: Subject to any disclaimer, the term of this patent is extended or adjusted under 35 U.S.C. 154(b) by 171 days.

(21) Appl. No.: 16/604,130

(22) PCT Filed: Apr. 12, 2018

(86) PCT No.: PCT/US2018/027350
§ 371 (c)(1),
(2) Date: Oct. 9, 2019

(87) PCT Pub. No.: WO2018/191529
PCT Pub. Date: Oct. 18, 2018

(65) Prior Publication Data
US 2020/0276103 A1   Sep. 3, 2020

Related U.S. Application Data

(60) Provisional application No. 62/485,787, filed on Apr. 14, 2017.

(51) Int. Cl.
*A61K 8/64* (2006.01)
*A61K 8/21* (2006.01)
*A61Q 11/00* (2006.01)

(52) U.S. Cl.
CPC .............. *A61K 8/64* (2013.01); *A61K 8/21* (2013.01); *A61Q 11/00* (2013.01); *A61K 2800/87* (2013.01)

(58) Field of Classification Search
CPC ... A61K 8/49; A61K 8/41; A61K 6/20; A61K 6/69; A61Q 11/00
USPC .......................................................... 424/49
See application file for complete search history.

(56) References Cited

U.S. PATENT DOCUMENTS

| 3,497,591 A | 2/1970 | Yankell et al. |
| 5,330,746 A * | 7/1994 | Friedman ................ A61K 6/65 424/49 |
| 7,128,899 B2 | 10/2006 | Chen |
| 7,846,895 B2 | 12/2010 | Eckert et al. |
| 8,680,058 B2 | 3/2014 | Eckert et al. |
| 9,351,490 B2 | 5/2016 | Eckert et al. |
| 10,111,926 B2 | 10/2018 | Eckert et al. |
| 2002/0176827 A1 | 11/2002 | Rajaiah et al. |
| 2005/0113510 A1 | 5/2005 | Feldstein et al. |
| 2005/0175552 A1 | 8/2005 | Hoic et al. |
| 2007/0003493 A1 | 1/2007 | Simonton et al. |
| 2009/0191279 A1 | 7/2009 | Kennard et al. |
| 2011/0039763 A1 | 2/2011 | Eckert et al. |
| 2011/0244430 A1 | 10/2011 | Gibson et al. |
| 2012/0039820 A1 | 2/2012 | Wagner-doebler et al. |
| 2014/0051036 A1 | 2/2014 | Wagner-doebler et al. |
| 2014/0162208 A1 | 6/2014 | Stookey et al. |
| 2014/0248222 A1 | 9/2014 | Huo et al. |
| 2014/0349917 A1 | 11/2014 | Eckert et al. |
| 2015/0257983 A1 * | 9/2015 | Lendenmann ........... A61K 6/20 424/78.02 |

(Continued)

FOREIGN PATENT DOCUMENTS

| WO | WO 2005/082407 A1 | 9/2005 |
| WO | WO 2008/030988 A2 | 3/2008 |

(Continued)

OTHER PUBLICATIONS

Eudragit® E 100, Eudragit® E PO and Eudragit® E 12,5 Technical Information (Jul. 2015) Evonik Nutrition & Care GmbH Info 7.1/E [6 pages].
U.S. Final Office Action dated Mar. 3, 2022 issued in U.S. Appl. No. 16/604,135.
PCT International Search Report and Written Opinion dated Jul. 26, 2018 issued in PCT/US2018/027350.
PCT International Preliminary Report on Patentability dated Oct. 15, 2019 issued in PCT/US2018/027350.
PCT International Search Report and Written Opinion dated Jul. 6, 2018 issued in PCT/US2018/027357.

(Continued)

*Primary Examiner* — Walter E Webb
(74) *Attorney, Agent, or Firm* — Tom Hunter; Weaver Austin Villeneuve & Sampson LLP

(57) ABSTRACT

In various embodiments a dental varnish system having improved peptide release and fluoride release properties is provided. In various embodiments a dental varnish system that provides release of an antimicrobial peptide, or specifically targeted antimicrobial peptide (STAMP), e.g., the peptide C16G2, is provided, with or without a fluoride. In various embodiments, a dental varnish system that provides release of a fluoride, with or without an antimicrobial peptide or STAMP is provided. In certain embodiments the dental varnish system comprises a first component that is a dry powder, said first component comprising a an antimicrobial peptide, with or without a fluoride, and a bulking agent, and a second component that is a fluid, said second component comprising a varnish solution, where combination of said first component with said second component provides a varnish formulation for application to the surface of a tooth.

15 Claims, 6 Drawing Sheets
Specification includes a Sequence Listing.

(56) References Cited

U.S. PATENT DOCUMENTS

| | | | |
|---|---|---|---|
| 2016/0031941 A1* | 2/2016 | Eckert | A61P 31/00 424/54 |
| 2016/0303007 A1 | 10/2016 | Blanvalet et al. | |
| 2016/0368953 A1 | 12/2016 | Renye, Jr. et al. | |
| 2017/0027168 A1 | 2/2017 | Heath | |
| 2017/0135922 A1* | 5/2017 | Yang | A61K 8/24 |
| 2020/0113818 A1 | 4/2020 | Schauer et al. | |

FOREIGN PATENT DOCUMENTS

| | | |
|---|---|---|
| WO | WO 2010/091199 A2 | 8/2010 |
| WO | WO 2018/191533 A1 | 10/2018 |

OTHER PUBLICATIONS

PCT International Preliminary Report on Patentability dated Oct. 15, 2019 issued in PCT/US2018/027357.

U.S. Office Action dated May 25, 2021 issued in U.S. Appl. No. 16/604,135.

Eckert et al. (2006) "Targeted Killing of *Streptococcus mutans* by a Pheremone-Guided "Smart" Antimicrobial Peptide" *Antimicrobial Agents and Chemotherapy* 50(11): 3651-3657.

Mai et al. (2011) "A Novel Target-Specific, Salt-Resistant Antimicrobial Peptide against the Cariogenic Pathogen *Streptococcus mutans*" *Antimicrobial Agentsand Chemotherapy* 55(11): 5205-5213.

Rogy et al. (2017) "A Phase 2 Study to Evaluate the Microbiology, Safety and Tolerability of C16G2 Dental Strip" ClinicalTrials.gov Study NCT03052842 [5 pages].

Wei et al. (2006) "Effect of MUC7 peptides on the growth of bacteria and on *Streptococcus mutans* biofilm" *J Antimicrobial Chemotherapy* 57: 1100-1109.

U.S. Non-Final office Action dated Oct. 6, 2022 in U.S. Appl. No. 16/604,135.

\* cited by examiner

```
                       SEQUENCE LISTING

<160> NUMBER OF SEQ ID NOS: 330

<210> SEQ ID NO 1
<211> LENGTH: 35
<212> TYPE: PRT
<213> ORGANISM: Artificial
<220> FEATURE:
<223> OTHER INFORMATION: Synthetic peptide

<400> SEQUENCE: 1

Thr Phe Phe Arg Leu Phe Asn Arg Ser Phe Thr Gln Ala Leu Gly Lys
1               5                   10                  15

Gly Gly Gly Lys Asn Leu Arg Ile Ile Arg Lys Gly Ile His Ile Ile
            20                  25                  30

Lys Lys Tyr
        35

<210> SEQ ID NO 2
<211> LENGTH: 35
<212> TYPE: PRT
<213> ORGANISM: Artificial
<220> FEATURE:
<223> OTHER INFORMATION: Synthetic peptide

<400> SEQUENCE: 2

Thr Phe Phe Arg Leu Phe Asn Arg Ser Phe Thr Gln Ala Leu Gly Lys
1               5                   10                  15

Gly Gly Gly Lys Asn Leu Arg Ile Ile Arg Lys Gly Ile His Ile Ile
            20                  25                  30

Lys Lys Tyr
        35

<210> SEQ ID NO 3
<211> LENGTH: 16
<212> TYPE: PRT
<213> ORGANISM: Artificial
<220> FEATURE:
<223> OTHER INFORMATION: Synthetic peptide

<400> SEQUENCE: 3

Thr Phe Phe Arg Leu Phe Asn Arg Ser Phe Thr Gln Ala Leu Gly Lys
1               5                   10                  15

<210> SEQ ID NO 4
<211> LENGTH: 16
<212> TYPE: PRT
<213> ORGANISM: Artificial
<220> FEATURE:
<223> OTHER INFORMATION: Synthetic peptide

<400> SEQUENCE: 4
```

Lys Asn Leu Arg Ile Ile Arg Lys Gly Ile His Ile Ile Lys Lys Tyr
1               5                   10                  15

<210> SEQ ID NO 5
<211> LENGTH: 21
<212> TYPE: PRT
<213> ORGANISM: Artificial
<220> FEATURE:
<223> OTHER INFORMATION: Synthetic peptide

<400> SEQUENCE: 5

Ser Gly Ser Leu Ser Thr Phe Phe Arg Leu Phe Asn Arg Ser Phe Thr
1               5                   10                  15

Gln Ala Leu Gly Lys
            20

<210> SEQ ID NO 6
<211> LENGTH: 17
<212> TYPE: PRT
<213> ORGANISM: Artificial
<220> FEATURE:
<223> OTHER INFORMATION: Synthetic peptide

<400> SEQUENCE: 6

Glu Met Arg Leu Ser Lys Phe Phe Arg Asp Phe Ile Leu Gln Arg Lys
1               5                   10                  15

Lys

<210> SEQ ID NO 7
<211> LENGTH: 17
<212> TYPE: PRT
<213> ORGANISM: Artificial
<220> FEATURE:
<223> OTHER INFORMATION: Synthetic peptide

<400> SEQUENCE: 7

Glu Met Arg Ile Ser Arg Ile Ile Leu Asp Phe Leu Phe Leu Arg Lys
1               5                   10                  15

Lys

<210> SEQ ID NO 8
<211> LENGTH: 8
<212> TYPE: PRT
<213> ORGANISM: Artificial
<220> FEATURE:
<223> OTHER INFORMATION: Synthetic peptide

<400> SEQUENCE: 8

Asn Ile Phe Glu Tyr Phe Leu Glu
1               5

<210> SEQ ID NO 9
<211> LENGTH: 8
<212> TYPE: PRT
<213> ORGANISM: Artificial
<220> FEATURE:
<223> OTHER INFORMATION: Synthetic peptide

<400> SEQUENCE: 9

Thr Phe Phe Arg Leu Phe Asn Arg
1               5

<210> SEQ ID NO 10
<211> LENGTH: 9

<212> TYPE: PRT
<213> ORGANISM: Artificial
<220> FEATURE:
<223> OTHER INFORMATION: Synthetic peptide

<400> SEQUENCE: 10

Thr Phe Phe Arg Leu Phe Asn Arg Ser
1               5

<210> SEQ ID NO 11
<211> LENGTH: 9
<212> TYPE: PRT
<213> ORGANISM: Artificial
<220> FEATURE:
<223> OTHER INFORMATION: Synthetic peptide

<400> SEQUENCE: 11

Thr Phe Phe Arg Leu Phe Asn Arg Ser
1               5

<210> SEQ ID NO 12
<211> LENGTH: 10
<212> TYPE: PRT
<213> ORGANISM: Artificial
<220> FEATURE:
<223> OTHER INFORMATION: Synthetic peptide

<400> SEQUENCE: 12

Thr Phe Phe Arg Leu Phe Asn Arg Ser Phe
1               5                   10

<210> SEQ ID NO 13
<211> LENGTH: 11
<212> TYPE: PRT
<213> ORGANISM: Artificial
<220> FEATURE:
<223> OTHER INFORMATION: Synthetic peptide

<400> SEQUENCE: 13

Thr Phe Phe Arg Leu Phe Asn Arg Ser Phe Thr
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic peptide

<400> SEQUENCE: 14

Thr Phe Phe Arg Leu Phe Asn Arg Ser Phe Thr Gln
1               5                   10

<210> SEQ ID NO 15
<211> LENGTH: 13
<212> TYPE: PRT
<213> ORGANISM: Artificial
<220> FEATURE:
<223> OTHER INFORMATION: Synthetic peptide

<400> SEQUENCE: 15

Thr Phe Phe Arg Leu Phe Asn Arg Ser Phe Thr Gln Ala
1               5                   10

<210> SEQ ID NO 16
<211> LENGTH: 14
<212> TYPE: PRT

<213> ORGANISM: Artificial
<220> FEATURE:
<223> OTHER INFORMATION: Synthetic peptide

<400> SEQUENCE: 16

Thr Phe Phe Arg Leu Phe Asn Arg Ser Phe Thr Gln Ala Leu
1               5                   10

<210> SEQ ID NO 17
<211> LENGTH: 15
<212> TYPE: PRT
<213> ORGANISM: Artificial
<220> FEATURE:
<223> OTHER INFORMATION: Synthetic peptide

<400> SEQUENCE: 17

Thr Phe Phe Arg Leu Phe Asn Arg Ser Phe Thr Gln Ala Leu Gly
1               5                   10                  15

<210> SEQ ID NO 18
<211> LENGTH: 16
<212> TYPE: PRT
<213> ORGANISM: Artificial
<220> FEATURE:
<223> OTHER INFORMATION: Synthetic peptide

<400> SEQUENCE: 18

Thr Phe Phe Arg Leu Phe Asn Arg Ser Phe Thr Gln Ala Leu Gly Lys
1               5                   10                  15

<210> SEQ ID NO 19
<211> LENGTH: 9
<212> TYPE: PRT
<213> ORGANISM: Artificial
<220> FEATURE:
<223> OTHER INFORMATION: Synthetic peptide

<400> SEQUENCE: 19

Ser Thr Phe Phe Arg Leu Phe Asn Arg
1               5

<210> SEQ ID NO 20
<211> LENGTH: 10
<212> TYPE: PRT
<213> ORGANISM: Artificial
<220> FEATURE:
<223> OTHER INFORMATION: Synthetic peptide

<400> SEQUENCE: 20

Ser Thr Phe Phe Arg Leu Phe Asn Arg Ser
1               5                   10

<210> SEQ ID NO 21
<211> LENGTH: 10
<212> TYPE: PRT
<213> ORGANISM: Artificial
<220> FEATURE:
<223> OTHER INFORMATION: Synthetic peptide

<400> SEQUENCE: 21

Ser Thr Phe Phe Arg Leu Phe Asn Arg Ser
1               5                   10

<210> SEQ ID NO 22
<211> LENGTH: 11
<212> TYPE: PRT
<213> ORGANISM: Artificial

<220> FEATURE:
<223> OTHER INFORMATION: Synthetic peptide

<400> SEQUENCE: 22

Ser Thr Phe Phe Arg Leu Phe Asn Arg Ser Phe
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic peptide

<400> SEQUENCE: 23

Ser Thr Phe Phe Arg Leu Phe Asn Arg Ser Phe Thr
1               5                   10

<210> SEQ ID NO 24
<211> LENGTH: 13
<212> TYPE: PRT
<213> ORGANISM: Artificial
<220> FEATURE:
<223> OTHER INFORMATION: Synthetic peptide

<400> SEQUENCE: 24

Ser Thr Phe Phe Arg Leu Phe Asn Arg Ser Phe Thr Gln
1               5                   10

<210> SEQ ID NO 25
<211> LENGTH: 14
<212> TYPE: PRT
<213> ORGANISM: Artificial
<220> FEATURE:
<223> OTHER INFORMATION: Synthetic peptide

<400> SEQUENCE: 25

Ser Thr Phe Phe Arg Leu Phe Asn Arg Ser Phe Thr Gln Ala
1               5                   10

<210> SEQ ID NO 26
<211> LENGTH: 15
<212> TYPE: PRT
<213> ORGANISM: Artificial
<220> FEATURE:
<223> OTHER INFORMATION: Synthetic peptide

<400> SEQUENCE: 26

Ser Thr Phe Phe Arg Leu Phe Asn Arg Ser Phe Thr Gln Ala Leu
1               5                   10                  15

<210> SEQ ID NO 27
<211> LENGTH: 16
<212> TYPE: PRT
<213> ORGANISM: Artificial
<220> FEATURE:
<223> OTHER INFORMATION: Synthetic peptide

<400> SEQUENCE: 27

Ser Thr Phe Phe Arg Leu Phe Asn Arg Ser Phe Thr Gln Ala Leu Gly
1               5                   10                  15

<210> SEQ ID NO 28
<211> LENGTH: 17
<212> TYPE: PRT
<213> ORGANISM: Artificial
<220> FEATURE:

<223> OTHER INFORMATION: Synthetic peptide

<400> SEQUENCE: 28

Ser Thr Phe Phe Arg Leu Phe Asn Arg Ser Phe Thr Gln Ala Leu Gly
1               5                   10                  15
Lys

<210> SEQ ID NO 29
<211> LENGTH: 10
<212> TYPE: PRT
<213> ORGANISM: Artificial
<220> FEATURE:
<223> OTHER INFORMATION: Synthetic peptide

<400> SEQUENCE: 29

Leu Ser Thr Phe Phe Arg Leu Phe Asn Arg
1               5                   10

<210> SEQ ID NO 30
<211> LENGTH: 11
<212> TYPE: PRT
<213> ORGANISM: Artificial
<220> FEATURE:
<223> OTHER INFORMATION: Synthetic peptide

<400> SEQUENCE: 30

Leu Ser Thr Phe Phe Arg Leu Phe Asn Arg Ser
1               5                   10

<210> SEQ ID NO 31
<211> LENGTH: 11
<212> TYPE: PRT
<213> ORGANISM: Artificial
<220> FEATURE:
<223> OTHER INFORMATION: Synthetic peptide

<400> SEQUENCE: 31

Leu Ser Thr Phe Phe Arg Leu Phe Asn Arg Ser
1               5                   10

<210> SEQ ID NO 32
<211> LENGTH: 12
<212> TYPE: PRT
<213> ORGANISM: Artificial
<220> FEATURE:
<223> OTHER INFORMATION: Synthetic peptide

<400> SEQUENCE: 32

Leu Ser Thr Phe Phe Arg Leu Phe Asn Arg Ser Phe
1               5                   10

<210> SEQ ID NO 33
<211> LENGTH: 13
<212> TYPE: PRT
<213> ORGANISM: Artificial
<220> FEATURE:
<223> OTHER INFORMATION: Synthetic peptide

<400> SEQUENCE: 33

Leu Ser Thr Phe Phe Arg Leu Phe Asn Arg Ser Phe Thr
1               5                   10

<210> SEQ ID NO 34
<211> LENGTH: 14
<212> TYPE: PRT
<213> ORGANISM: Artificial

```
<220> FEATURE:
<223> OTHER INFORMATION: Synthetic peptide

<400> SEQUENCE: 34

Leu Ser Thr Phe Phe Arg Leu Phe Asn Arg Ser Phe Thr Gln
1               5                   10

<210> SEQ ID NO 35
<211> LENGTH: 15
<212> TYPE: PRT
<213> ORGANISM: Artificial
<220> FEATURE:
<223> OTHER INFORMATION: Synthetic peptide

<400> SEQUENCE: 35

Leu Ser Thr Phe Phe Arg Leu Phe Asn Arg Ser Phe Thr Gln Ala
1               5                   10                  15

<210> SEQ ID NO 36
<211> LENGTH: 16
<212> TYPE: PRT
<213> ORGANISM: Artificial
<220> FEATURE:
<223> OTHER INFORMATION: Synthetic peptide

<400> SEQUENCE: 36

Leu Ser Thr Phe Phe Arg Leu Phe Asn Arg Ser Phe Thr Gln Ala Leu
1               5                   10                  15

<210> SEQ ID NO 37
<211> LENGTH: 17
<212> TYPE: PRT
<213> ORGANISM: Artificial
<220> FEATURE:
<223> OTHER INFORMATION: Synthetic peptide

<400> SEQUENCE: 37

Leu Ser Thr Phe Phe Arg Leu Phe Asn Arg Ser Phe Thr Gln Ala Leu
1               5                   10                  15

Gly

<210> SEQ ID NO 38
<211> LENGTH: 18
<212> TYPE: PRT
<213> ORGANISM: Artificial
<220> FEATURE:
<223> OTHER INFORMATION: Synthetic peptide

<400> SEQUENCE: 38

Leu Ser Thr Phe Phe Arg Leu Phe Asn Arg Ser Phe Thr Gln Ala Leu
1               5                   10                  15

Gly Lys

<210> SEQ ID NO 39
<211> LENGTH: 11
<212> TYPE: PRT
<213> ORGANISM: Artificial
<220> FEATURE:
<223> OTHER INFORMATION: Synthetic peptide

<400> SEQUENCE: 39

Ser Leu Ser Thr Phe Phe Arg Leu Phe Asn Arg
1               5                   10

<210> SEQ ID NO 40
```

```
<211> LENGTH: 12
<212> TYPE: PRT
<213> ORGANISM: Artificial
<220> FEATURE:
<223> OTHER INFORMATION: Synthetic peptide

<400> SEQUENCE: 40

Ser Leu Ser Thr Phe Phe Arg Leu Phe Asn Arg Ser
1               5                   10

<210> SEQ ID NO 41
<211> LENGTH: 12
<212> TYPE: PRT
<213> ORGANISM: Artificial
<220> FEATURE:
<223> OTHER INFORMATION: Synthetic peptide

<400> SEQUENCE: 41

Ser Leu Ser Thr Phe Phe Arg Leu Phe Asn Arg Ser
1               5                   10

<210> SEQ ID NO 42
<211> LENGTH: 13
<212> TYPE: PRT
<213> ORGANISM: Artificial
<220> FEATURE:
<223> OTHER INFORMATION: Synthetic peptide

<400> SEQUENCE: 42

Ser Leu Ser Thr Phe Phe Arg Leu Phe Asn Arg Ser Phe
1               5                   10

<210> SEQ ID NO 43
<211> LENGTH: 14
<212> TYPE: PRT
<213> ORGANISM: Artificial
<220> FEATURE:
<223> OTHER INFORMATION: Synthetic peptide

<400> SEQUENCE: 43

Ser Leu Ser Thr Phe Phe Arg Leu Phe Asn Arg Ser Phe Thr
1               5                   10

<210> SEQ ID NO 44
<211> LENGTH: 15
<212> TYPE: PRT
<213> ORGANISM: Artificial
<220> FEATURE:
<223> OTHER INFORMATION: Synthetic peptide

<400> SEQUENCE: 44

Ser Leu Ser Thr Phe Phe Arg Leu Phe Asn Arg Ser Phe Thr Gln
1               5                   10                  15

<210> SEQ ID NO 45
<211> LENGTH: 16
<212> TYPE: PRT
<213> ORGANISM: Artificial
<220> FEATURE:
<223> OTHER INFORMATION: Synthetic peptide

<400> SEQUENCE: 45

Ser Leu Ser Thr Phe Phe Arg Leu Phe Asn Arg Ser Phe Thr Gln Ala
1               5                   10                  15

<210> SEQ ID NO 46
<211> LENGTH: 17
```

```
<212> TYPE: PRT
<213> ORGANISM: Artificial
<220> FEATURE:
<223> OTHER INFORMATION: Synthetic peptide

<400> SEQUENCE: 46

Ser Leu Ser Thr Phe Phe Arg Leu Phe Asn Arg Ser Phe Thr Gln Ala
1               5                   10                  15

Leu

<210> SEQ ID NO 47
<211> LENGTH: 18
<212> TYPE: PRT
<213> ORGANISM: Artificial
<220> FEATURE:
<223> OTHER INFORMATION: Synthetic peptide

<400> SEQUENCE: 47

Ser Leu Ser Thr Phe Phe Arg Leu Phe Asn Arg Ser Phe Thr Gln Ala
1               5                   10                  15

Leu Gly

<210> SEQ ID NO 48
<211> LENGTH: 19
<212> TYPE: PRT
<213> ORGANISM: Artificial
<220> FEATURE:
<223> OTHER INFORMATION: Synthetic peptide

<400> SEQUENCE: 48

Ser Leu Ser Thr Phe Phe Arg Leu Phe Asn Arg Ser Phe Thr Gln Ala
1               5                   10                  15

Leu Gly Lys

<210> SEQ ID NO 49
<211> LENGTH: 12
<212> TYPE: PRT
<213> ORGANISM: Artificial
<220> FEATURE:
<223> OTHER INFORMATION: Synthetic peptide

<400> SEQUENCE: 49

Gly Ser Leu Ser Thr Phe Phe Arg Leu Phe Asn Arg
1               5                   10

<210> SEQ ID NO 50
<211> LENGTH: 13
<212> TYPE: PRT
<213> ORGANISM: Artificial
<220> FEATURE:
<223> OTHER INFORMATION: Synthetic peptide

<400> SEQUENCE: 50

Gly Ser Leu Ser Thr Phe Phe Arg Leu Phe Asn Arg Ser
1               5                   10

<210> SEQ ID NO 51
<211> LENGTH: 13
<212> TYPE: PRT
<213> ORGANISM: Artificial
<220> FEATURE:
<223> OTHER INFORMATION: Synthetic peptide

<400> SEQUENCE: 51

Gly Ser Leu Ser Thr Phe Phe Arg Leu Phe Asn Arg Ser
```

1               5                   10

<210> SEQ ID NO 52
<211> LENGTH: 14
<212> TYPE: PRT
<213> ORGANISM: Artificial
<220> FEATURE:
<223> OTHER INFORMATION: Synthetic peptide

<400> SEQUENCE: 52

Gly Ser Leu Ser Thr Phe Phe Arg Leu Phe Asn Arg Ser Phe
1               5                   10

<210> SEQ ID NO 53
<211> LENGTH: 15
<212> TYPE: PRT
<213> ORGANISM: Artificial
<220> FEATURE:
<223> OTHER INFORMATION: Synthetic peptide

<400> SEQUENCE: 53

Gly Ser Leu Ser Thr Phe Phe Arg Leu Phe Asn Arg Ser Phe Thr
1               5                   10                  15

<210> SEQ ID NO 54
<211> LENGTH: 16
<212> TYPE: PRT
<213> ORGANISM: Artificial
<220> FEATURE:
<223> OTHER INFORMATION: Synthetic peptide

<400> SEQUENCE: 54

Gly Ser Leu Ser Thr Phe Phe Arg Leu Phe Asn Arg Ser Phe Thr Gln
1               5                   10                  15

<210> SEQ ID NO 55
<211> LENGTH: 17
<212> TYPE: PRT
<213> ORGANISM: Artificial
<220> FEATURE:
<223> OTHER INFORMATION: Synthetic peptide

<400> SEQUENCE: 55

Gly Ser Leu Ser Thr Phe Phe Arg Leu Phe Asn Arg Ser Phe Thr Gln
1               5                   10                  15

Ala

<210> SEQ ID NO 56
<211> LENGTH: 18
<212> TYPE: PRT
<213> ORGANISM: Artificial
<220> FEATURE:
<223> OTHER INFORMATION: Synthetic peptide

<400> SEQUENCE: 56

Gly Ser Leu Ser Thr Phe Phe Arg Leu Phe Asn Arg Ser Phe Thr Gln
1               5                   10                  15

Ala Leu

<210> SEQ ID NO 57
<211> LENGTH: 19
<212> TYPE: PRT
<213> ORGANISM: Artificial
<220> FEATURE:
<223> OTHER INFORMATION: Synthetic peptide

```
<400> SEQUENCE: 57

Gly Ser Leu Ser Thr Phe Phe Arg Leu Phe Asn Arg Ser Phe Thr Gln
1               5                   10                  15

Ala Leu Gly

<210> SEQ ID NO 58
<211> LENGTH: 20
<212> TYPE: PRT
<213> ORGANISM: Artificial
<220> FEATURE:
<223> OTHER INFORMATION: Synthetic peptide

<400> SEQUENCE: 58

Gly Ser Leu Ser Thr Phe Phe Arg Leu Phe Asn Arg Ser Phe Thr Gln
1               5                   10                  15

Ala Leu Gly Lys
            20

<210> SEQ ID NO 59
<211> LENGTH: 13
<212> TYPE: PRT
<213> ORGANISM: Artificial
<220> FEATURE:
<223> OTHER INFORMATION: Synthetic peptide

<400> SEQUENCE: 59

Ser Gly Ser Leu Ser Thr Phe Phe Arg Leu Phe Asn Arg
1               5                   10

<210> SEQ ID NO 60
<211> LENGTH: 14
<212> TYPE: PRT
<213> ORGANISM: Artificial
<220> FEATURE:
<223> OTHER INFORMATION: Synthetic peptide

<400> SEQUENCE: 60

Ser Gly Ser Leu Ser Thr Phe Phe Arg Leu Phe Asn Arg Ser
1               5                   10

<210> SEQ ID NO 61
<211> LENGTH: 14
<212> TYPE: PRT
<213> ORGANISM: Artificial
<220> FEATURE:
<223> OTHER INFORMATION: Synthetic peptide

<400> SEQUENCE: 61

Ser Gly Ser Leu Ser Thr Phe Phe Arg Leu Phe Asn Arg Ser
1               5                   10

<210> SEQ ID NO 62
<211> LENGTH: 15
<212> TYPE: PRT
<213> ORGANISM: Artificial
<220> FEATURE:
<223> OTHER INFORMATION: Synthetic peptide

<400> SEQUENCE: 62

Ser Gly Ser Leu Ser Thr Phe Phe Arg Leu Phe Asn Arg Ser Phe
1               5                   10                  15

<210> SEQ ID NO 63
<211> LENGTH: 16
<212> TYPE: PRT
```

```
<213> ORGANISM: Artificial
<220> FEATURE:
<223> OTHER INFORMATION: Synthetic peptide

<400> SEQUENCE: 63

Ser Gly Ser Leu Ser Thr Phe Phe Arg Leu Phe Asn Arg Ser Phe Thr
1               5                   10                  15

<210> SEQ ID NO 64
<211> LENGTH: 17
<212> TYPE: PRT
<213> ORGANISM: Artificial
<220> FEATURE:
<223> OTHER INFORMATION: Synthetic peptide

<400> SEQUENCE: 64

Ser Gly Ser Leu Ser Thr Phe Phe Arg Leu Phe Asn Arg Ser Phe Thr
1               5                   10                  15

Gln

<210> SEQ ID NO 65
<211> LENGTH: 18
<212> TYPE: PRT
<213> ORGANISM: Artificial
<220> FEATURE:
<223> OTHER INFORMATION: Synthetic peptide

<400> SEQUENCE: 65

Ser Gly Ser Leu Ser Thr Phe Phe Arg Leu Phe Asn Arg Ser Phe Thr
1               5                   10                  15

Gln Ala

<210> SEQ ID NO 66
<211> LENGTH: 19
<212> TYPE: PRT
<213> ORGANISM: Artificial
<220> FEATURE:
<223> OTHER INFORMATION: Synthetic peptide

<400> SEQUENCE: 66

Ser Gly Ser Leu Ser Thr Phe Phe Arg Leu Phe Asn Arg Ser Phe Thr
1               5                   10                  15

Gln Ala Leu

<210> SEQ ID NO 67
<211> LENGTH: 20
<212> TYPE: PRT
<213> ORGANISM: Artificial
<220> FEATURE:
<223> OTHER INFORMATION: Synthetic peptide

<400> SEQUENCE: 67

Ser Gly Ser Leu Ser Thr Phe Phe Arg Leu Phe Asn Arg Ser Phe Thr
1               5                   10                  15

Gln Ala Leu Gly
        20

<210> SEQ ID NO 68
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: misc_feature
```

```
<222> LOCATION: (1)..(1)
<223> OTHER INFORMATION: Xaa is a polar amino acid, or A
<220> FEATURE:
<221> NAME/KEY: misc_feature
<222> LOCATION: (2)..(2)
<223> OTHER INFORMATION: Xaa is F, W, Q, A, or an analog thereof
<220> FEATURE:
<221> NAME/KEY: misc_feature
<222> LOCATION: (5)..(5)
<223> OTHER INFORMATION: Xaa is a hydrophobic amino acid
<220> FEATURE:
<221> NAME/KEY: misc_feature
<222> LOCATION: (6)..(6)
<223> OTHER INFORMATION: Xaa is a hydrophobic amino acid, N, Q, or an
      analog thereof
<220> FEATURE:
<221> NAME/KEY: misc_feature
<222> LOCATION: (7)..(7)
<223> OTHER INFORMATION: Xaa is a polar amino acid, A, F, or an analog
      thereof
<220> FEATURE:
<221> NAME/KEY: misc_feature
<222> LOCATION: (9)..(9)
<223> OTHER INFORMATION: Xaa is a polar amino acid,
<220> FEATURE:
<221> NAME/KEY: misc_feature
<222> LOCATION: (10)..(10)
<223> OTHER INFORMATION: Xaa is a hydrophobic amino acid, Q, A, or an
      analog thereof
<220> FEATURE:
<221> NAME/KEY: misc_feature
<222> LOCATION: (11)..(11)
<223> OTHER INFORMATION: Xaa is a hydrophobic amino acid
<220> FEATURE:
<221> NAME/KEY: misc_feature
<222> LOCATION: (12)..(12)
<223> OTHER INFORMATION: Xaa is Q, A, or an analog thereof
<220> FEATURE:
<221> NAME/KEY: misc_feature
<222> LOCATION: (13)..(13)
<223> OTHER INFORMATION: Xaa is a non-polar amino acid;
<220> FEATURE:
<221> NAME/KEY: misc_feature
<222> LOCATION: (14)..(14)
<223> OTHER INFORMATION: Xaa is a hydrophobic amino acid
<220> FEATURE:
<221> NAME/KEY: misc_feature
<222> LOCATION: (15)..(15)
<223> OTHER INFORMATION: Xaa is a non-polar amino acid, N, S, D, or an
      analog thereof
<220> FEATURE:
<221> NAME/KEY: misc_feature
<222> LOCATION: (16)..(16)
<223> OTHER INFORMATION: Xaa is a polar amino acid, F, A, or an analog
      thereof

<400> SEQUENCE: 68

Xaa Xaa Phe Arg Xaa Xaa Xaa Arg Xaa Xaa Xaa Xaa Xaa Xaa Xaa Xaa
1               5                   10                  15

<210> SEQ ID NO 69
<211> LENGTH: 16
<212> TYPE: PRT
<213> ORGANISM: Artificial
<220> FEATURE:
<223> OTHER INFORMATION: Synthetic peptide

<400> SEQUENCE: 69

Thr Phe Phe Arg Leu Phe Asn Arg Ser Phe Thr Gln Ala Leu Gly Lys
1               5                   10                  15

<210> SEQ ID NO 70
<211> LENGTH: 16
<212> TYPE: PRT
<213> ORGANISM: Artificial
```

<220> FEATURE:
<223> OTHER INFORMATION: Synthetic peptide

<400> SEQUENCE: 70

Ala Phe Phe Arg Ala Phe Asn Arg Ala Phe Ala Gln Ala Leu Ala Lys
1               5                   10                  15

<210> SEQ ID NO 71
<211> LENGTH: 16
<212> TYPE: PRT
<213> ORGANISM: Artificial
<220> FEATURE:
<223> OTHER INFORMATION: Synthetic peptide

<400> SEQUENCE: 71

Thr Phe Phe Arg Ala Phe Ala Arg Ala Phe Ala Gln Ala Ala Ala Lys
1               5                   10                  15

<210> SEQ ID NO 72
<211> LENGTH: 16
<212> TYPE: PRT
<213> ORGANISM: Artificial
<220> FEATURE:
<223> OTHER INFORMATION: Synthetic peptide

<400> SEQUENCE: 72

Ala Phe Phe Arg Ala Phe Ala Arg Ala Phe Ala Gln Ala Leu Ala Lys
1               5                   10                  15

<210> SEQ ID NO 73
<211> LENGTH: 16
<212> TYPE: PRT
<213> ORGANISM: Artificial
<220> FEATURE:
<223> OTHER INFORMATION: Synthetic peptide

<400> SEQUENCE: 73

Ala Phe Phe Arg Leu Phe Ala Arg Ala Phe Ala Gln Ala Ala Ala Lys
1               5                   10                  15

<210> SEQ ID NO 74
<211> LENGTH: 16
<212> TYPE: PRT
<213> ORGANISM: Artificial
<220> FEATURE:
<223> OTHER INFORMATION: Synthetic peptide

<400> SEQUENCE: 74

Thr Leu Phe Arg Leu Leu Asn Arg Ser Leu Thr Gln Ala Leu Gly Lys
1               5                   10                  15

<210> SEQ ID NO 75
<211> LENGTH: 16
<212> TYPE: PRT
<213> ORGANISM: Artificial
<220> FEATURE:
<223> OTHER INFORMATION: Synthetic peptide

<400> SEQUENCE: 75

Thr Phe Phe Arg Leu Phe Asn Arg Ser Phe Thr Gln Ala Leu Phe Lys
1               5                   10                  15

<210> SEQ ID NO 76
<211> LENGTH: 16
<212> TYPE: PRT
<213> ORGANISM: Artificial
<220> FEATURE:

```
<223> OTHER INFORMATION: Synthetic peptide

<400> SEQUENCE: 76

Thr Phe Phe Arg Leu Phe Asn Arg Ser Leu Thr Gln Ala Leu Gly Lys
1               5                   10                  15

<210> SEQ ID NO 77
<211> LENGTH: 16
<212> TYPE: PRT
<213> ORGANISM: Artificial
<220> FEATURE:
<223> OTHER INFORMATION: Synthetic peptide

<400> SEQUENCE: 77

Thr Phe Phe Arg Leu Phe Asn Arg Ser Phe Thr Gln Ala Leu Asn Lys
1               5                   10                  15

<210> SEQ ID NO 78
<211> LENGTH: 16
<212> TYPE: PRT
<213> ORGANISM: Artificial
<220> FEATURE:
<223> OTHER INFORMATION: Synthetic peptide

<400> SEQUENCE: 78

Ala Phe Phe Arg Ala Phe Ala Arg Ala Phe Ala Gln Ala Ala Ala Lys
1               5                   10                  15

<210> SEQ ID NO 79
<211> LENGTH: 16
<212> TYPE: PRT
<213> ORGANISM: Artificial
<220> FEATURE:
<223> OTHER INFORMATION: Synthetic peptide

<400> SEQUENCE: 79

Ala Phe Phe Arg Ala Phe Asn Arg Ala Phe Ala Gln Ala Ala Ala Lys
1               5                   10                  15

<210> SEQ ID NO 80
<211> LENGTH: 16
<212> TYPE: PRT
<213> ORGANISM: Artificial
<220> FEATURE:
<223> OTHER INFORMATION: Synthetic peptide

<400> SEQUENCE: 80

Thr Phe Phe Arg Leu Phe Asn Arg Ser Phe Thr Gln Ala Leu Ser Lys
1               5                   10                  15

<210> SEQ ID NO 81
<211> LENGTH: 16
<212> TYPE: PRT
<213> ORGANISM: Artificial
<220> FEATURE:
<223> OTHER INFORMATION: Synthetic peptide

<400> SEQUENCE: 81

Ala Phe Phe Arg Ala Phe Ala Arg Ser Phe Ala Gln Ala Ala Ala Lys
1               5                   10                  15

<210> SEQ ID NO 82
<211> LENGTH: 16
<212> TYPE: PRT
<213> ORGANISM: Artificial
<220> FEATURE:
<223> OTHER INFORMATION: Synthetic peptide
```

<400> SEQUENCE: 82

Ala Phe Phe Arg Ala Phe Ala Arg Ala Phe Gln Ala Ala Gly Lys
1               5                   10                  15

<210> SEQ ID NO 83
<211> LENGTH: 16
<212> TYPE: PRT
<213> ORGANISM: Artificial
<220> FEATURE:
<223> OTHER INFORMATION: Synthetic peptide

<400> SEQUENCE: 83

Ala Phe Phe Arg Ala Phe Ala Arg Ala Phe Thr Gln Ala Ala Ala Lys
1               5                   10                  15

<210> SEQ ID NO 84
<211> LENGTH: 16
<212> TYPE: PRT
<213> ORGANISM: Artificial
<220> FEATURE:
<223> OTHER INFORMATION: Synthetic peptide

<400> SEQUENCE: 84

Thr Phe Phe Arg Leu Phe Asn Arg Ser Phe Thr Gln Ala Leu Gly Gln
1               5                   10                  15

<210> SEQ ID NO 85
<211> LENGTH: 16
<212> TYPE: PRT
<213> ORGANISM: Artificial
<220> FEATURE:
<223> OTHER INFORMATION: Synthetic peptide

<400> SEQUENCE: 85

Thr Phe Phe Arg Leu Leu Asn Arg Ser Phe Thr Gln Ala Leu Gly Lys
1               5                   10                  15

<210> SEQ ID NO 86
<211> LENGTH: 16
<212> TYPE: PRT
<213> ORGANISM: Artificial
<220> FEATURE:
<223> OTHER INFORMATION: Synthetic peptide

<400> SEQUENCE: 86

Thr Trp Phe Arg Leu Phe Asn Arg Ser Phe Thr Gln Ala Leu Gly Lys
1               5                   10                  15

<210> SEQ ID NO 87
<211> LENGTH: 16
<212> TYPE: PRT
<213> ORGANISM: Artificial
<220> FEATURE:
<223> OTHER INFORMATION: Synthetic peptide

<400> SEQUENCE: 87

Ala Phe Phe Arg Ala Phe Ala Arg Ala Phe Ala Gln Ala Phe Ala Lys
1               5                   10                  15

<210> SEQ ID NO 88
<211> LENGTH: 16
<212> TYPE: PRT
<213> ORGANISM: Artificial
<220> FEATURE:
<223> OTHER INFORMATION: Synthetic peptide

```
<400> SEQUENCE: 88

Thr Gln Phe Arg Leu Phe Asn Arg Ser Phe Thr Gln Ala Leu Gly Lys
1               5                   10                  15

<210> SEQ ID NO 89
<211> LENGTH: 16
<212> TYPE: PRT
<213> ORGANISM: Artificial
<220> FEATURE:
<223> OTHER INFORMATION: Synthetic peptide

<400> SEQUENCE: 89

Thr Phe Phe Arg Leu Phe Asn Arg Ser Phe Thr Gln Ala Leu Asp Lys
1               5                   10                  15

<210> SEQ ID NO 90
<211> LENGTH: 16
<212> TYPE: PRT
<213> ORGANISM: Artificial
<220> FEATURE:
<223> OTHER INFORMATION: Synthetic peptide

<400> SEQUENCE: 90

Thr Phe Phe Arg Leu Phe Asn Arg Ser Phe Thr Gln Ala Leu Ala Lys
1               5                   10                  15

<210> SEQ ID NO 91
<211> LENGTH: 16
<212> TYPE: PRT
<213> ORGANISM: Artificial
<220> FEATURE:
<223> OTHER INFORMATION: Synthetic peptide

<400> SEQUENCE: 91

Thr Phe Phe Arg Leu Phe Asn Arg Ser Phe Thr Gln Ala Leu Gly Glu
1               5                   10                  15

<210> SEQ ID NO 92
<211> LENGTH: 16
<212> TYPE: PRT
<213> ORGANISM: Artificial
<220> FEATURE:
<223> OTHER INFORMATION: Synthetic peptide

<400> SEQUENCE: 92

Thr Phe Phe Arg Leu Phe Ser Arg Ser Phe Thr Gln Ala Leu Gly Lys
1               5                   10                  15

<210> SEQ ID NO 93
<211> LENGTH: 16
<212> TYPE: PRT
<213> ORGANISM: Artificial
<220> FEATURE:
<223> OTHER INFORMATION: Synthetic peptide

<400> SEQUENCE: 93

Thr Phe Phe Arg Leu Phe Asn Arg Ser Phe Thr Gln Ala Leu Gly Ala
1               5                   10                  15

<210> SEQ ID NO 94
<211> LENGTH: 16
<212> TYPE: PRT
<213> ORGANISM: Artificial
<220> FEATURE:
<223> OTHER INFORMATION: Synthetic peptide

<400> SEQUENCE: 94
```

Thr Phe Phe Arg Leu Phe Asp Arg Ser Phe Thr Gln Ala Leu Gly Lys
1               5                   10                  15

<210> SEQ ID NO 95
<211> LENGTH: 16
<212> TYPE: PRT
<213> ORGANISM: Artificial
<220> FEATURE:
<223> OTHER INFORMATION: Synthetic peptide

<400> SEQUENCE: 95

Thr Phe Phe Arg Leu Phe Asn Arg Ser Phe Thr Gln Ala Leu Gly Phe
1               5                   10                  15

<210> SEQ ID NO 96
<211> LENGTH: 16
<212> TYPE: PRT
<213> ORGANISM: Artificial
<220> FEATURE:
<223> OTHER INFORMATION: Synthetic peptide

<400> SEQUENCE: 96

Thr Phe Phe Arg Ala Phe Ala Arg Ser Phe Thr Gln Ala Ala Ala Lys
1               5                   10                  15

<210> SEQ ID NO 97
<211> LENGTH: 16
<212> TYPE: PRT
<213> ORGANISM: Artificial
<220> FEATURE:
<223> OTHER INFORMATION: Synthetic peptide

<400> SEQUENCE: 97

Thr Phe Phe Arg Leu Phe Ala Arg Ser Phe Thr Gln Ala Ala Gly Lys
1               5                   10                  15

<210> SEQ ID NO 98
<211> LENGTH: 14
<212> TYPE: PRT
<213> ORGANISM: Artificial
<220> FEATURE:
<223> OTHER INFORMATION: Synthetic peptide

<400> SEQUENCE: 98

Thr Phe Phe Arg Leu Phe Asn Arg Ser Phe Thr Gln Leu Lys
1               5                   10

<210> SEQ ID NO 99
<211> LENGTH: 16
<212> TYPE: PRT
<213> ORGANISM: Artificial
<220> FEATURE:
<223> OTHER INFORMATION: Synthetic peptide

<400> SEQUENCE: 99

Thr Phe Phe Arg Leu Phe Asn Arg Ser Phe Thr Gln Ala Leu Gly Ser
1               5                   10                  15

<210> SEQ ID NO 100
<211> LENGTH: 16
<212> TYPE: PRT
<213> ORGANISM: Artificial
<220> FEATURE:
<223> OTHER INFORMATION: Synthetic peptide

<400> SEQUENCE: 100

Thr Leu Phe Arg Leu Phe Asn Arg Ser Phe Thr Gln Ala Leu Gly Lys
1               5                   10                  15

<210> SEQ ID NO 101
<211> LENGTH: 16
<212> TYPE: PRT
<213> ORGANISM: Artificial
<220> FEATURE:
<223> OTHER INFORMATION: Synthetic peptide

<400> SEQUENCE: 101

Thr Phe Phe Arg Leu Asn Phe Arg Ser Phe Thr Gln Ala Leu Gly Lys
1               5                   10                  15

<210> SEQ ID NO 102
<211> LENGTH: 16
<212> TYPE: PRT
<213> ORGANISM: Artificial
<220> FEATURE:
<223> OTHER INFORMATION: Synthetic peptide

<400> SEQUENCE: 102

Thr Phe Phe Arg Leu Phe Asn Arg Ser Gln Thr Gln Ala Leu Gly Lys
1               5                   10                  15

<210> SEQ ID NO 103
<211> LENGTH: 16
<212> TYPE: PRT
<213> ORGANISM: Artificial
<220> FEATURE:
<223> OTHER INFORMATION: Synthetic peptide

<400> SEQUENCE: 103

Thr Phe Phe Arg Leu Phe Ala Ala Ala Phe Thr Gln Ala Leu Gly Lys
1               5                   10                  15

<210> SEQ ID NO 104
<211> LENGTH: 16
<212> TYPE: PRT
<213> ORGANISM: Artificial
<220> FEATURE:
<223> OTHER INFORMATION: Synthetic peptide

<400> SEQUENCE: 104

Thr Phe Phe Arg Leu Phe Asn Arg Ser Phe Thr Gln Ala Leu Gly Lys
1               5                   10                  15

<210> SEQ ID NO 105
<211> LENGTH: 16
<212> TYPE: PRT
<213> ORGANISM: Artificial
<220> FEATURE:
<223> OTHER INFORMATION: Synthetic peptide

<400> SEQUENCE: 105

Thr Phe Phe Arg Leu Phe Asn Arg Ser Ala Ala Ala Ala Leu Gly Lys
1               5                   10                  15

<210> SEQ ID NO 106
<211> LENGTH: 16
<212> TYPE: PRT
<213> ORGANISM: Artificial
<220> FEATURE:
<223> OTHER INFORMATION: Synthetic peptide

<400> SEQUENCE: 106

Thr Phe Phe Arg Leu Phe Phe Arg Ser Asn Thr Gln Ala Leu Gly Lys

```
1               5                   10                  15
```

<210> SEQ ID NO 107
<211> LENGTH: 16
<212> TYPE: PRT
<213> ORGANISM: Artificial
<220> FEATURE:
<223> OTHER INFORMATION: Synthetic peptide

<400> SEQUENCE: 107

```
Thr Phe Phe Arg Leu Phe Asn Arg Ser Phe Thr Gln Pro Leu Gly Lys
1               5                   10                  15
```

<210> SEQ ID NO 108
<211> LENGTH: 16
<212> TYPE: PRT
<213> ORGANISM: Artificial
<220> FEATURE:
<223> OTHER INFORMATION: Synthetic peptide

<400> SEQUENCE: 108

```
Thr Ala Phe Arg Leu Ala Asn Arg Ser Ala Thr Gln Ala Leu Gly Lys
1               5                   10                  15
```

<210> SEQ ID NO 109
<211> LENGTH: 16
<212> TYPE: PRT
<213> ORGANISM: Artificial
<220> FEATURE:
<223> OTHER INFORMATION: Synthetic peptide

<400> SEQUENCE: 109

```
Thr Phe Phe Arg Leu Phe Asn Arg Ser Phe Thr Gln Ala Ala Ala Ala
1               5                   10                  15
```

<210> SEQ ID NO 110
<211> LENGTH: 16
<212> TYPE: PRT
<213> ORGANISM: Artificial
<220> FEATURE:
<223> OTHER INFORMATION: Synthetic peptide

<400> SEQUENCE: 110

```
Thr Phe Phe Arg Leu Gln Asn Arg Ser Phe Thr Gln Ala Leu Gly Lys
1               5                   10                  15
```

<210> SEQ ID NO 111
<211> LENGTH: 16
<212> TYPE: PRT
<213> ORGANISM: Artificial
<220> FEATURE:
<223> OTHER INFORMATION: Synthetic peptide

<400> SEQUENCE: 111

```
Thr Phe Phe Arg Leu Phe Asn Arg Ser Phe Thr Gln Ala Leu Pro Lys
1               5                   10                  15
```

<210> SEQ ID NO 112
<211> LENGTH: 16
<212> TYPE: PRT
<213> ORGANISM: Artificial
<220> FEATURE:
<223> OTHER INFORMATION: Synthetic peptide

<400> SEQUENCE: 112

```
Thr Tyr Tyr Arg Leu Phe Asn Arg Ser Phe Thr Gln Ala Leu Gly Lys
1               5                   10                  15
```

<210> SEQ ID NO 113
<211> LENGTH: 15
<212> TYPE: PRT
<213> ORGANISM: Artificial
<220> FEATURE:
<223> OTHER INFORMATION: Synthetic peptide

<400> SEQUENCE: 113

Thr Phe Phe Arg Leu Phe Arg Ser Phe Thr Gln Ala Leu Gly Lys
1               5                   10                  15

<210> SEQ ID NO 114
<211> LENGTH: 16
<212> TYPE: PRT
<213> ORGANISM: Artificial
<220> FEATURE:
<223> OTHER INFORMATION: Synthetic peptide

<400> SEQUENCE: 114

Thr Gln Phe Arg Leu Gln Asn Arg Ser Gln Thr Gln Ala Leu Gly Lys
1               5                   10                  15

<210> SEQ ID NO 115
<211> LENGTH: 16
<212> TYPE: PRT
<213> ORGANISM: Artificial
<220> FEATURE:
<223> OTHER INFORMATION: Synthetic peptide

<400> SEQUENCE: 115

Lys Asn Leu Arg Ile Ile Arg Lys Gly Ile His Ile Ile Lys Lys Tyr
1               5                   10                  15

<210> SEQ ID NO 116
<211> LENGTH: 18
<212> TYPE: PRT
<213> ORGANISM: Artificial
<220> FEATURE:
<223> OTHER INFORMATION: Synthetic peptide

<400> SEQUENCE: 116

Lys Asn Leu Arg Arg Ile Ile Arg Lys Gly Ile His Ile Ile Lys Lys
1               5                   10                  15

Tyr Gly

<210> SEQ ID NO 117
<211> LENGTH: 18
<212> TYPE: PRT
<213> ORGANISM: Artificial
<220> FEATURE:
<223> OTHER INFORMATION: Synthetic peptide

<400> SEQUENCE: 117

Lys Asn Leu Arg Arg Ile Ile Arg Lys Thr Ile His Ile Ile Lys Lys
1               5                   10                  15

Tyr Gly

<210> SEQ ID NO 118
<211> LENGTH: 18
<212> TYPE: PRT
<213> ORGANISM: Artificial
<220> FEATURE:
<223> OTHER INFORMATION: Synthetic peptide

<400> SEQUENCE: 118

```
Lys Asn Leu Arg Arg Ile Gly Arg Lys Ile Ile His Ile Ile Lys Lys
1               5                   10                  15

Tyr Gly

<210> SEQ ID NO 119
<211> LENGTH: 18
<212> TYPE: PRT
<213> ORGANISM: Artificial
<220> FEATURE:
<223> OTHER INFORMATION: Synthetic peptide

<400> SEQUENCE: 119

Lys Asn Leu Arg Arg Ile Thr Arg Lys Ile Ile His Ile Ile Lys Lys
1               5                   10                  15

Tyr Gly

<210> SEQ ID NO 120
<211> LENGTH: 18
<212> TYPE: PRT
<213> ORGANISM: Artificial
<220> FEATURE:
<223> OTHER INFORMATION: Synthetic peptide

<400> SEQUENCE: 120

Lys Asn Leu Arg Arg Ile Ile Arg Lys Ile Ile His Ile Ile Lys Lys
1               5                   10                  15

Tyr Gly

<210> SEQ ID NO 121
<211> LENGTH: 18
<212> TYPE: PRT
<213> ORGANISM: Artificial
<220> FEATURE:
<223> OTHER INFORMATION: Synthetic peptide

<400> SEQUENCE: 121

Gly Leu Leu Arg Arg Leu Arg Lys Lys Ile Gly Glu Ile Phe Lys Lys
1               5                   10                  15

Tyr Gly

<210> SEQ ID NO 122
<211> LENGTH: 18
<212> TYPE: PRT
<213> ORGANISM: Artificial
<220> FEATURE:
<223> OTHER INFORMATION: Synthetic peptide

<400> SEQUENCE: 122

Arg Gly Gly Arg Leu Cys Tyr Cys Arg Arg Arg Phe Cys Val Cys Val
1               5                   10                  15

Gly Arg

<210> SEQ ID NO 123
<211> LENGTH: 17
<212> TYPE: PRT
<213> ORGANISM: Artificial
<220> FEATURE:
<223> OTHER INFORMATION: Synthetic peptide

<400> SEQUENCE: 123

Gly Leu Gly Arg Val Ile Gly Arg Leu Ile Lys Gln Ile Ile Trp Arg
1               5                   10                  15
```

Arg

<210> SEQ ID NO 124
<211> LENGTH: 19
<212> TYPE: PRT
<213> ORGANISM: Artificial
<220> FEATURE:
<223> OTHER INFORMATION: Synthetic peptide

<400> SEQUENCE: 124

Val Tyr Arg Lys Arg Lys Ser Ile Leu Lys Ile Tyr Ala Lys Leu Lys
1               5                   10                  15

Gly Trp His

<210> SEQ ID NO 125
<211> LENGTH: 20
<212> TYPE: PRT
<213> ORGANISM: Artificial
<220> FEATURE:
<223> OTHER INFORMATION: Synthetic peptide

<400> SEQUENCE: 125

Asn Tyr Arg Leu Val Asn Ala Ile Phe Ser Lys Ile Phe Lys Lys Lys
1               5                   10                  15

Phe Ile Lys Phe
            20

<210> SEQ ID NO 126
<211> LENGTH: 11
<212> TYPE: PRT
<213> ORGANISM: Artificial
<220> FEATURE:
<223> OTHER INFORMATION: Synthetic peptide

<400> SEQUENCE: 126

Lys Ile Leu Lys Phe Leu Phe Lys Lys Val Phe
1               5                   10

<210> SEQ ID NO 127
<211> LENGTH: 11
<212> TYPE: PRT
<213> ORGANISM: Artificial
<220> FEATURE:
<223> OTHER INFORMATION: Synthetic peptide

<400> SEQUENCE: 127

Phe Ile Arg Lys Phe Leu Lys Lys Trp Leu Leu
1               5                   10

<210> SEQ ID NO 128
<211> LENGTH: 11
<212> TYPE: PRT
<213> ORGANISM: Artificial
<220> FEATURE:
<223> OTHER INFORMATION: Synthetic peptide

<400> SEQUENCE: 128

Lys Leu Phe Lys Phe Leu Arg Lys His Leu Leu
1               5                   10

<210> SEQ ID NO 129
<211> LENGTH: 11
<212> TYPE: PRT
<213> ORGANISM: Artificial
<220> FEATURE:
<223> OTHER INFORMATION: Synthetic peptide

<400> SEQUENCE: 129

Lys Ile Leu Lys Phe Leu Phe Lys Gln Val Phe
1               5                   10

<210> SEQ ID NO 130
<211> LENGTH: 11
<212> TYPE: PRT
<213> ORGANISM: Artificial
<220> FEATURE:
<223> OTHER INFORMATION: Synthetic peptide

<400> SEQUENCE: 130

Lys Ile Leu Lys Lys Leu Phe Lys Phe Val Phe
1               5                   10

<210> SEQ ID NO 131
<211> LENGTH: 11
<212> TYPE: PRT
<213> ORGANISM: Artificial
<220> FEATURE:
<223> OTHER INFORMATION: Synthetic peptide

<400> SEQUENCE: 131

Gly Ile Leu Lys Lys Leu Phe Thr Lys Val Phe
1               5                   10

<210> SEQ ID NO 132
<211> LENGTH: 9
<212> TYPE: PRT
<213> ORGANISM: Artificial
<220> FEATURE:
<223> OTHER INFORMATION: Synthetic peptide

<400> SEQUENCE: 132

Leu Arg Lys Phe Leu His Lys Leu Phe
1               5

<210> SEQ ID NO 133
<211> LENGTH: 9
<212> TYPE: PRT
<213> ORGANISM: Artificial
<220> FEATURE:
<223> OTHER INFORMATION: Synthetic peptide

<400> SEQUENCE: 133

Leu Arg Lys Asn Leu Arg Trp Leu Phe
1               5

<210> SEQ ID NO 134
<211> LENGTH: 11
<212> TYPE: PRT
<213> ORGANISM: Artificial
<220> FEATURE:
<223> OTHER INFORMATION: Synthetic peptide

<400> SEQUENCE: 134

Phe Ile Arg Lys Phe Leu Gln Lys Leu His Leu
1               5                   10

<210> SEQ ID NO 135
<211> LENGTH: 11
<212> TYPE: PRT
<213> ORGANISM: Artificial
<220> FEATURE:
<223> OTHER INFORMATION: Synthetic peptide

```
<400> SEQUENCE: 135

Phe Thr Arg Lys Phe Leu Lys Phe Leu His Leu
1               5                   10

<210> SEQ ID NO 136
<211> LENGTH: 12
<212> TYPE: PRT
<213> ORGANISM: Artificial
<220> FEATURE:
<223> OTHER INFORMATION: Synthetic peptide

<400> SEQUENCE: 136

Lys Lys Phe Lys Lys Phe Lys Val Leu Lys Ile Leu
1               5                   10

<210> SEQ ID NO 137
<211> LENGTH: 12
<212> TYPE: PRT
<213> ORGANISM: Artificial
<220> FEATURE:
<223> OTHER INFORMATION: Synthetic peptide

<400> SEQUENCE: 137

Leu Leu Lys Leu Leu Lys Leu Lys Lys Leu Lys Phe
1               5                   10

<210> SEQ ID NO 138
<211> LENGTH: 14
<212> TYPE: PRT
<213> ORGANISM: Artificial
<220> FEATURE:
<223> OTHER INFORMATION: Synthetic peptide

<400> SEQUENCE: 138

Phe Leu Lys Phe Leu Lys Lys Phe Phe Lys Lys Leu Lys Tyr
1               5                   10

<210> SEQ ID NO 139
<211> LENGTH: 16
<212> TYPE: PRT
<213> ORGANISM: Artificial
<220> FEATURE:
<223> OTHER INFORMATION: Synthetic peptide

<400> SEQUENCE: 139

Gly Trp Leu Lys Met Phe Lys Lys Ile Ile Gly Lys Phe Gly Lys Phe
1               5                   10                  15

<210> SEQ ID NO 140
<211> LENGTH: 16
<212> TYPE: PRT
<213> ORGANISM: Artificial
<220> FEATURE:
<223> OTHER INFORMATION: Synthetic peptide

<400> SEQUENCE: 140

Gly Ile Phe Lys Lys Phe Val Lys Ile Leu Tyr Lys Val Gln Lys Leu
1               5                   10                  15

<210> SEQ ID NO 141
<211> LENGTH: 24
<212> TYPE: PRT
<213> ORGANISM: Artificial
<220> FEATURE:
<223> OTHER INFORMATION: Synthetic peptide

<400> SEQUENCE: 141
```

```
Gly Arg Leu Val Leu Glu Ile Thr Ala Asp Glu Val Lys Ala Leu Gly
1               5                   10                  15

Glu Ala Leu Ala Asn Ala Lys Ile
            20

<210> SEQ ID NO 142
<211> LENGTH: 21
<212> TYPE: PRT
<213> ORGANISM: Artificial
<220> FEATURE:
<223> OTHER INFORMATION: Synthetic peptide

<400> SEQUENCE: 142

Tyr Ile Gln Phe His Leu Asn Gln Gln Pro Arg Pro Lys Val Lys Lys
1               5                   10                  15

Ile Lys Ile Phe Leu
            20

<210> SEQ ID NO 143
<211> LENGTH: 32
<212> TYPE: PRT
<213> ORGANISM: Artificial
<220> FEATURE:
<223> OTHER INFORMATION: Synthetic peptide

<400> SEQUENCE: 143

Gly Ser Val Ile Lys Lys Arg Arg Lys Arg Met Ala Lys Lys Lys His
1               5                   10                  15

Arg Lys Leu Leu Lys Lys Thr Arg Ile Gln Arg Arg Ala Gly Lys
            20                  25                  30

<210> SEQ ID NO 144
<211> LENGTH: 30
<212> TYPE: PRT
<213> ORGANISM: Artificial
<220> FEATURE:
<223> OTHER INFORMATION: Synthetic peptide

<400> SEQUENCE: 144

Met Arg Phe Gly Ser Leu Ala Leu Val Ala Tyr Asp Ser Ala Ile Lys
1               5                   10                  15

His Ser Trp Pro Arg Pro Ser Ser Val Arg Arg Leu Arg Met
            20                  25                  30

<210> SEQ ID NO 145
<211> LENGTH: 39
<212> TYPE: PRT
<213> ORGANISM: Artificial
<220> FEATURE:
<223> OTHER INFORMATION: Synthetic peptide

<400> SEQUENCE: 145

Phe Glu Ser Lys Ile Leu Asn Ala Ser Lys Glu Leu Asp Lys Glu Lys
1               5                   10                  15

Lys Val Asn Thr Ala Leu Ser Phe Asn Ser His Gln Asp Phe Ala Lys
            20                  25                  30

Ala Tyr Gln Asn Gly Lys Ile
        35

<210> SEQ ID NO 146
<211> LENGTH: 18
<212> TYPE: PRT
<213> ORGANISM: Artificial
```

<220> FEATURE:
<223> OTHER INFORMATION: Synthetic peptide

<400> SEQUENCE: 146

Trp Ser Arg Val Pro Gly His Ser Asp Thr Gly Trp Lys Val Trp His
1               5                   10                  15

Arg Trp

<210> SEQ ID NO 147
<211> LENGTH: 21
<212> TYPE: PRT
<213> ORGANISM: Artificial
<220> FEATURE:
<223> OTHER INFORMATION: Synthetic peptide

<400> SEQUENCE: 147

Met Gly Ile Ile Ala Gly Ile Ile Lys Phe Ile Lys Gly Leu Ile Glu
1               5                   10                  15

Lys Phe Thr Gly Lys
            20

<210> SEQ ID NO 148
<211> LENGTH: 16
<212> TYPE: PRT
<213> ORGANISM: Artificial
<220> FEATURE:
<223> OTHER INFORMATION: Synthetic peptide

<400> SEQUENCE: 148

Arg Glu Ser Lys Leu Ile Ala Met Ala Asp Met Ile Arg Arg Arg Ile
1               5                   10                  15

<210> SEQ ID NO 149
<211> LENGTH: 24
<212> TYPE: PRT
<213> ORGANISM: Artificial
<220> FEATURE:
<223> OTHER INFORMATION: Synthetic peptide

<400> SEQUENCE: 149

Leu Ser Leu Ala Thr Phe Ala Lys Ile Phe Met Thr Arg Ser Asn Trp
1               5                   10                  15

Ser Leu Lys Arg Phe Asn Arg Leu
            20

<210> SEQ ID NO 150
<211> LENGTH: 30
<212> TYPE: PRT
<213> ORGANISM: Artificial
<220> FEATURE:
<223> OTHER INFORMATION: Synthetic peptide

<400> SEQUENCE: 150

Met Ile Arg Ile Arg Ser Pro Thr Lys Lys Lys Leu Asn Arg Asn Ser
1               5                   10                  15

Ile Ser Asp Trp Lys Ser Asn Thr Ser Gly Arg Phe Phe Tyr
            20                  25                  30

<210> SEQ ID NO 151
<211> LENGTH: 37
<212> TYPE: PRT
<213> ORGANISM: Artificial
<220> FEATURE:
<223> OTHER INFORMATION: Synthetic peptide

```
<400> SEQUENCE: 151

Met Lys Arg Arg Arg Cys Asn Trp Cys Gly Lys Leu Phe Tyr Leu Glu
1               5                   10                  15

Glu Lys Ser Lys Glu Ala Tyr Cys Cys Lys Glu Cys Arg Lys Lys Ala
            20                  25                  30

Lys Lys Val Lys Lys
        35

<210> SEQ ID NO 152
<211> LENGTH: 28
<212> TYPE: PRT
<213> ORGANISM: Artificial
<220> FEATURE:
<223> OTHER INFORMATION: Synthetic peptide

<400> SEQUENCE: 152

Val Leu Pro Phe Pro Ala Ile Pro Leu Ser Arg Arg Arg Ala Cys Val
1               5                   10                  15

Ala Ala Pro Arg Pro Arg Ser Arg Gln Arg Ala Ser
            20                  25

<210> SEQ ID NO 153
<211> LENGTH: 30
<212> TYPE: PRT
<213> ORGANISM: Artificial
<220> FEATURE:
<223> OTHER INFORMATION: Synthetic peptide

<400> SEQUENCE: 153

Lys Asn Lys Lys Gln Thr Asp Ile Leu Glu Lys Val Lys Glu Ile Leu
1               5                   10                  15

Asp Lys Lys Lys Lys Thr Lys Ser Val Gly Gln Lys Leu Tyr
            20                  25                  30

<210> SEQ ID NO 154
<211> LENGTH: 15
<212> TYPE: PRT
<213> ORGANISM: Artificial
<220> FEATURE:
<223> OTHER INFORMATION: Synthetic peptide

<400> SEQUENCE: 154

Ser Leu Gln Ser Gln Leu Gly Pro Cys Leu His Asp Gln Arg His
1               5                   10                  15

<210> SEQ ID NO 155
<211> LENGTH: 28
<212> TYPE: PRT
<213> ORGANISM: Artificial
<220> FEATURE:
<223> OTHER INFORMATION: Synthetic peptide

<400> SEQUENCE: 155

Lys Phe Gln Gly Glu Phe Thr Asn Ile Gly Gln Ser Tyr Ile Val Ser
1               5                   10                  15

Ala Ser His Met Ser Thr Ser Leu Asn Thr Gly Lys
            20                  25

<210> SEQ ID NO 156
<211> LENGTH: 41
<212> TYPE: PRT
<213> ORGANISM: Artificial
<220> FEATURE:
<223> OTHER INFORMATION: Synthetic peptide
```

<400> SEQUENCE: 156

Thr Lys Lys Ile Glu Leu Lys Arg Phe Val Asp Ala Phe Val Lys Lys
1               5                   10                  15

Ser Tyr Glu Asn Tyr Ile Leu Glu Arg Glu Leu Lys Lys Leu Ile Lys
            20                  25                  30

Ala Ile Asn Glu Glu Leu Pro Thr Lys
        35                  40

<210> SEQ ID NO 157
<211> LENGTH: 20
<212> TYPE: PRT
<213> ORGANISM: Artificial
<220> FEATURE:
<223> OTHER INFORMATION: Synthetic peptide

<400> SEQUENCE: 157

Lys Phe Ser Asp Gln Ile Asp Lys Gly Gln Asp Ala Leu Lys Asp Lys
1               5                   10                  15

Leu Gly Asp Leu
            20

<210> SEQ ID NO 158
<211> LENGTH: 13
<212> TYPE: PRT
<213> ORGANISM: Artificial
<220> FEATURE:
<223> OTHER INFORMATION: Synthetic peptide

<400> SEQUENCE: 158

Leu Ser Glu Met Glu Arg Arg Leu Arg Lys Arg Ala
1               5                   10

<210> SEQ ID NO 159
<211> LENGTH: 25
<212> TYPE: PRT
<213> ORGANISM: Artificial
<220> FEATURE:
<223> OTHER INFORMATION: Synthetic peptide

<400> SEQUENCE: 159

Arg Arg Gly Cys Thr Glu Arg Leu Arg Arg Met Ala Arg Arg Asn Ala
1               5                   10                  15

Trp Asp Leu Tyr Ala Glu His Phe Tyr
            20                  25

<210> SEQ ID NO 160
<211> LENGTH: 26
<212> TYPE: PRT
<213> ORGANISM: Artificial
<220> FEATURE:
<223> OTHER INFORMATION: Synthetic peptide

<400> SEQUENCE: 160

Ser Lys Phe Lys Val Leu Arg Lys Ile Ile Lys Glu Tyr Lys Gly
1               5                   10                  15

Glu Leu Met Leu Ser Ile Gln Lys Gln Arg
            20                  25

<210> SEQ ID NO 161
<211> LENGTH: 20
<212> TYPE: PRT
<213> ORGANISM: Artificial
<220> FEATURE:

<223> OTHER INFORMATION: Synthetic peptide

<400> SEQUENCE: 161

Phe Glu Leu Val Asp Trp Leu Glu Thr Asn Leu Gly Lys Ile Leu Lys
1               5                   10                  15

Ser Lys Ser Ala
            20

<210> SEQ ID NO 162
<211> LENGTH: 22
<212> TYPE: PRT
<213> ORGANISM: Artificial
<220> FEATURE:
<223> OTHER INFORMATION: Synthetic peptide

<400> SEQUENCE: 162

Leu Val Leu Arg Ile Cys Thr Asp Leu Phe Thr Phe Ile Lys Trp Thr
1               5                   10                  15

Ile Lys Gln Arg Lys Ser
            20

<210> SEQ ID NO 163
<211> LENGTH: 24
<212> TYPE: PRT
<213> ORGANISM: Artificial
<220> FEATURE:
<223> OTHER INFORMATION: Synthetic peptide

<400> SEQUENCE: 163

Val Tyr Ser Phe Leu Tyr Val Leu Val Ile Val Arg Lys Leu Leu Ser
1               5                   10                  15

Met Lys Lys Arg Ile Glu Arg Leu
            20

<210> SEQ ID NO 164
<211> LENGTH: 18
<212> TYPE: PRT
<213> ORGANISM: Artificial
<220> FEATURE:
<223> OTHER INFORMATION: Synthetic peptide

<400> SEQUENCE: 164

Gly Ile Val Leu Ile Gly Leu Lys Leu Ile Pro Leu Leu Ala Asn Val
1               5                   10                  15

Leu Arg

<210> SEQ ID NO 165
<211> LENGTH: 21
<212> TYPE: PRT
<213> ORGANISM: Artificial
<220> FEATURE:
<223> OTHER INFORMATION: Synthetic peptide

<400> SEQUENCE: 165

Val Met Gln Ser Leu Tyr Val Lys Pro Pro Leu Ile Leu Val Thr Lys
1               5                   10                  15

Leu Ala Gln Gln Asn
            20

<210> SEQ ID NO 166
<211> LENGTH: 16
<212> TYPE: PRT
<213> ORGANISM: Artificial
<220> FEATURE:

<223> OTHER INFORMATION: Synthetic peptide

<400> SEQUENCE: 166

Ser Phe Met Pro Glu Ile Gln Lys Asn Thr Ile Pro Thr Gln Met Lys
1               5                   10                  15

<210> SEQ ID NO 167
<211> LENGTH: 39
<212> TYPE: PRT
<213> ORGANISM: Artificial
<220> FEATURE:
<223> OTHER INFORMATION: Synthetic peptide

<400> SEQUENCE: 167

Leu Gly Leu Thr Ala Gly Val Ala Tyr Ala Ala Gln Pro Thr Asn Gln
1               5                   10                  15

Pro Thr Asn Gln Pro Thr Asn Gln Pro Thr Asn Gln Pro Thr Asn Gln
            20                  25                  30

Pro Thr Asn Gln Pro Arg Trp
        35

<210> SEQ ID NO 168
<211> LENGTH: 15
<212> TYPE: PRT
<213> ORGANISM: Artificial
<220> FEATURE:
<223> OTHER INFORMATION: Synthetic peptide

<400> SEQUENCE: 168

Cys Gly Lys Leu Leu Glu Gln Lys Asn Phe Phe Leu Lys Thr Arg
1               5                   10                  15

<210> SEQ ID NO 169
<211> LENGTH: 30
<212> TYPE: PRT
<213> ORGANISM: Artificial
<220> FEATURE:
<223> OTHER INFORMATION: Synthetic peptide

<400> SEQUENCE: 169

Ala Ser Lys Gln Ala Ser Lys Gln Ala Ser Lys Gln Ala Ser Lys Gln
1               5                   10                  15

Ala Ser Lys Gln Ala Ser Arg Ser Leu Lys Asn His Leu Leu
            20                  25                  30

<210> SEQ ID NO 170
<211> LENGTH: 24
<212> TYPE: PRT
<213> ORGANISM: Artificial
<220> FEATURE:
<223> OTHER INFORMATION: Synthetic peptide

<400> SEQUENCE: 170

Pro Asp Ala Pro Arg Thr Cys Tyr His Lys Pro Ile Leu Ala Ala Leu
1               5                   10                  15

Ser Arg Ile Val Val Thr Asp Arg
            20

<210> SEQ ID NO 171
<211> LENGTH: 8
<212> TYPE: PRT
<213> ORGANISM: Artificial
<220> FEATURE:
<223> OTHER INFORMATION: Synthetic peptide

```
<400> SEQUENCE: 171

Asn Tyr Ala Val Val Ser His Thr
1               5

<210> SEQ ID NO 172
<211> LENGTH: 23
<212> TYPE: PRT
<213> ORGANISM: Artificial
<220> FEATURE:
<223> OTHER INFORMATION: Synthetic peptide

<400> SEQUENCE: 172

Phe Gln Lys Pro Phe Thr Gly Glu Glu Val Glu Asp Phe Gln Asp Asp
1               5                   10                  15

Asp Glu Ile Pro Thr Ile Ile
            20

<210> SEQ ID NO 173
<211> LENGTH: 15
<212> TYPE: PRT
<213> ORGANISM: Artificial
<220> FEATURE:
<223> OTHER INFORMATION: Synthetic peptide

<400> SEQUENCE: 173

Gly Trp Arg Leu Ile Lys Lys Ile Leu Arg Val Phe Lys Gly Leu
1               5                   10                  15

<210> SEQ ID NO 174
<211> LENGTH: 11
<212> TYPE: PRT
<213> ORGANISM: Artificial
<220> FEATURE:
<223> OTHER INFORMATION: Synthetic peptide

<400> SEQUENCE: 174

Phe Lys Lys Phe Trp Lys Trp Phe Arg Arg Phe
1               5                   10

<210> SEQ ID NO 175
<211> LENGTH: 11
<212> TYPE: PRT
<213> ORGANISM: Artificial
<220> FEATURE:
<223> OTHER INFORMATION: Synthetic peptide

<400> SEQUENCE: 175

Leu Lys Arg Phe Leu Lys Trp Phe Lys Arg Phe
1               5                   10

<210> SEQ ID NO 176
<211> LENGTH: 11
<212> TYPE: PRT
<213> ORGANISM: Artificial
<220> FEATURE:
<223> OTHER INFORMATION: Synthetic peptide

<400> SEQUENCE: 176

Lys Leu Phe Lys Arg Trp Lys His Leu Phe Arg
1               5                   10

<210> SEQ ID NO 177
<211> LENGTH: 11
<212> TYPE: PRT
<213> ORGANISM: Artificial
<220> FEATURE:
```

<223> OTHER INFORMATION: Synthetic peptide

<400> SEQUENCE: 177

Arg Leu Leu Lys Arg Phe Lys His Leu Phe Lys
1               5                   10

<210> SEQ ID NO 178
<211> LENGTH: 11
<212> TYPE: PRT
<213> ORGANISM: Artificial
<220> FEATURE:
<223> OTHER INFORMATION: Synthetic peptide

<400> SEQUENCE: 178

Phe Lys Thr Phe Leu Lys Trp Leu His Arg Phe
1               5                   10

<210> SEQ ID NO 179
<211> LENGTH: 11
<212> TYPE: PRT
<213> ORGANISM: Artificial
<220> FEATURE:
<223> OTHER INFORMATION: Synthetic peptide

<400> SEQUENCE: 179

Ile Lys Gln Leu Leu His Phe Phe Gln Arg Phe
1               5                   10

<210> SEQ ID NO 180
<211> LENGTH: 11
<212> TYPE: PRT
<213> ORGANISM: Artificial
<220> FEATURE:
<223> OTHER INFORMATION: Synthetic peptide

<400> SEQUENCE: 180

Lys Leu Leu Gln Thr Phe Lys Gln Ile Phe Arg
1               5                   10

<210> SEQ ID NO 181
<211> LENGTH: 11
<212> TYPE: PRT
<213> ORGANISM: Artificial
<220> FEATURE:
<223> OTHER INFORMATION: Synthetic peptide

<400> SEQUENCE: 181

Arg Ile Leu Lys Glu Leu Lys Asn Leu Phe Lys
1               5                   10

<210> SEQ ID NO 182
<211> LENGTH: 11
<212> TYPE: PRT
<213> ORGANISM: Artificial
<220> FEATURE:
<223> OTHER INFORMATION: Synthetic peptide

<400> SEQUENCE: 182

Leu Lys Gln Phe Val His Phe Ile His Arg Phe
1               5                   10

<210> SEQ ID NO 183
<211> LENGTH: 11
<212> TYPE: PRT
<213> ORGANISM: Artificial
<220> FEATURE:
<223> OTHER INFORMATION: Synthetic peptide

```
<400> SEQUENCE: 183

Val Lys Thr Leu Leu His Ile Phe Gln Arg Phe
1               5                   10

<210> SEQ ID NO 184
<211> LENGTH: 11
<212> TYPE: PRT
<213> ORGANISM: Artificial
<220> FEATURE:
<223> OTHER INFORMATION: Synthetic peptide

<400> SEQUENCE: 184

Lys Leu Val Glu Gln Leu Lys Glu Ile Phe Arg
1               5                   10

<210> SEQ ID NO 185
<211> LENGTH: 11
<212> TYPE: PRT
<213> ORGANISM: Artificial
<220> FEATURE:
<223> OTHER INFORMATION: Synthetic peptide

<400> SEQUENCE: 185

Arg Val Leu Gln Glu Ile Lys Gln Ile Leu Lys
1               5                   10

<210> SEQ ID NO 186
<211> LENGTH: 11
<212> TYPE: PRT
<213> ORGANISM: Artificial
<220> FEATURE:
<223> OTHER INFORMATION: Synthetic peptide

<400> SEQUENCE: 186

Val Lys Asn Leu Ala Glu Leu Val His Arg Phe
1               5                   10

<210> SEQ ID NO 187
<211> LENGTH: 11
<212> TYPE: PRT
<213> ORGANISM: Artificial
<220> FEATURE:
<223> OTHER INFORMATION: Synthetic peptide

<400> SEQUENCE: 187

Ala Thr His Leu Leu His Ala Leu Gln Arg Phe
1               5                   10

<210> SEQ ID NO 188
<211> LENGTH: 11
<212> TYPE: PRT
<213> ORGANISM: Artificial
<220> FEATURE:
<223> OTHER INFORMATION: Synthetic peptide

<400> SEQUENCE: 188

Lys Leu Ala Glu Asn Val Lys Glu Ile Leu Arg
1               5                   10

<210> SEQ ID NO 189
<211> LENGTH: 11
<212> TYPE: PRT
<213> ORGANISM: Artificial
<220> FEATURE:
<223> OTHER INFORMATION: Synthetic peptide
```

<400> SEQUENCE: 189

Arg Ala Leu His Glu Ala Lys Glu Ala Leu Lys
1               5                   10

<210> SEQ ID NO 190
<211> LENGTH: 11
<212> TYPE: PRT
<213> ORGANISM: Artificial
<220> FEATURE:
<223> OTHER INFORMATION: Synthetic peptide

<400> SEQUENCE: 190

Phe His Tyr Phe Trp His Trp Phe His Arg Phe
1               5                   10

<210> SEQ ID NO 191
<211> LENGTH: 11
<212> TYPE: PRT
<213> ORGANISM: Artificial
<220> FEATURE:
<223> OTHER INFORMATION: Synthetic peptide

<400> SEQUENCE: 191

Leu Tyr His Phe Leu His Trp Phe Gln Arg Phe
1               5                   10

<210> SEQ ID NO 192
<211> LENGTH: 11
<212> TYPE: PRT
<213> ORGANISM: Artificial
<220> FEATURE:
<223> OTHER INFORMATION: Synthetic peptide

<400> SEQUENCE: 192

Tyr Leu Phe Gln Thr Trp Gln His Leu Phe Arg
1               5                   10

<210> SEQ ID NO 193
<211> LENGTH: 11
<212> TYPE: PRT
<213> ORGANISM: Artificial
<220> FEATURE:
<223> OTHER INFORMATION: Synthetic peptide

<400> SEQUENCE: 193

Tyr Leu Leu Thr Glu Phe Gln His Leu Phe Lys
1               5                   10

<210> SEQ ID NO 194
<211> LENGTH: 11
<212> TYPE: PRT
<213> ORGANISM: Artificial
<220> FEATURE:
<223> OTHER INFORMATION: Synthetic peptide

<400> SEQUENCE: 194

Phe Lys Thr Phe Leu Gln Trp Leu His Arg Phe
1               5                   10

<210> SEQ ID NO 195
<211> LENGTH: 11
<212> TYPE: PRT
<213> ORGANISM: Artificial
<220> FEATURE:
<223> OTHER INFORMATION: Synthetic peptide

<400> SEQUENCE: 195

```
Ile Lys Thr Leu Leu His Phe Phe Gln Arg Phe
1               5                   10

<210> SEQ ID NO 196
<211> LENGTH: 11
<212> TYPE: PRT
<213> ORGANISM: Artificial
<220> FEATURE:
<223> OTHER INFORMATION: Synthetic peptide

<400> SEQUENCE: 196

Lys Leu Leu Gln Thr Phe Asn Gln Ile Phe Arg
1               5                   10

<210> SEQ ID NO 197
<211> LENGTH: 11
<212> TYPE: PRT
<213> ORGANISM: Artificial
<220> FEATURE:
<223> OTHER INFORMATION: Synthetic peptide

<400> SEQUENCE: 197

Thr Ile Leu Gln Ser Leu Lys Asn Ile Phe Lys
1               5                   10

<210> SEQ ID NO 198
<211> LENGTH: 11
<212> TYPE: PRT
<213> ORGANISM: Artificial
<220> FEATURE:
<223> OTHER INFORMATION: Synthetic peptide

<400> SEQUENCE: 198

Leu Lys Gln Phe Val Lys Phe Ile His Arg Phe
1               5                   10

<210> SEQ ID NO 199
<211> LENGTH: 11
<212> TYPE: PRT
<213> ORGANISM: Artificial
<220> FEATURE:
<223> OTHER INFORMATION: Synthetic peptide

<400> SEQUENCE: 199

Val Lys Gln Leu Leu Lys Ile Phe Asn Arg Phe
1               5                   10

<210> SEQ ID NO 200
<211> LENGTH: 11
<212> TYPE: PRT
<213> ORGANISM: Artificial
<220> FEATURE:
<223> OTHER INFORMATION: Synthetic peptide

<400> SEQUENCE: 200

Lys Leu Val Gln Gln Leu Lys Asn Ile Phe Arg
1               5                   10

<210> SEQ ID NO 201
<211> LENGTH: 11
<212> TYPE: PRT
<213> ORGANISM: Artificial
<220> FEATURE:
<223> OTHER INFORMATION: Synthetic peptide

<400> SEQUENCE: 201
```

Arg Val Leu Asn Gln Val Lys Gln Ile Leu Lys
1               5                   10

<210> SEQ ID NO 202
<211> LENGTH: 11
<212> TYPE: PRT
<213> ORGANISM: Artificial
<220> FEATURE:
<223> OTHER INFORMATION: Synthetic peptide

<400> SEQUENCE: 202

Val Lys Lys Leu Ala Lys Leu Val Arg Arg Phe
1               5                   10

<210> SEQ ID NO 203
<211> LENGTH: 11
<212> TYPE: PRT
<213> ORGANISM: Artificial
<220> FEATURE:
<223> OTHER INFORMATION: Synthetic peptide

<400> SEQUENCE: 203

Ala Lys Arg Leu Leu Lys Val Leu Lys Arg Phe
1               5                   10

<210> SEQ ID NO 204
<211> LENGTH: 11
<212> TYPE: PRT
<213> ORGANISM: Artificial
<220> FEATURE:
<223> OTHER INFORMATION: Synthetic peptide

<400> SEQUENCE: 204

Lys Leu Ala Gln Lys Val Lys Arg Val Leu Arg
1               5                   10

<210> SEQ ID NO 205
<211> LENGTH: 11
<212> TYPE: PRT
<213> ORGANISM: Artificial
<220> FEATURE:
<223> OTHER INFORMATION: Synthetic peptide

<400> SEQUENCE: 205

Arg Ala Leu Lys Arg Ile Lys His Val Leu Lys
1               5                   10

<210> SEQ ID NO 206
<211> LENGTH: 7
<212> TYPE: PRT
<213> ORGANISM: Artificial
<220> FEATURE:
<223> OTHER INFORMATION: Synthetic peptide

<400> SEQUENCE: 206

Arg Arg Arg Arg Trp Trp Trp
1               5

<210> SEQ ID NO 207
<211> LENGTH: 7
<212> TYPE: PRT
<213> ORGANISM: Artificial
<220> FEATURE:
<223> OTHER INFORMATION: Synthetic peptide

<400> SEQUENCE: 207

Arg Arg Trp Trp Arg Arg Trp

```
1               5

<210> SEQ ID NO 208
<211> LENGTH: 7
<212> TYPE: PRT
<213> ORGANISM: Artificial
<220> FEATURE:
<223> OTHER INFORMATION: Synthetic peptide

<400> SEQUENCE: 208

Arg Arg Arg Trp Trp Trp Arg
1               5

<210> SEQ ID NO 209
<211> LENGTH: 7
<212> TYPE: PRT
<213> ORGANISM: Artificial
<220> FEATURE:
<223> OTHER INFORMATION: Synthetic peptide

<400> SEQUENCE: 209

Arg Trp Arg Trp Arg Trp Arg
1               5

<210> SEQ ID NO 210
<211> LENGTH: 7
<212> TYPE: PRT
<213> ORGANISM: Artificial
<220> FEATURE:
<223> OTHER INFORMATION: Synthetic peptide

<400> SEQUENCE: 210

Arg Arg Arg Phe Trp Trp Arg
1               5

<210> SEQ ID NO 211
<211> LENGTH: 7
<212> TYPE: PRT
<213> ORGANISM: Artificial
<220> FEATURE:
<223> OTHER INFORMATION: Synthetic peptide

<400> SEQUENCE: 211

Arg Arg Trp Trp Arg Arg Phe
1               5

<210> SEQ ID NO 212
<211> LENGTH: 7
<212> TYPE: PRT
<213> ORGANISM: Artificial
<220> FEATURE:
<223> OTHER INFORMATION: Synthetic peptide

<400> SEQUENCE: 212

Arg Arg Arg Trp Trp Trp Phe
1               5

<210> SEQ ID NO 213
<211> LENGTH: 7
<212> TYPE: PRT
<213> ORGANISM: Artificial
<220> FEATURE:
<223> OTHER INFORMATION: Synthetic peptide

<400> SEQUENCE: 213

Arg Trp Arg Trp Arg Trp Phe
1               5
```

```
<210> SEQ ID NO 214
<211> LENGTH: 7
<212> TYPE: PRT
<213> ORGANISM: Artificial
<220> FEATURE:
<223> OTHER INFORMATION: Synthetic peptide

<400> SEQUENCE: 214

Arg Arg Arg Arg Trp Trp Lys
1               5

<210> SEQ ID NO 215
<211> LENGTH: 7
<212> TYPE: PRT
<213> ORGANISM: Artificial
<220> FEATURE:
<223> OTHER INFORMATION: Synthetic peptide

<400> SEQUENCE: 215

Arg Arg Trp Trp Arg Arg Lys
1               5

<210> SEQ ID NO 216
<211> LENGTH: 7
<212> TYPE: PRT
<213> ORGANISM: Artificial
<220> FEATURE:
<223> OTHER INFORMATION: Synthetic peptide

<400> SEQUENCE: 216

Arg Arg Arg Trp Trp Trp Lys
1               5

<210> SEQ ID NO 217
<211> LENGTH: 7
<212> TYPE: PRT
<213> ORGANISM: Artificial
<220> FEATURE:
<223> OTHER INFORMATION: Synthetic peptide

<400> SEQUENCE: 217

Arg Trp Arg Trp Arg Trp Lys
1               5

<210> SEQ ID NO 218
<211> LENGTH: 7
<212> TYPE: PRT
<213> ORGANISM: Artificial
<220> FEATURE:
<223> OTHER INFORMATION: Synthetic peptide

<400> SEQUENCE: 218

Arg Arg Arg Lys Trp Trp Lys
1               5

<210> SEQ ID NO 219
<211> LENGTH: 7
<212> TYPE: PRT
<213> ORGANISM: Artificial
<220> FEATURE:
<223> OTHER INFORMATION: Synthetic peptide

<400> SEQUENCE: 219

Arg Arg Trp Lys Arg Arg Lys
1               5
```

<210> SEQ ID NO 220
<211> LENGTH: 7
<212> TYPE: PRT
<213> ORGANISM: Artificial
<220> FEATURE:
<223> OTHER INFORMATION: Synthetic peptide

<400> SEQUENCE: 220

Arg Arg Arg Lys Trp Trp Lys
1               5

<210> SEQ ID NO 221
<211> LENGTH: 7
<212> TYPE: PRT
<213> ORGANISM: Artificial
<220> FEATURE:
<223> OTHER INFORMATION: Synthetic peptide

<400> SEQUENCE: 221

Arg Trp Arg Lys Arg Trp Lys
1               5

<210> SEQ ID NO 222
<211> LENGTH: 14
<212> TYPE: PRT
<213> ORGANISM: Artificial
<220> FEATURE:
<223> OTHER INFORMATION: Synthetic peptide

<400> SEQUENCE: 222

Leu His Leu Leu His Gln Leu Leu His Leu Leu His Gln Phe
1               5                   10

<210> SEQ ID NO 223
<211> LENGTH: 14
<212> TYPE: PRT
<213> ORGANISM: Artificial
<220> FEATURE:
<223> OTHER INFORMATION: Synthetic peptide

<400> SEQUENCE: 223

Ala Gln Ala Ala His Gln Ala Ala His Ala Ala His Gln Phe
1               5                   10

<210> SEQ ID NO 224
<211> LENGTH: 14
<212> TYPE: PRT
<213> ORGANISM: Artificial
<220> FEATURE:
<223> OTHER INFORMATION: Synthetic peptide

<400> SEQUENCE: 224

Lys Leu Lys Lys Leu Leu Lys Lys Leu Lys Lys Leu Leu Lys
1               5                   10

<210> SEQ ID NO 225
<211> LENGTH: 14
<212> TYPE: PRT
<213> ORGANISM: Artificial
<220> FEATURE:
<223> OTHER INFORMATION: Synthetic peptide

<400> SEQUENCE: 225

Leu Lys Leu Leu Lys Lys Leu Leu Lys Leu Leu Lys Lys Phe
1               5                   10

```
<210> SEQ ID NO 226
<211> LENGTH: 14
<212> TYPE: PRT
<213> ORGANISM: Artificial
<220> FEATURE:
<223> OTHER INFORMATION: Synthetic peptide

<400> SEQUENCE: 226

Leu Gln Leu Leu Lys Gln Leu Leu Lys Leu Leu Lys Gln Phe
1               5                   10

<210> SEQ ID NO 227
<211> LENGTH: 14
<212> TYPE: PRT
<213> ORGANISM: Artificial
<220> FEATURE:
<223> OTHER INFORMATION: Synthetic peptide

<400> SEQUENCE: 227

Ala Gln Ala Ala Lys Gln Ala Ala Lys Ala Ala Lys Gln Phe
1               5                   10

<210> SEQ ID NO 228
<211> LENGTH: 14
<212> TYPE: PRT
<213> ORGANISM: Artificial
<220> FEATURE:
<223> OTHER INFORMATION: Synthetic peptide

<400> SEQUENCE: 228

Arg Trp Arg Arg Trp Trp Arg His Phe His His Phe Phe His
1               5                   10

<210> SEQ ID NO 229
<211> LENGTH: 14
<212> TYPE: PRT
<213> ORGANISM: Artificial
<220> FEATURE:
<223> OTHER INFORMATION: Synthetic peptide

<400> SEQUENCE: 229

Lys Leu Lys Lys Leu Leu Lys Arg Trp Arg Arg Trp Trp Arg
1               5                   10

<210> SEQ ID NO 230
<211> LENGTH: 14
<212> TYPE: PRT
<213> ORGANISM: Artificial
<220> FEATURE:
<223> OTHER INFORMATION: Synthetic peptide

<400> SEQUENCE: 230

Arg Trp Arg Arg Leu Leu Lys Lys Leu His His Leu Leu His
1               5                   10

<210> SEQ ID NO 231
<211> LENGTH: 14
<212> TYPE: PRT
<213> ORGANISM: Artificial
<220> FEATURE:
<223> OTHER INFORMATION: Synthetic peptide

<400> SEQUENCE: 231

Lys Leu Lys Lys Leu Leu Lys His Leu His His Leu Leu His
1               5                   10

<210> SEQ ID NO 232
```

```
<211> LENGTH: 15
<212> TYPE: PRT
<213> ORGANISM: Artificial
<220> FEATURE:
<223> OTHER INFORMATION: Synthetic peptide

<400> SEQUENCE: 232

Phe Val Phe Arg His Lys Trp Val Trp Lys His Arg Phe Leu Phe
1               5                   10                  15

<210> SEQ ID NO 233
<211> LENGTH: 15
<212> TYPE: PRT
<213> ORGANISM: Artificial
<220> FEATURE:
<223> OTHER INFORMATION: Synthetic peptide

<400> SEQUENCE: 233

Val Phe Ile His Arg His Val Trp Val His Lys His Val Leu Phe
1               5                   10                  15

<210> SEQ ID NO 234
<211> LENGTH: 15
<212> TYPE: PRT
<213> ORGANISM: Artificial
<220> FEATURE:
<223> OTHER INFORMATION: Synthetic peptide

<400> SEQUENCE: 234

Trp Arg Trp Arg Ala Arg Trp Arg Trp Arg Leu Arg Trp Arg Phe
1               5                   10                  15

<210> SEQ ID NO 235
<211> LENGTH: 15
<212> TYPE: PRT
<213> ORGANISM: Artificial
<220> FEATURE:
<223> OTHER INFORMATION: Synthetic peptide

<400> SEQUENCE: 235

Trp Arg Ile His Leu Arg Ala Arg Leu His Val Lys Phe Arg Phe
1               5                   10                  15

<210> SEQ ID NO 236
<211> LENGTH: 15
<212> TYPE: PRT
<213> ORGANISM: Artificial
<220> FEATURE:
<223> OTHER INFORMATION: Synthetic peptide

<400> SEQUENCE: 236

Leu Arg Ile His Ala Arg Phe Lys Val His Ile Arg Leu Lys Phe
1               5                   10                  15

<210> SEQ ID NO 237
<211> LENGTH: 15
<212> TYPE: PRT
<213> ORGANISM: Artificial
<220> FEATURE:
<223> OTHER INFORMATION: Synthetic peptide

<400> SEQUENCE: 237

Phe His Ile Lys Phe Arg Val His Leu Lys Val Arg Phe His Phe
1               5                   10                  15

<210> SEQ ID NO 238
<211> LENGTH: 15
```

<212> TYPE: PRT
<213> ORGANISM: Artificial
<220> FEATURE:
<223> OTHER INFORMATION: Synthetic peptide

<400> SEQUENCE: 238

Phe His Val Lys Ile His Phe Arg Leu His Val Lys Phe His Phe
1               5                   10                  15

<210> SEQ ID NO 239
<211> LENGTH: 15
<212> TYPE: PRT
<213> ORGANISM: Artificial
<220> FEATURE:
<223> OTHER INFORMATION: Synthetic peptide

<400> SEQUENCE: 239

Leu His Ile His Ala His Phe His Val His Ile His Leu His Phe
1               5                   10                  15

<210> SEQ ID NO 240
<211> LENGTH: 15
<212> TYPE: PRT
<213> ORGANISM: Artificial
<220> FEATURE:
<223> OTHER INFORMATION: Synthetic peptide

<400> SEQUENCE: 240

Phe Lys Ile His Phe Arg Leu Lys Val His Ile Arg Phe Lys Phe
1               5                   10                  15

<210> SEQ ID NO 241
<211> LENGTH: 15
<212> TYPE: PRT
<213> ORGANISM: Artificial
<220> FEATURE:
<223> OTHER INFORMATION: Synthetic peptide

<400> SEQUENCE: 241

Phe Lys Ala His Ile Arg Phe Lys Leu Arg Val Lys Phe His Phe
1               5                   10                  15

<210> SEQ ID NO 242
<211> LENGTH: 15
<212> TYPE: PRT
<213> ORGANISM: Artificial
<220> FEATURE:
<223> OTHER INFORMATION: Synthetic peptide

<400> SEQUENCE: 242

Leu Lys Ala Lys Ile Lys Phe Lys Val Lys Leu Lys Ile Lys Phe
1               5                   10                  15

<210> SEQ ID NO 243
<211> LENGTH: 14
<212> TYPE: PRT
<213> ORGANISM: Artificial
<220> FEATURE:
<223> OTHER INFORMATION: Synthetic peptide

<400> SEQUENCE: 243

Trp Ile Trp Lys His Lys Phe Leu His Arg His Phe Leu Phe
1               5                   10

<210> SEQ ID NO 244
<211> LENGTH: 14
<212> TYPE: PRT

```
<213> ORGANISM: Artificial
<220> FEATURE:
<223> OTHER INFORMATION: Synthetic peptide

<400> SEQUENCE: 244

Val Phe Leu His Arg His Val Ile Lys His Lys Leu Val Phe
1               5                   10

<210> SEQ ID NO 245
<211> LENGTH: 13
<212> TYPE: PRT
<213> ORGANISM: Artificial
<220> FEATURE:
<223> OTHER INFORMATION: Synthetic peptide

<400> SEQUENCE: 245

Phe Leu His Lys His Val Leu Arg His Arg Ile Val Phe
1               5                   10

<210> SEQ ID NO 246
<211> LENGTH: 13
<212> TYPE: PRT
<213> ORGANISM: Artificial
<220> FEATURE:
<223> OTHER INFORMATION: Synthetic peptide

<400> SEQUENCE: 246

Val Phe Lys His Lys Ile Val His Arg His Ile Leu Phe
1               5                   10

<210> SEQ ID NO 247
<211> LENGTH: 13
<212> TYPE: PRT
<213> ORGANISM: Artificial
<220> FEATURE:
<223> OTHER INFORMATION: Synthetic peptide

<400> SEQUENCE: 247

Phe Leu Phe Lys His Leu Phe Leu His Arg Ile Phe Phe
1               5                   10

<210> SEQ ID NO 248
<211> LENGTH: 12
<212> TYPE: PRT
<213> ORGANISM: Artificial
<220> FEATURE:
<223> OTHER INFORMATION: Synthetic peptide

<400> SEQUENCE: 248

Leu Phe Lys His Ile Leu Ile His Arg Val Ile Phe
1               5                   10

<210> SEQ ID NO 249
<211> LENGTH: 12
<212> TYPE: PRT
<213> ORGANISM: Artificial
<220> FEATURE:
<223> OTHER INFORMATION: Synthetic peptide

<400> SEQUENCE: 249

Phe Leu His Lys His Leu Phe Lys His Lys Leu Phe
1               5                   10

<210> SEQ ID NO 250
<211> LENGTH: 12
<212> TYPE: PRT
<213> ORGANISM: Artificial
```

```
<220> FEATURE:
<223> OTHER INFORMATION: Synthetic peptide

<400> SEQUENCE: 250

Val Phe Arg His Arg Phe Ile His Arg His Val Phe
1               5                   10

<210> SEQ ID NO 251
<211> LENGTH: 12
<212> TYPE: PRT
<213> ORGANISM: Artificial
<220> FEATURE:
<223> OTHER INFORMATION: Synthetic peptide

<400> SEQUENCE: 251

Phe Ile His Lys Leu Val His Lys His Val Leu Phe
1               5                   10

<210> SEQ ID NO 252
<211> LENGTH: 12
<212> TYPE: PRT
<213> ORGANISM: Artificial
<220> FEATURE:
<223> OTHER INFORMATION: Synthetic peptide

<400> SEQUENCE: 252

Val Leu Arg His Leu Phe Arg His Arg Ile Val Phe
1               5                   10

<210> SEQ ID NO 253
<211> LENGTH: 12
<212> TYPE: PRT
<213> ORGANISM: Artificial
<220> FEATURE:
<223> OTHER INFORMATION: Synthetic peptide

<400> SEQUENCE: 253

Leu Val His Lys Leu Ile Leu Arg His Leu Leu Phe
1               5                   10

<210> SEQ ID NO 254
<211> LENGTH: 12
<212> TYPE: PRT
<213> ORGANISM: Artificial
<220> FEATURE:
<223> OTHER INFORMATION: Synthetic peptide

<400> SEQUENCE: 254

Val Phe Lys Arg Val Leu Ile His Lys Leu Ile Phe
1               5                   10

<210> SEQ ID NO 255
<211> LENGTH: 12
<212> TYPE: PRT
<213> ORGANISM: Artificial
<220> FEATURE:
<223> OTHER INFORMATION: Synthetic peptide

<400> SEQUENCE: 255

Ile Val Arg Lys Phe Leu Phe Arg His Lys Val Phe
1               5                   10

<210> SEQ ID NO 256
<211> LENGTH: 12
<212> TYPE: PRT
<213> ORGANISM: Artificial
<220> FEATURE:
```

<223> OTHER INFORMATION: Synthetic peptide

<400> SEQUENCE: 256

Val Leu Lys His Val Ile Ala His Lys Arg Leu Phe
1               5                   10

<210> SEQ ID NO 257
<211> LENGTH: 11
<212> TYPE: PRT
<213> ORGANISM: Artificial
<220> FEATURE:
<223> OTHER INFORMATION: Synthetic peptide

<400> SEQUENCE: 257

Phe Ile Arg Lys Phe Leu Phe Lys His Leu Phe
1               5                   10

<210> SEQ ID NO 258
<211> LENGTH: 11
<212> TYPE: PRT
<213> ORGANISM: Artificial
<220> FEATURE:
<223> OTHER INFORMATION: Synthetic peptide

<400> SEQUENCE: 258

Val Ile Arg His Val Trp Val Arg Lys Leu Phe
1               5                   10

<210> SEQ ID NO 259
<211> LENGTH: 13
<212> TYPE: PRT
<213> ORGANISM: Artificial
<220> FEATURE:
<223> OTHER INFORMATION: Synthetic peptide

<400> SEQUENCE: 259

Phe Leu Phe Arg His Arg Phe Arg His Arg Leu Val Phe
1               5                   10

<210> SEQ ID NO 260
<211> LENGTH: 13
<212> TYPE: PRT
<213> ORGANISM: Artificial
<220> FEATURE:
<223> OTHER INFORMATION: Synthetic peptide

<400> SEQUENCE: 260

Leu Phe Leu His Lys His Ala Lys His Lys Phe Leu Phe
1               5                   10

<210> SEQ ID NO 261
<211> LENGTH: 11
<212> TYPE: PRT
<213> ORGANISM: Artificial
<220> FEATURE:
<223> OTHER INFORMATION: Synthetic peptide

<400> SEQUENCE: 261

Phe Lys His Lys Phe Lys His Lys Phe Ile Phe
1               5                   10

<210> SEQ ID NO 262
<211> LENGTH: 11
<212> TYPE: PRT
<213> ORGANISM: Artificial
<220> FEATURE:
<223> OTHER INFORMATION: Synthetic peptide

<400> SEQUENCE: 262

Leu Arg His Arg Leu Arg His Arg Leu Ile Phe
1               5                   10

<210> SEQ ID NO 263
<211> LENGTH: 11
<212> TYPE: PRT
<213> ORGANISM: Artificial
<220> FEATURE:
<223> OTHER INFORMATION: Synthetic peptide

<400> SEQUENCE: 263

Leu Ile Leu Lys Phe Leu Phe Lys Phe Val Phe
1               5                   10

<210> SEQ ID NO 264
<211> LENGTH: 11
<212> TYPE: PRT
<213> ORGANISM: Artificial
<220> FEATURE:
<223> OTHER INFORMATION: Synthetic peptide

<400> SEQUENCE: 264

Val Leu Ile Arg Ile Leu Val Arg Val Ile Phe
1               5                   10

<210> SEQ ID NO 265
<211> LENGTH: 9
<212> TYPE: PRT
<213> ORGANISM: Artificial
<220> FEATURE:
<223> OTHER INFORMATION: Synthetic peptide

<400> SEQUENCE: 265

Phe Arg His Arg Phe Arg His Arg Phe
1               5

<210> SEQ ID NO 266
<211> LENGTH: 9
<212> TYPE: PRT
<213> ORGANISM: Artificial
<220> FEATURE:
<223> OTHER INFORMATION: Synthetic peptide

<400> SEQUENCE: 266

Leu Lys His Lys Leu Lys His Lys Phe
1               5

<210> SEQ ID NO 267
<211> LENGTH: 9
<212> TYPE: PRT
<213> ORGANISM: Artificial
<220> FEATURE:
<223> OTHER INFORMATION: Synthetic peptide

<400> SEQUENCE: 267

Phe Lys Phe Lys His Lys Leu Ile Phe
1               5

<210> SEQ ID NO 268
<211> LENGTH: 9
<212> TYPE: PRT
<213> ORGANISM: Artificial
<220> FEATURE:
<223> OTHER INFORMATION: Synthetic peptide

```
<400> SEQUENCE: 268

Leu Arg Leu Arg His Arg Val Leu Phe
1               5

<210> SEQ ID NO 269
<211> LENGTH: 9
<212> TYPE: PRT
<213> ORGANISM: Artificial
<220> FEATURE:
<223> OTHER INFORMATION: Synthetic peptide

<400> SEQUENCE: 269

Phe Lys Phe Leu Phe Lys Phe Leu Phe
1               5

<210> SEQ ID NO 270
<211> LENGTH: 9
<212> TYPE: PRT
<213> ORGANISM: Artificial
<220> FEATURE:
<223> OTHER INFORMATION: Synthetic peptide

<400> SEQUENCE: 270

Leu Arg Leu Phe Leu Arg Trp Leu Phe
1               5

<210> SEQ ID NO 271
<211> LENGTH: 9
<212> TYPE: PRT
<213> ORGANISM: Artificial
<220> FEATURE:
<223> OTHER INFORMATION: Synthetic peptide

<400> SEQUENCE: 271

Phe Lys Phe Leu Phe Lys His Lys Phe
1               5

<210> SEQ ID NO 272
<211> LENGTH: 9
<212> TYPE: PRT
<213> ORGANISM: Artificial
<220> FEATURE:
<223> OTHER INFORMATION: Synthetic peptide

<400> SEQUENCE: 272

Leu Arg Leu Phe Leu Arg His Arg Phe
1               5

<210> SEQ ID NO 273
<211> LENGTH: 7
<212> TYPE: PRT
<213> ORGANISM: Artificial
<220> FEATURE:
<223> OTHER INFORMATION: Synthetic peptide

<400> SEQUENCE: 273

Phe Lys Phe Leu Phe Lys Phe
1               5

<210> SEQ ID NO 274
<211> LENGTH: 7
<212> TYPE: PRT
<213> ORGANISM: Artificial
<220> FEATURE:
<223> OTHER INFORMATION: Synthetic peptide

<400> SEQUENCE: 274
```

```
Leu Arg Leu Phe Leu Arg Phe
1               5

<210> SEQ ID NO 275
<211> LENGTH: 14
<212> TYPE: PRT
<213> ORGANISM: Artificial
<220> FEATURE:
<223> OTHER INFORMATION: Synthetic peptide

<400> SEQUENCE: 275

His His Phe Phe His His Phe His His Phe Phe His His Phe
1               5                   10

<210> SEQ ID NO 276
<211> LENGTH: 14
<212> TYPE: PRT
<213> ORGANISM: Artificial
<220> FEATURE:
<223> OTHER INFORMATION: Synthetic peptide

<400> SEQUENCE: 276

Phe His Phe Phe His His Phe Phe His Phe Phe His His Phe
1               5                   10

<210> SEQ ID NO 277
<211> LENGTH: 21
<212> TYPE: PRT
<213> ORGANISM: Artificial
<220> FEATURE:
<223> OTHER INFORMATION: Synthetic peptide

<400> SEQUENCE: 277

Lys Leu Leu Lys Gly Ala Thr Phe His Phe Phe His His Phe Phe His
1               5                   10                  15

Phe Phe His His Phe
            20

<210> SEQ ID NO 278
<211> LENGTH: 18
<212> TYPE: PRT
<213> ORGANISM: Artificial
<220> FEATURE:
<223> OTHER INFORMATION: Synthetic peptide

<400> SEQUENCE: 278

Lys Leu Leu Lys Phe His Phe Phe His His Phe Phe His Phe Phe His
1               5                   10                  15

His Phe

<210> SEQ ID NO 279
<211> LENGTH: 18
<212> TYPE: PRT
<213> ORGANISM: Artificial
<220> FEATURE:
<223> OTHER INFORMATION: Synthetic peptide

<400> SEQUENCE: 279

Phe His Phe Phe His His Phe Phe His Phe Phe His His Phe Lys Leu
1               5                   10                  15

Leu Lys

<210> SEQ ID NO 280
<211> LENGTH: 7
```

```
<212> TYPE: PRT
<213> ORGANISM: Artificial
<220> FEATURE:
<223> OTHER INFORMATION: Synthetic peptide

<400> SEQUENCE: 280

Tyr Ser Pro Trp Thr Asn Phe
1               5

<210> SEQ ID NO 281
<211> LENGTH: 37
<212> TYPE: PRT
<213> ORGANISM: Artificial
<220> FEATURE:
<223> OTHER INFORMATION: Synthetic peptide

<400> SEQUENCE: 281

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 282
<211> LENGTH: 38
<212> TYPE: PRT
<213> ORGANISM: Artificial
<220> FEATURE:
<223> OTHER INFORMATION: Synthetic peptide

<400> SEQUENCE: 282

Cys Leu Leu Gly Asp Phe Phe Arg Lys Ser Lys Glu Lys Ile Gly Lys
1               5                   10                  15

Glu Phe Lys Arg Ile Val Gln Arg Ile Lys Asp Phe Leu Arg Asn Leu
            20                  25                  30

Val Pro Arg Thr Glu Ser
        35

<210> SEQ ID NO 283
<211> LENGTH: 16
<212> TYPE: PRT
<213> ORGANISM: Artificial
<220> FEATURE:
<223> OTHER INFORMATION: Synthetic peptide

<400> SEQUENCE: 283

Phe Lys Arg Ile Val Gln Arg Ile Lys Asp Phe Leu Arg Asn Leu Val
1               5                   10                  15

<210> SEQ ID NO 284
<211> LENGTH: 39
<212> TYPE: PRT
<213> ORGANISM: Artificial
<220> FEATURE:
<223> OTHER INFORMATION: Synthetic peptide

<400> SEQUENCE: 284

Cys Leu Leu Gly Asp Phe Phe Arg Lys Ser Lys Glu Lys Ile Gly Lys
1               5                   10                  15

Glu Phe Lys Arg Ile Val Gln Arg Ile Lys Asp Phe Leu Arg Asn Leu
            20                  25                  30

Val Pro Arg Thr Glu Ser Cys
        35
```

```
<210> SEQ ID NO 285
<211> LENGTH: 13
<212> TYPE: PRT
<213> ORGANISM: Artificial
<220> FEATURE:
<223> OTHER INFORMATION: Synthetic peptide

<400> SEQUENCE: 285

Phe Lys Arg Ile Val Gln Arg Ile Lys Asp Phe Leu Arg
1               5                   10

<210> SEQ ID NO 286
<211> LENGTH: 21
<212> TYPE: PRT
<213> ORGANISM: Artificial
<220> FEATURE:
<223> OTHER INFORMATION: Synthetic peptide

<400> SEQUENCE: 286

Phe Lys Arg Ile Val Gln Arg Ile Lys Asp Phe Leu Arg Asn Leu Val
1               5                   10                  15

Pro Arg Thr Glu Ser
            20

<210> SEQ ID NO 287
<211> LENGTH: 21
<212> TYPE: PRT
<213> ORGANISM: Artificial
<220> FEATURE:
<223> OTHER INFORMATION: Synthetic peptide

<400> SEQUENCE: 287

Gly Lys Glu Phe Lys Arg Ile Val Gln Arg Ile Lys Asp Phe Leu Arg
1               5                   10                  15

Asn Leu Val Pro Arg
            20

<210> SEQ ID NO 288
<211> LENGTH: 20
<212> TYPE: PRT
<213> ORGANISM: Artificial
<220> FEATURE:
<223> OTHER INFORMATION: Synthetic peptide

<400> SEQUENCE: 288

Lys Arg Ile Val Gln Arg Ile Lys Asp Phe Leu Arg Asn Leu Val Pro
1               5                   10                  15

Arg Thr Glu Ser
            20

<210> SEQ ID NO 289
<211> LENGTH: 21
<212> TYPE: PRT
<213> ORGANISM: Artificial
<220> FEATURE:
<223> OTHER INFORMATION: Synthetic peptide

<400> SEQUENCE: 289

Leu Leu Gly Asp Phe Phe Arg Lys Ser Lys Glu Lys Ile Gly Lys Glu
1               5                   10                  15

Phe Lys Arg Ile Val
            20
```

```
<210> SEQ ID NO 290
<211> LENGTH: 31
<212> TYPE: PRT
<213> ORGANISM: Artificial
<220> FEATURE:
<223> OTHER INFORMATION: Synthetic peptide

<400> SEQUENCE: 290

Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro Arg Thr Glu Ser
            20                  25                  30

<210> SEQ ID NO 291
<211> LENGTH: 21
<212> TYPE: PRT
<213> ORGANISM: Artificial
<220> FEATURE:
<223> OTHER INFORMATION: Synthetic peptide

<400> SEQUENCE: 291

Ser Lys Glu Lys Ile Gly Lys Glu Phe Lys Arg Ile Val Gln Arg Ile
1               5                   10                  15

Lys Asp Phe Leu Arg
            20

<210> SEQ ID NO 292
<211> LENGTH: 38
<212> TYPE: PRT
<213> ORGANISM: Artificial
<220> FEATURE:
<223> OTHER INFORMATION: Synthetic peptide

<400> SEQUENCE: 292

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Cys
        35

<210> SEQ ID NO 293
<211> LENGTH: 11
<212> TYPE: PRT
<213> ORGANISM: Artificial
<220> FEATURE:
<223> OTHER INFORMATION: Synthetic peptide

<400> SEQUENCE: 293

Lys Leu Phe Lys Phe Leu Arg Lys His Leu Leu
1               5                   10

<210> SEQ ID NO 294
<211> LENGTH: 13
<212> TYPE: PRT
<213> ORGANISM: Artificial
<220> FEATURE:
<223> OTHER INFORMATION: Synthetic peptide

<400> SEQUENCE: 294

Phe Leu Lys Phe Leu Lys Lys Phe Phe Lys Lys Leu Lys
1               5                   10

<210> SEQ ID NO 295
<211> LENGTH: 16
```

```
<212> TYPE: PRT
<213> ORGANISM: Artificial
<220> FEATURE:
<223> OTHER INFORMATION: Synthetic peptide

<400> SEQUENCE: 295

Phe Ile Gly Ala Ile Ala Arg Leu Leu Ser Lys Ile Phe Gly Lys Arg
1               5                   10                  15

<210> SEQ ID NO 296
<211> LENGTH: 18
<212> TYPE: PRT
<213> ORGANISM: Artificial
<220> FEATURE:
<223> OTHER INFORMATION: Synthetic peptide

<400> SEQUENCE: 296

Gly Ile Phe Ser Lys Leu Ala Gly Lys Lys Ile Lys Asn Leu Leu Ile
1               5                   10                  15

Ser Gly

<210> SEQ ID NO 297
<211> LENGTH: 21
<212> TYPE: PRT
<213> ORGANISM: Artificial
<220> FEATURE:
<223> OTHER INFORMATION: Synthetic peptide

<400> SEQUENCE: 297

Gly Ile Phe Ser Lys Leu Ala Gly Lys Lys Ile Lys Asn Leu Leu Ile
1               5                   10                  15

Ser Gly Leu Lys Gly
            20

<210> SEQ ID NO 298
<211> LENGTH: 20
<212> TYPE: PRT
<213> ORGANISM: Artificial
<220> FEATURE:
<223> OTHER INFORMATION: Synthetic peptide

<400> SEQUENCE: 298

Gly Leu Phe Ser Lys Phe Val Gly Lys Gly Ile Lys Asn Phe Leu Ile
1               5                   10                  15

Lys Gly Val Lys
            20

<210> SEQ ID NO 299
<211> LENGTH: 19
<212> TYPE: PRT
<213> ORGANISM: Artificial
<220> FEATURE:
<223> OTHER INFORMATION: Synthetic peptide

<400> SEQUENCE: 299

Lys Ala Tyr Ser Thr Pro Arg Cys Lys Gly Leu Phe Arg Ala Leu Met
1               5                   10                  15

Cys Trp Leu

<210> SEQ ID NO 300
<211> LENGTH: 19
<212> TYPE: PRT
<213> ORGANISM: Artificial
<220> FEATURE:
<223> OTHER INFORMATION: Synthetic peptide
```

-continued

<400> SEQUENCE: 300

Lys Ile Phe Gly Ala Ile Trp Pro Leu Ala Leu Gly Ala Leu Lys Asn
1               5                   10                  15

Leu Ile Lys

<210> SEQ ID NO 301
<211> LENGTH: 25
<212> TYPE: PRT
<213> ORGANISM: Artificial
<220> FEATURE:
<223> OTHER INFORMATION: Synthetic peptide

<400> SEQUENCE: 301

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 302
<211> LENGTH: 18
<212> TYPE: PRT
<213> ORGANISM: Artificial
<220> FEATURE:
<223> OTHER INFORMATION: Synthetic peptide

<400> SEQUENCE: 302

Arg Gly Leu Arg Arg Leu Gly Arg Lys Ile Ala His Gly Val Lys Lys
1               5                   10                  15

Tyr Gly

<210> SEQ ID NO 303
<211> LENGTH: 29
<212> TYPE: PRT
<213> ORGANISM: Artificial
<220> FEATURE:
<223> OTHER INFORMATION: Synthetic peptide

<400> SEQUENCE: 303

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 304
<211> LENGTH: 18
<212> TYPE: PRT
<213> ORGANISM: Artificial
<220> FEATURE:
<223> OTHER INFORMATION: Synthetic peptide

<400> SEQUENCE: 304

Lys Ile Ala His Gly Val Lys Lys Tyr Gly Pro Thr Val Leu Arg Ile
1               5                   10                  15

Ile Arg

<210> SEQ ID NO 305
<211> LENGTH: 37
<212> TYPE: PRT
<213> ORGANISM: Artificial
<220> FEATURE:
<223> OTHER INFORMATION: Synthetic peptide

<400> SEQUENCE: 305

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 306
<211> LENGTH: 13
<212> TYPE: PRT
<213> ORGANISM: Artificial
<220> FEATURE:
<223> OTHER INFORMATION: Synthetic peptide

<400> SEQUENCE: 306

Phe Leu Pro Leu Ile Gly Arg Val Leu Ser Gly Ile Leu
1               5                   10

<210> SEQ ID NO 307
<211> LENGTH: 21
<212> TYPE: PRT
<213> ORGANISM: Artificial
<220> FEATURE:
<223> OTHER INFORMATION: Synthetic peptide

<400> SEQUENCE: 307

Ile Gly Lys Phe Leu Lys Lys Ala Lys Lys Phe Gly Lys Ala Phe Val
1               5                   10                  15

Lys Ile Leu Lys Lys
            20

<210> SEQ ID NO 308
<211> LENGTH: 18
<212> TYPE: PRT
<213> ORGANISM: Artificial
<220> FEATURE:
<223> OTHER INFORMATION: Synthetic peptide

<400> SEQUENCE: 308

Gly Lys Phe Leu Lys Lys Ala Lys Lys Phe Gly Lys Ala Phe Val Lys
1               5                   10                  15

Ile Leu

<210> SEQ ID NO 309
<211> LENGTH: 15
<212> TYPE: PRT
<213> ORGANISM: Artificial
<220> FEATURE:
<223> OTHER INFORMATION: Synthetic peptide

<400> SEQUENCE: 309

Trp Phe Leu Lys Phe Leu Lys Lys Phe Phe Lys Lys Leu Lys Tyr
1               5                   10                  15

<210> SEQ ID NO 310
<211> LENGTH: 17
<212> TYPE: PRT
<213> ORGANISM: Artificial
<220> FEATURE:
<223> OTHER INFORMATION: Synthetic peptide

<400> SEQUENCE: 310

Arg Gly Leu Arg Arg Leu Gly Arg Lys Ile Ala His Gly Val Lys Lys
1               5                   10                  15
```

Tyr

<210> SEQ ID NO 311
<211> LENGTH: 13
<212> TYPE: PRT
<213> ORGANISM: Artificial
<220> FEATURE:
<223> OTHER INFORMATION: Synthetic peptide

<400> SEQUENCE: 311

Leu Leu Gly Asp Phe Phe Arg Lys Ser Lys Glu Lys Ile
1               5                   10

<210> SEQ ID NO 312
<211> LENGTH: 12
<212> TYPE: PRT
<213> ORGANISM: Artificial
<220> FEATURE:
<223> OTHER INFORMATION: Synthetic peptide

<400> SEQUENCE: 312

Ile Leu Arg Trp Pro Trp Trp Pro Trp Arg Arg Lys
1               5                   10

<210> SEQ ID NO 313
<211> LENGTH: 19
<212> TYPE: PRT
<213> ORGANISM: Artificial
<220> FEATURE:
<223> OTHER INFORMATION: Synthetic peptide

<400> SEQUENCE: 313

Lys Leu Phe Gly Ala Leu Trp Pro Leu Ala Leu Gly Ala Leu Lys Asn
1               5                   10                  15

Leu Leu Lys

<210> SEQ ID NO 314
<211> LENGTH: 16
<212> TYPE: PRT
<213> ORGANISM: Artificial
<220> FEATURE:
<223> OTHER INFORMATION: Synthetic peptide

<400> SEQUENCE: 314

Lys Asn Leu Arg Ile Ile Arg Lys Gly Ile His Ile Ile Lys Lys Tyr
1               5                   10                  15

<210> SEQ ID NO 315
<211> LENGTH: 5
<212> TYPE: PRT
<213> ORGANISM: Artificial
<220> FEATURE:
<223> OTHER INFORMATION: Synthetic peptide linker

<400> SEQUENCE: 315

Pro Ser Gly Ser Pro
1               5

<210> SEQ ID NO 316
<211> LENGTH: 5
<212> TYPE: PRT
<213> ORGANISM: Artificial
<220> FEATURE:
<223> OTHER INFORMATION: Synthetic peptide linker

<400> SEQUENCE: 316

Ala Ser Ala Ser Ala
1               5

<210> SEQ ID NO 317
<211> LENGTH: 15
<212> TYPE: PRT
<213> ORGANISM: Artificial
<220> FEATURE:
<223> OTHER INFORMATION: Synthetic peptide linker

<400> SEQUENCE: 317

Gly Gly Gly Gly Ser Gly Gly Gly Ser Gly Gly Gly Ser
1               5                   10                  15

<210> SEQ ID NO 318
<211> LENGTH: 4
<212> TYPE: PRT
<213> ORGANISM: Artificial
<220> FEATURE:
<223> OTHER INFORMATION: Synthetic peptide linker

<400> SEQUENCE: 318

Gly Gly Gly Gly
1

<210> SEQ ID NO 319
<211> LENGTH: 5
<212> TYPE: PRT
<213> ORGANISM: Artificial
<220> FEATURE:
<223> OTHER INFORMATION: Synthetic peptide linker

<400> SEQUENCE: 319

Pro Ser Pro Ser Pro
1               5

<210> SEQ ID NO 320
<211> LENGTH: 5
<212> TYPE: PRT
<213> ORGANISM: Artificial
<220> FEATURE:
<223> OTHER INFORMATION: Synthetic peptide linker

<400> SEQUENCE: 320

Pro Ser Pro Ser Pro
1               5

<210> SEQ ID NO 321
<211> LENGTH: 4
<212> TYPE: PRT
<213> ORGANISM: Artificial
<220> FEATURE:
<223> OTHER INFORMATION: Synthetic peptide linker

<400> SEQUENCE: 321

Lys Lys Lys Lys
1

<210> SEQ ID NO 322
<211> LENGTH: 4
<212> TYPE: PRT
<213> ORGANISM: Artificial
<220> FEATURE:
<223> OTHER INFORMATION: Synthetic peptide linker

<400> SEQUENCE: 322

Arg Arg Arg Arg
1

<210> SEQ ID NO 323
<211> LENGTH: 5
<212> TYPE: PRT
<213> ORGANISM: Artificial
<220> FEATURE:
<223> OTHER INFORMATION: Synthetic peptide linker

<400> SEQUENCE: 323

Ala Ser Ala Ser Ala
1               5

<210> SEQ ID NO 324
<211> LENGTH: 6
<212> TYPE: PRT
<213> ORGANISM: Artificial
<220> FEATURE:
<223> OTHER INFORMATION: Synthetic peptide linker

<400> SEQUENCE: 324

Gly Gly Ser Gly Gly Ser
1               5

<210> SEQ ID NO 325
<211> LENGTH: 5
<212> TYPE: PRT
<213> ORGANISM: Artificial
<220> FEATURE:
<223> OTHER INFORMATION: Synthetic peptide linker

<400> SEQUENCE: 325

Gly Gly Gly Gly Ser
1               5

<210> SEQ ID NO 326
<211> LENGTH: 10
<212> TYPE: PRT
<213> ORGANISM: Artificial
<220> FEATURE:
<223> OTHER INFORMATION: Synthetic peptide linker

<400> SEQUENCE: 326

Gly Gly Gly Gly Ser Gly Gly Gly Gly Ser
1               5                   10

<210> SEQ ID NO 327
<211> LENGTH: 15
<212> TYPE: PRT
<213> ORGANISM: Artificial
<220> FEATURE:
<223> OTHER INFORMATION: Synthetic peptide linker

<400> SEQUENCE: 327

Gly Gly Gly Gly Ser Gly Gly Gly Gly Ser Gly Gly Gly Gly Ser
1               5                   10                  15

<210> SEQ ID NO 328
<211> LENGTH: 20
<212> TYPE: PRT
<213> ORGANISM: Artificial
<220> FEATURE:
<223> OTHER INFORMATION: Synthetic peptide linker

<400> SEQUENCE: 328

Gly Gly Gly Gly Ser Gly Gly Gly Gly Ser Gly Gly Gly Gly Ser Gly

```
1               5                   10                  15
Gly Gly Gly Ser
            20

<210> SEQ ID NO 329
<211> LENGTH: 25
<212> TYPE: PRT
<213> ORGANISM: Artificial
<220> FEATURE:
<223> OTHER INFORMATION: Synthetic peptide linker

<400> SEQUENCE: 329

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 330
<211> LENGTH: 30
<212> TYPE: PRT
<213> ORGANISM: Artificial
<220> FEATURE:
<223> OTHER INFORMATION: Synthetic peptide linker

<400> SEQUENCE: 330

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

DENTAL VARNISHES THAT RELEASE SPECIFICALLY TARGETED ANTIMICROBIAL PEPTIDES AND/OR FLUORIDE

CROSS-REFERENCE TO RELATED APPLICATIONS

This application is a U.S. 371 National Phase of PCT/US2018/027350, filed on Apr. 12, 2018, which claims benefit of and priority to U.S. Ser. No. 62/485,787, filed on Apr. 14, 2017, both of which are incorporated herein by reference in their entirety for all purposes.

INCORPORATION BY REFERENCE OF SEQUENCE LISTING PROVIDED AS A TEXT FILE

A Sequence Listing is provided herewith as a text file, "C3JNP026US ST25.txt" created on Mar. 8, 2020 and having a size of 77.9 kb. The contents of the text file are incorporated by reference herein in their entirety.

BACKGROUND

Fluoride dental varnishes provide a highly concentrated form of fluoride that can be applied to a tooth surface, by a dentist, dental hygienist or other health care professional, as a type of topical fluoride therapy. Fluoride varnishes are typically not permanent, but due to their adherent nature they are able to stay in contact with the tooth surface for several hours or longer. The dental varnishes may be applied to the enamel, dentine or cementum of the tooth and can be used to help prevent decay, help remineralize the tooth surface, and to treat dentine hypersensitivity. Currently, varnish formulations are not utilized for delivery of antimicrobial peptides to body surfaces.

Dental varnishes known in the art are generally comprised of natural gum or shellac based resin, sodium fluoride, and various solvents, flavor additives, sweetener and pigments. Such dental varnishes are normally applied by a brush onto a tooth surface to prevent tooth decay via a fluoride release from the composition. One of issues with the well-known dental varnishes is that the fluoride release tends to be slow, i.e., more than 4 hours, due to the use of gum rosins as carriers. Conventional dental varnishes do not effectively release antimicrobial peptides, or C16G2, due to their chemical reaction and binding with biological molecules such as peptides.

Another issue of traditional varnishes is that most varnishes are yellow, and patients generally prefer not to draw attention to their fluoride varnished teeth. The color present in traditional varnish is caused by the dark color of natural gum rosins.

SUMMARY

Various embodiments contemplated herein may include, but need not be limited to, one or more of the following:

Embodiment 1

A dental varnish system for the sustained delivery of a specifically targeted antimicrobial peptide (STAMP) or a simple antimicrobial peptide (AMP), said varnish system comprising:
 a first component that is a dry powder, said first component comprising a specifically targeted antimicrobial peptide; and
 a second component that is a fluid, said second component comprising a varnish solution;
 where combination of said first component with said second component provides a varnish formulation for application to the surface of a tooth and delivery of an effective amount of said specifically targeted antimicrobial peptide (STAMP) or AMP to said tooth surface.

Embodiment 2

The varnish system of embodiment 1, wherein said varnish formulation provides release of an effective amount of said STAMP or AMP for at least 15 minutes, or for at least 30 minutes, or for at least 45 minutes, or for at least 1 hour after application, or for at least 2 hours after application, or for at least 4 hours after application, or for at least 6 hours after application, or for at least 8 hours after application, or for at least 12 hours after application, or for at least 24 hours after application, or for at least 48 hours after application.

Embodiment 3

The varnish system according to any one of embodiments 1-2, wherein said varnish formulation provides a release of at least 80% of said STAMP or AMP within about 8 hours or less, or within about 6 hours or less, or within about 4 hours or less, or within about 2 hours or less, or within about 1 hour or less.

Embodiment 4

The varnish system according to any one of embodiments 1-3, wherein said first component contains fewer excipients than said second component.

Embodiment 5

The varnish system according to any one of embodiments 1-4, wherein said specifically targeted antimicrobial peptide is provided in said first component in an amount that ranges from about 1 mg, or from about 5 mg, or from about 10 mg, or from about 20 mg, or from about 25 mg, or from about 30 mg, up to about 110 mg, or up to about 80 mg, or up to about 70 mg, or up to about 60 mg, or up to about 55 mg.

Embodiment 6

The varnish system according to any one of embodiments 1-5, wherein said specifically targeted antimicrobial peptide is provided in said first component in an amount that when said first component is combined with said second component in a weight ratio of 127 mg (first component) to 348 mg (second component), or in a weight ratio of 190 mg (first component) to 348 mg (second component), or in a weight ratio of 254 mg (first component) to 348 mg (second component) results in a final peptide concentration before drying that ranges from about 1 mM up to about 15 mM, or from about 2 mM up to about 12 mM, or from about 10 mg/mL up to about 50 mg/mL, or is about 11.4 mg/mL (2.82 mM), or about 22.8 mg/mL (5.65 mM), or about 45.5 mg/mL (11.3 mM).

Embodiment 7

The varnish system according to any one of embodiments 1-6, wherein said first component comprises said STAMP or AMP and a pH adjuster.

Embodiment 8

The varnish system of embodiment 7, wherein said pH adjuster comprises a combination of an acid and a base.

Embodiment 9

The varnish system of embodiment 7, wherein said first component comprises said antimicrobial peptide and a pH adjustor wherein said pH adjustor comprises an acid selected from the group consisting of citric acid, phosphoric acid, acetic acid and HCl, and/or a base selected from the group consisting of NaOH, ammonia, and TRIS.

Embodiment 10

The varnish system of embodiment 7, wherein said pH adjuster comprises histidine.

Embodiment 11

The varnish system according to any one of embodiments 1-10, wherein said specifically targeted antimicrobial peptide or AMP is present in said first component at a concentration ranging from about 0.1 mg/ml, or from about 0.5 mg/ml, or about 1 mg/ml, or about 3 mg/ml, or about 5 mg/ml up to about 50 mg/ml, or up to about 30 mg/ml, or up to about 15 mg/ml, or up to about 10 mg/ml, or up to about 8 mg/ml, and if said first component is dried, said concentration is before drying.

Embodiment 12

The varnish system of embodiment 11, wherein said specifically targeted antimicrobial peptide or AMP is present in said first component at a concentration ranging from 5 mg/ml up to about 8 mg/ml, or up to about 10 mg/ml, or up to about 20 mg/ml, or up to about 30 mg/ml and if said first component is dried said concentration is a concentration before drying.

Embodiment 13

The varnish system according to any one of embodiments 1-12, wherein combination of said first component with said second component in substantially equal parts as fluid, or where the first component is a dry powder in a ratio of powder to fluid second component ranging from about 100 mg powder up to about 260 mg powder mixed with 1 ml fluid second component produces a formulation having a pH ranging from about 5.0 to about 7.5, or from about 5.9 to about 6.1, and containing said STAMP or AMP in a form and concentration that is effective to kill *S. mutans*.

Embodiment 14

The varnish system of embodiment 13, wherein the first component is a dry powder in a ratio of powder to fluid second component of about 127 mg dry powder to 1 ml fluid second component.

Embodiment 15

The varnish system of embodiment 13, wherein the first component is a dry powder in a ratio of powder to fluid second component of about 190 mg dry powder to 1 ml fluid second component.

Embodiment 16

The varnish system of embodiment 13, wherein the first component is a dry powder in a ratio of powder to fluid second component of about 254 mg dry powder to 1 ml fluid second component.

Embodiment 17

The varnish system according to any one of embodiments 1-16, wherein said first component contains only said specifically targeted antimicrobial peptide.

Embodiment 18

The varnish system according to any one of embodiments 1-16, wherein said first component contains only said specifically targeted antimicrobial peptide, and a thickener.

Embodiment 19

The varnish system according to any one of embodiments 1-16, wherein said first component contains only said specifically targeted antimicrobial peptide and a preservative.

Embodiment 20

The varnish system according to any one of embodiments 1-16, wherein said first component contains only said specifically targeted antimicrobial peptide, a thickener, and a preservative.

Embodiment 21

The varnish system according to any one of embodiments 1-20, wherein said second component comprises a buffer.

Embodiment 22

The varnish system of embodiment 21, wherein said second component is buffered at a neutral or basic pH.

Embodiment 23

The varnish system of embodiment 21, wherein said second component is buffered at a pH of about pH 5.8 to about pH 6.8.

Embodiment 24

The varnish system of embodiment 21, wherein said second component is buffered at a pH of about pH 6.3.

Embodiment 25

The varnish system according to any one of embodiments 21-24, wherein said second component comprises a buffer selected from the group consisting of phosphate buffer, carbonate buffer, citrate buffer, HEPES, IVIES, Histidine, TRIS, and PIPES.

Embodiment 26

The varnish system according to any one of embodiments 21-24, wherein said second component comprises a phosphate buffer.

Embodiment 27

The varnish system according to any one of embodiments 1-26, wherein said first component or said second component further comprises a salt to adjust tonicity.

Embodiment 28

The varnish system of embodiment 27, wherein said salt is selected from the group consisting of sodium chloride, potassium chloride, sodium citrate, and sodium fluoride.

Embodiment 29

The varnish system according to any one of embodiments 27-28, wherein the concentration of salt, after combination of the first and second component and before drying, ranges from about 1 mg/ml, or from about 5 mg/ml, or from about 8 mg/ml up to about 15 mg/ml, or up to about 10 mg/ml of said first component or of said second component.

Embodiment 30

The varnish system according to any one of embodiments 27-29, wherein said salt is present in said second component.

Embodiment 31

The varnish system according to any one of embodiments 1-30, wherein said first component or said second component further comprises a bulking agent.

Embodiment 32

The varnish system of embodiment 31, wherein said bulking agent comprises a concentration, after combination of the first and second component and before drying, ranging from about 5 mg/ml, or from about 10 mg/ml, or from about 15 mg/ml, or from about 20 mg/ml, or from about 30 mg/ml, or from about 40 mg/ml, or from about 50 mg/ml up to about 100 mg/ml, or up to about 90 mg/ml, or up to about 80 mg/ml, or up to about 70 mg/ml, or ranges from about 60 mg/ml up to about 70 mg/ml of said first component and/or of said second component.

Embodiment 33

The varnish system according to any one of embodiments 31-32, wherein said bulking agent comprise an agent selected from the group consisting of mannitol, anhydrous lactose, sucrose, D(+)-trehalose, dextran 40, and povidone (PVP K24).

Embodiment 34

The varnish system according to any one of embodiments 31-33, wherein, said bulking agent comprises D-mannitol.

Embodiment 35

The varnish system according to any one of embodiments 31-34, wherein said bulking agent is present in said second component.

Embodiment 36

The varnish system according to any one of embodiments 1-35, wherein said first component or said second component further comprises one or more solubilizing/emulsifying agents.

Embodiment 37

The varnish system of embodiment 36, wherein the concentration, after combination of the first and second component and before drying, of a single solubilizing agent if present ranges in from about 1 mg/ml, or from about 5 mg/ml, or from about 8 mg/ml up to about 50 mg/ml, or up to about 40 mg/ml.

Embodiment 38

The varnish system according to any one of embodiments 36-37, wherein said one or more solubilizing/emulsifying agents comprise one or more agents selected from the group consisting of polyoxyl 15 hydroxystearate, propylene glycol, polysorbate 20, polysorbate 80, polyethylene glycol, and polyethylene glycol (15)-hydroxystearate.

Embodiment 39

The varnish system according to any one of embodiments 36-38, wherein said one or more solubilizing/emulsifying agents comprise a combination of polyoxyl 15 hydroxystearate, and propylene glycol.

Embodiment 40

The varnish system according to any one of embodiments 36-39, wherein said solubilizing/emulsifying agent(s) are present in said second component.

Embodiment 41

The varnish system according to any one of embodiments 1-40, wherein said first component or said second component further comprises a chelating agent.

Embodiment 42

The varnish system of embodiment 41, wherein the concentration of said chelating agent, after combination of the first and second component and before drying, ranges from about 0.1 mg/ml, or from about 0.5 mg/ml up to about 4 mg/ml, or up to about 3 mg/ml, or up to about 2 mg/ml, or up to about 1 mg/ml and/or ranges from about 0.5 mg/ml to about 1.5 mg/ml of said first component or said second component.

Embodiment 43

The varnish system according to any one of embodiments 41-42, wherein said chelating agent comprises an agent selected from the group consisting of ethylenediamine tetraacetic acid (EDTA), disodium dihydrate EDTA, calcium EDTA, diethylenetriamine pentaacetic acid (DTPA), nitrilotriacetic acid (NTA), DL-2, 3-Dimercapto-1-Propanesulfonic (DMPS), dimercaptosuccinic acid (DMSA).

Embodiment 44

The varnish system according to any one of embodiments 41-43, wherein said chelating agent is present in said second component.

Embodiment 45

The varnish system according to any one of embodiments 41-44, wherein said chelating agent is present in said first component.

Embodiment 46

The varnish system according to any one of embodiments 1-45, wherein said first component or said second component further comprises a preservative.

Embodiment 47

The varnish system of embodiment 46, wherein the concentration, after combination of the first and second component and before drying, of said preservative in said first component or said second component ranges from about 0.5 mg/ml, or from about 1 mg/ml, or from about 1.5 mg/ml up to about 5 mg/ml, or up to about 4 mg/ml, or up to about 3 mg/ml, or up to about 2 mg/ml.

Embodiment 48

The varnish system according to any one of embodiments 46-47, wherein said preservative comprises a preservative selected from the group consisting of methyl paraben, propyl paraben, sodium benzoate, and potassium sorbate.

Embodiment 49

The varnish system according to any one of embodiments 46-48, wherein said preservative is present in said first component.

Embodiment 50

The varnish system according to any one of embodiments 46-49, wherein said preservative is present in said second component.

Embodiment 51

The varnish system according to any one of embodiments 1-50, wherein said first component or said second component further comprises a sweetener.

Embodiment 52

The varnish system of embodiment 51, wherein said sweetener is selected from the group consisting of stevia, erythritol, sorbitol, acesulfame potassium, agave nectar, neotame, sucralose, aspartame, saccharin, and xylitol.

Embodiment 53

The varnish system according to any one of embodiments 51-52, wherein said sweetener is present in said second component.

Embodiment 54

The varnish system according to any one of embodiments 1-53, wherein said first component or said second component further comprises a colorant.

Embodiment 55

The varnish system of embodiment 54, wherein said colorant is selected from the group consisting of FD&C blue #1.

Embodiment 56

The varnish system according to any one of embodiments 54-55, wherein said colorant is present in said second component.

Embodiment 57

The varnish system according to any one of embodiments 1-56, wherein said first component or said second component further comprises flavoring agent.

Embodiment 58

The varnish system of embodiment 57, wherein said flavoring agent imparts a flavor selected from the group consisting of menthol, peppermint, spearmint, and wintergreen anise, apricot, cinnamon, fennel, lavender, neem, ginger, vanilla, lemon, and orange.

Embodiment 59

The varnish system according to any one of embodiments 57-58, wherein said flavoring agent is present in said second component.

Embodiment 60

The varnish system according to any one of embodiments 1-59, wherein said first component and/or said second component further comprises a thickener.

Embodiment 61

The varnish system of embodiment 60, wherein said thickener when present produces a combined formulation that is a form selected from the group consisting of a gel, a paste, and a foam.

Embodiment 62

The varnish system according to any one of embodiments 60-61, wherein said thickener is selected from the group consisting of hydroxypropyl methylcellulose (HPMC), methylcellulose, hydroxypropyl cellulose, and hydroxyethyl cellulose.

Embodiment 63

The varnish system according to any one of embodiments 60-62 wherein said thickener ranges in concentration from about 10 mg/ml, or from about 20 mg/ml, or from about 30 mg/ml up to about 100 mg/ml, or up to about 80 mg/ml, or up to about 60 mg/ml, or up to about 40 mg/ml of said first component and/or said second component.

Embodiment 64

The varnish system according to any one of embodiments 1-63, wherein said second component comprises a cationic (positively charged, permanently or pH dependent) random co-polymer based on dimethylaminoethyl methacrylate, butyl methacrylate, and/or methyl methacrylate (or methyl/ethyl acrylate).

Embodiment 65

The varnish system according to any one of embodiments 1-63, wherein said second component comprises Poly(butyl methacrylate-co-(2-dimethylaminoehtyl) methacrylate-co-methyl metacrylate), preferably at 1:2:1 mol ratio (Eudragit E).

Embodiment 66

The varnish system according to any one of embodiments 1-63, wherein said second component comprises a random co-polymer based on ethyl acrylate, methyl methacrylate, and trimethylammonioethyl methacrylate chloride.

Embodiment 67

The varnish system according to any one of embodiments 1-63, wherein said second component comprises, Poly(ethyl acrylate-co-methyl methacrylate-co-trimethylammonioethyl methacrylate chloride), preferably at 1:2:0.2 molar ratio (EUDRAGIT RL®) or 1:2:0.1 molar ratio (EUDRAGIT RS®).

Embodiment 68

The varnish system according to any one of embodiments 1-67, wherein said second component comprises about 28.6 varnish polymer, about 60% ethanol, and about 11.4% flavor.

Embodiment 69

The varnish system according to any one of embodiments 1-68, wherein said first component comprises a powder comprising about 10.7 to 21.4% antimicrobial peptide, about 72.82 to 83.6% Mannitol, about 1.55% Histidine, about 4.2% sucralose.

Embodiment 70

The varnish system of embodiment 69, wherein said first component comprises a powder comprising about 10.7% antimicrobial peptide, about 84% Mannitol, about 1.6% Histidine, about 4.2% sucralose.

Embodiment 71

The varnish system of embodiment 70, wherein said first component is combined with the second component in a ratio of about 127 mg dry powder to 1 ml of said second component (varnish solution).

Embodiment 72

The varnish system of embodiment 69, wherein said first component comprises a powder comprising about 14.3% antimicrobial peptide, about 80% Mannitol, about 1.6% histidine, about 4.2% sucralose.

Embodiment 73

The varnish system of embodiment 72, wherein said first component is combined with the second component in a ratio of about 190 mg dry powder to 1 ml of said second component (varnish solution).

Embodiment 74

The varnish system of embodiment 69, wherein said first component comprises a powder comprising about 21.4% antimicrobial peptide, about 73% mannitol, about 1.6% histidine, about 4.2% sucralose.

Embodiment 75

The varnish system of embodiment 74, wherein said first component is combined with the second component in a ratio of about 254 mg dry powder to 1 ml of said second component (varnish solution).

Embodiment 76

The varnish system of embodiment 69, wherein said second component comprises a varnish solution containing 28.6% EUDRAGIT E® and about 11.4% flavor in 60% ethanol.

Embodiment 77

The varnish system according to any one of embodiments 69-76, wherein said powder is either spray dried, pin milled, or sieved lyopowder with a median particle size of 20 to 30 µm and span of less than 5 units.

Embodiment 78

The varnish system according to any one of embodiments 69-77, wherein said first component comprises about 140 mg/mL of powder and when said first component is mixed with said second component comprising a varnish solution the final concentration of said antimicrobial peptide is about 1.7%.

Embodiment 79

The varnish system of embodiment 1, wherein when said first component is combined with said second component said system forms a varnish comprising: a specifically targeted antimicrobial peptide; D-mannitol; L-histidine; Amino Methacrylate Copolymer; and ethanol.

Embodiment 80

The varnish system of embodiment 79, wherein said varnish further comprises a colorant and/or a flavoring agent.

Embodiment 81

The varnish system of embodiment 1, wherein combination of said first component with said second component provides a varnish formulation selected from the group consisting of:

| Component | Function | Amount per dose |
| --- | --- | --- |
| C16G2 | Active (anti-*S. mutans*) agent | 13.60 mg |
| D-Mannitol, USP | Bulking agent | 105.92 mg |
| L-Histidine, USP | Buffer | 1.97 mg |
| Sucralose, NF | Flavoring Agent | 5.33 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1 |

NF = National Formulary,
q.s. = quantity sufficient;
USP = United States Pharmacopeia, and

| Component | Function | Amount per dose |
| --- | --- | --- |
| Specifically targeted antimicrobial peptide | Active Agent | 27.21 mg |
| D-Mannitol, USP | Bulking agent | 152.33 mg |
| L-Histidine, USP | Buffer | 2.95 mg |
| Sucralose, NF | Flavoring Agent | 8.00 mg |
| Ethanol, 200 proof, USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1, |
| Specifically targeted antimicrobial peptide | ActiveAgent | 54.43 mg |
| D-Mannitol, USP | Bulking agent | 184.97 mg |
| L-Histidine, USP | Buffer | 3.94 mg |
| Sucralose, NF | Flavoring Agent | 10.67 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1. | and

Embodiment 82

The varnish system according to any one of embodiments 1-81, wherein said first component and/or said second component comprises a fluoride.

Embodiment 83

The varnish system of embodiment 82, wherein said fluoride comprises an agent selected from the group consisting of sodium fluoride, stannous fluoride, sodium monofluorophosphate, zinc hexafluorosilicate, sodium hexafluorosilicate, ammonium fluoride, calcium fluoro-phosphate ($Ca_5[F(PO_4)_3]$) or fluorapatite, fluorine-doped hydroxyapatite (e.g., $Ca_5(PO_4)_3(OH,F)$, calcium fluoride ($CaF_2$) or fluorite or fluorspar, diofluorisilane, $TiF_4$, and acidulated fluoride.

Embodiment 84

The varnish system of embodiment 83, wherein said fluoride comprise sodium fluoride.

Embodiment 85

The varnish system of embodiment 84, wherein said first component comprises about 14.3% NaF.

Embodiment 86

A dental varnish for the sustained delivery of a specifically targeted antimicrobial peptide (STAMP) or a simple antimicrobial peptide (AMP), said varnish comprising: a specifically targeted antimicrobial peptide or a simple antimicrobial peptide (AMP); and a varnish solution.

Embodiment 87

The varnish of embodiment 86, wherein said varnish provides release of an effective amount of said STAMP or AMP for at least 15 minutes, or for at least 30 minutes, or for at least 45 minutes, or for at least 1 hour after application, or for at least 2 hours after application, or for at least 4 hours after application, or for at least 6 hours after application, or for at least 8 hours after application, or for at least 12 hours after application, or for at least 24 hours after application, or for at least 48 hours after application.

Embodiment 88

The varnish according to any one of embodiments 86-87, wherein said varnish formulation provides a release of at least 80% of said STAMP or AMP within about 8 hours or less, or within about 6 hours or less, or within about 4 hours or less, or within about 2 hours or less, or within about 1 hour or less.

Embodiment 89

The varnish according to any one of embodiments 86-88, wherein said specifically targeted antimicrobial peptide or AMP is present after combination of the first and second component before drying in an amount that ranges from about 1 mM, or from about 2 mM, or from about 3 mM, or from about 4 mM, or from about 5 mM, or from about 6 mM, or from about 7 mM, or from about 8 mM, or from about 9 mM, up to about 15 mM, or up to about 14 mM, or up to about 13 mM, or up to about 12 mM, or up to about 11.5 mM.

Embodiment 90

The varnish according to any one of embodiments 86-88, wherein said specifically targeted antimicrobial peptide or AMP is present in said varnish after combination of the first and second component before drying at a concentration ranging from about 0.1 mg/ml, or from about 0.5 mg/ml, or about 1 mg/ml, or about 3 mg/ml, or about 5 mg/ml up to about 50 mg/ml, or up to about 30 mg/ml, or up to about 15 mg/ml, or up to about 10 mg/ml, or up to about 8 mg/ml before drying.

Embodiment 91

The varnish according to any one of embodiments 86-88, wherein said specifically targeted antimicrobial peptide or AMP is present after combination of the first and second component before drying in said varnish at a concentration ranging from 5 mg/ml up to about 8 mg/ml, or up to about 10 mg/ml, or up to about 20 mg/ml, or up to about 30 mg/ml before drying or up to 46 mg/ml before drying.

Embodiment 92

The varnish according to any one of embodiments 86-91, wherein said varnish solution comprises a cationic (positively charged, permanently or pH dependent) random copolymer based on dimethylaminoethyl methacrylate, trimethylammonioethyl methacrylate chloride monomer, butyl methacrylate, and/or methyl methacrylate (or methyl/ethyl acrylate).

Embodiment 93

The varnish according to any one of embodiments 86-91, wherein said varnish solution comprises Poly(butyl methacrylate-co-(2-dimethylaminoehtyl) methacrylate-co-methyl metacrylate), preferably at 1:2:1 mol ratio (Eudragit E).

Embodiment 94

The varnish according to any one of embodiments 86-91, wherein said varnish solution comprises a random copolymer based on ethyl acrylate, methyl methacrylate, and trimethylammonioethyl methacrylate chloride.

Embodiment 95

The varnish according to any one of embodiments 86-91, wherein said varnish solution comprises, Poly(ethyl acrylate-co-methyl methacrylate-co-trimethylammonioethyl methacrylate chloride), preferably at 1:2:0.2 molar ratio (EUDRAGIT RL®) or 1:2:0.1 molar ratio (EUDRAGIT RS®).

Embodiment 96

The varnish according to any one of embodiments 86-95, wherein said varnish comprises one or more agents selected from the group consisting of a bulking agent, a buffer, a flavoring agent, a solvent, an emulsifying agent, a chelating agent, a coloring agent, and an in process pH adjustor.

Embodiment 97

The varnish of embodiment 96, wherein said varnish comprises a pH adjuster.

Embodiment 98

The varnish of embodiment 97, wherein said pH adjuster comprises a combination of an acid and a base.

Embodiment 99

The varnish of embodiment 97, wherein said pH adjustor comprises an acid selected from the group consisting of citric acid, phosphoric acid, acetic acid and HCl, and/or a base selected from the group consisting of NaOH, ammonia, and TRIS.

Embodiment 100

The varnish of embodiment 97, wherein said pH adjuster comprises histidine.

Embodiment 101

The varnish according to any one of embodiments 96-100, wherein said varnish comprises a buffer.

Embodiment 102

The varnish of embodiment 101, wherein said varnish comprises a buffer selected from the group consisting of phosphate buffer, carbonate buffer, citrate buffer, HEPES, MES, Histidine, TRIS, and PIPES.

Embodiment 103

The varnish of embodiment 101, wherein said varnish comprises a phosphate buffer.

Embodiment 104

The varnish according to any one of embodiments 96-103, wherein said varnish is buffered at a neutral or basic pH.

Embodiment 105

The varnish of embodiment 104, wherein said varnish is buffered at a pH of about pH 5.8 to about pH 6.8.

Embodiment 106

The varnish of embodiment 104, wherein said varnish is buffered at a pH of about pH 6.3.

Embodiment 107

The varnish according to any one of embodiments 86-106, wherein varnish comprises a salt to adjust tonicity.

Embodiment 108

The varnish of embodiment 107, wherein said salt is selected from the group consisting of sodium chloride, potassium chloride, sodium citrate, and sodium fluoride.

Embodiment 109

The varnish according to any one of embodiments 107-108, wherein the concentration of salt, in the combined varnish before application, ranges from about 1 mg/ml, or from about 5 mg/ml, or from about 8 mg/ml up to about 15 mg/ml.

Embodiment 110

The varnish according to any one of embodiments 96-109, wherein said varnish comprises a bulking agent.

Embodiment 111

The varnish of embodiment 110, wherein said bulking agent, in the combined varnish before application, comprises a concentration ranging from about 5 mg/ml, or from about 10 mg/ml, or from about 15 mg/ml, or from about 20 mg/ml, or from about 30 mg/ml, or from about 40 mg/ml, or from about 50 mg/ml up to about 100 mg/ml, or up to about 90 mg/ml, or up to about 80 mg/ml, or up to about 70 mg/ml, or ranges from about 60 mg/ml up to about 70 mg/ml of said first component and/or of said second component.

Embodiment 112

The varnish according to any one of embodiments 110-111, wherein said bulking agent comprises an agent selected from the group consisting of mannitol, anhydrous lactose, sucrose, D(+)-trehalose, dextran 40, and povidone (PVP K24).

Embodiment 113

The varnish of embodiment 112, wherein, said bulking agent comprises D-mannitol.

Embodiment 114

The varnish according to any one of embodiments 96-113, wherein said varnish comprises a solvent.

Embodiment 115

The varnish of embodiment 114, wherein said solvent comprises an alcohol.

Embodiment 116

The varnish of embodiment 115, wherein said solvent comprises ethanol or isopropyl alcohol.

Embodiment 117

The varnish according to any one of embodiments 96-116, wherein said varnish comprises one or more emulsifying agents.

Embodiment 118

The varnish of embodiment 117, wherein said one or more emulsifying agents comprise one or more agents selected from the group consisting of polyoxyl 15 hydroxystearate, propylene glycol, polysorbate 20, polysorbate 80, polyethylene glycol, and polyethylene glycol (15)-hydroxystearate.

Embodiment 119

The varnish of embodiment 118, wherein said one or more solubilizing/emulsifying agents comprise a combination of polyoxyl 15 hydroxystearate, and propylene glycol.

Embodiment 120

The varnish according to any one of embodiments 117-119, wherein the concentration of a single emulsifying agent when present in the combined varnish before application ranges in from about 1 mg/ml, or from about 5 mg/ml, or from about 8 mg/ml up to about 50 mg/ml, or up to about 40 mg/ml.

Embodiment 121

The varnish according to any one of embodiments 96-120, wherein said varnish comprises a chelating agent.

Embodiment 122

The varnish of embodiment 121, wherein said chelating agent comprises an agent selected from the group consisting of ethylenediamine tetraacetic acid (EDTA), disodium dihydrate EDTA, calcium EDTA, diethylenetriamine pentaacetic acid (DTPA), nitrilotriacetic acid (NTA), DL-2, 3-Dimercapto-1-Propanesulfonic (DMPS), dimercaptosuccinic acid (DMSA).

Embodiment 123

The varnish according to any one of embodiments 121-122, wherein the concentration of said chelating agent in the combined varnish before application ranges from about 0.1 mg/ml, or from about 0.5 mg/ml up to about 4 mg/ml, or up to about 3 mg/ml, or up to about 2 mg/ml, or up to about 1 mg/ml and/or ranges from about 0.5 mg/ml to about 1.5 mg/ml of said first component or said second component.

Embodiment 124

The varnish according to any one of embodiments 96-123, wherein said varnish comprises a preservative.

Embodiment 125

The varnish of embodiment 124, wherein said preservative comprises a preservative selected from the group consisting of methyl paraben, propyl paraben, sodium benzoate, and potassium sorbate.

Embodiment 126

The varnish according to any one of embodiments 124-125, wherein the concentration of said preservative in the combined varnish before application ranges from about 0.5 mg/ml, or from about 1 mg/ml, or from about 1.5 mg/ml up to about 5 mg/ml, or up to about 4 mg/ml, or up to about 3 mg/ml, or up to about 2 mg/ml.

Embodiment 127

The varnish according to any one of embodiments 96-126, wherein said varnish comprises a sweetener.

Embodiment 128

The varnish of embodiment 127, wherein said sweetener is selected from the group consisting of stevia, erythritol, sorbitol, acesulfame potassium, agave nectar, neotame, sucralose, aspartame, saccharin, and xylitol.

Embodiment 129

The varnish according to any one of embodiments 96-128, wherein said varnish comprises a colorant.

Embodiment 130

The varnish of embodiment 129, wherein said colorant is selected from the group consisting of FD&C blue #1.

Embodiment 131

The varnish according to any one of embodiments 96-130, wherein said varnish comprises flavoring agent.

Embodiment 132

The varnish of embodiment 131, wherein said flavoring agent imparts a flavor selected from the group consisting of menthol, peppermint, spearmint, and wintergreen anise, apricot, cinnamon, fennel, lavender, neem, ginger, vanilla, lemon, and orange.

Embodiment 133

The varnish of embodiment 86, wherein said varnish comprises: a specifically targeted antimicrobial peptide; mannitol; L-histidine; and sucralose.

Embodiment 134

The varnish of embodiment 133, wherein said varnish comprises: a specifically targeted antimicrobial peptide; D-mannitol; L-histidine; Amino Methacrylate Copolymer; and ethanol.

Embodiment 135

The varnish of embodiment 134, wherein said varnish further comprises a colorant and/or a flavoring agent.

Embodiment 136

The varnish of embodiment 86, wherein said varnish comprises, wherein said varnish comprises a formulation selected from the group consisting of:

| Component | Function | Amount per dose |
|---|---|---|
| C16G2 agent | Active (anti-*S. mutans*) | 13.60 mg |
| D-Mannitol, USP | Bulking agent | 105.92 mg |
| L-Histidine, USP | Buffer | 1.97 mg |
| Sucralose, NF | Flavoring Agent | 5.33 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1 |

NF = National Formulary,
q.s. = quantity sufficient;
USP = United States Pharmacopeia, and

| Component | Function | Amount per dose |
|---|---|---|
| Specifically targeted antimicrobial peptide | Active Agent | 27.21 mg |
| D-Mannitol, USP | Bulking agent | 152.33 mg |
| L-Histidine, USP | Buffer | 2.95 mg |
| Sucralose, NF | Flavoring Agent | 8.00 mg |
| Ethanol, 200 proof, USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1, | and

| Component | Function | Amount per dose |
|---|---|---|
| Specifically targeted antimicrobial peptide | Active Agent | 54.43 mg |
| D-Mannitol, USP | Bulking agent | 184.97 mg |
| L-Histidine, USP | Buffer | 3.94 mg |
| Sucralose, NF | Flavoring Agent | 10.67 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1. |

Embodiment 137

The varnish according to any one of embodiments 86-136, wherein said first formulation and/or said second formulation comprises a fluoride.

Embodiment 138

The system of embodiment 137, wherein said fluoride comprises a fluoride selected from the group consisting of sodium fluoride, ammonium fluoride, and an acidulated fluoride.

Embodiment 139

The varnish according to any one of embodiments 1-85, or the varnish system according to any of embodiments 86-138, wherein said varnish comprises a specifically targeted antimicrobial peptide comprising a targeting peptide that binds *Streptococcus mutans* and where said targeting peptide is attached to an antimicrobial peptide directly or through an amino acid or a peptide linker.

Embodiment 140

The varnish or varnish system of embodiment 139, wherein the sequence of said specifically targeted antimicrobial peptide comprises or consists of the amino acid sequence TFFRLFNRSFTQALGKGGGKNLRIIRKGIHIIKKY.

Embodiment 141

The varnish or varnish system of embodiment 140, wherein said specifically targeted antimicrobial peptide is amidated at the carboxyl terminus.

Embodiment 142

The varnish or varnish system of embodiment 139, wherein said targeting peptide comprises a peptide that ranges in length from 5 amino acid, or from 6 amino acids, or from 7 amino acids, or from 8 amino acids up to about 50 amino acids, or up to about 40 amino acids, or up to about 30 amino acids, or up to about 20 amino acids.

Embodiment 143

The varnish or varnish system according to any one of embodiments 139 or 142, wherein said targeting peptide comprises or consists of an amino acid sequence selected from the group consisting of SGSL- STFFRLFNRSFTQALGK (CSP, SEQ ID NO:331) or a fragment thereof, EMRLSKFFRDFILQRKK (CSP1, (SEQ ID NO:332) or a fragment thereof, and EMRISRIILD-FLFLRKK (CSP2, (SEQ ID NO:333), NIFEYFLE (SEQ ID NO:334). or a fragment thereof.

Embodiment 144

The varnish or varnish system according to any one of embodiments 139 or 142, wherein the amino acid sequence of said targeting peptide comprises or consists of the amino acid sequence TFFRLFNR and comprises at least 8, or at least 9, or at least 10, or at least 11, or at least 12, or at least 13, or at least 14, or at least 15, or at least 16, or at least 17, or at least 18, or at least 19, or at least 20, or 21 contiguous amino acids of CSP.

Embodiment 145

The varnish or varnish system of embodiment 144, wherein the amino acid sequence of said targeting peptide comprises or consists of an amino acid sequence selected from the group consisting of TFFRLFNR (SEQ ID NO:335), TFFRLFNRS (SEQ ID NO:336), TFFRLFNRS (SEQ ID NO:337), TFFRLFNRSF (SEQ ID NO:338), TFFRLFNRSFT (SEQ ID NO:339), TFFRLFNRSFTQ (SEQ ID NO:340), TFFRLFNRSFTQA (SEQ ID NO:341), TFFRLFNRSFTQAL (SEQ ID NO:342), TFFRLFNRSFTQALG (SEQ ID NO:343), TFFRLFNRSFTQALGK (SEQ ID NO:344), STFFRLFNR (SEQ ID NO:345), STFFRLFNRS (SEQ ID NO:346), STFFRLFNRS (SEQ ID NO:347), STFFRLFNRSF (SEQ ID NO:348), STFFRLFNRSFT (SEQ ID NO:349), STFFRLFNRSFTQ (SEQ ID NO:350), STFFRLFNRSFTQA (SEQ ID NO:351), STFFRLFNRSFTQAL (SEQ ID NO:352), STFFRLFNRSFTQALG (SEQ ID NO:353), STFFRLFNRSFTQALGK (SEQ ID NO:354), LSTFFRLFNR (SEQ ID NO:355), LSTFFRLFNRS (SEQ ID NO:356), LSTFFRLFNRS (SEQ ID NO:357), LSTFFRLFNRSF (SEQ ID NO:358), LSTFFRLFNRSFT (SEQ ID NO:359), LSTFFRLFNRSFTQ (SEQ ID NO:360), LSTFFRLFNRSFTQA (SEQ ID NO:361), LSTFFRLFNRSFTQAL (SEQ ID NO:362), LSTFFRLFNRSFTQALG (SEQ ID NO:363), LSTFFRLFNRSFTQALGK (SEQ ID NO:364), SLSTFFRLFNR (SEQ ID NO:365), SLSTFFRLFNRS (SEQ ID NO:366), SLSTFFRLFNRS (SEQ ID NO:367), SLSTFFRLFNRSF (SEQ ID NO:368), SLSTFFRLFNRSFT (SEQ ID NO:369), SLSTFFRLFNRSFTQ (SEQ ID NO:370), SLSTFFRLFNRSFTQA (SEQ ID NO:371), SLSTFFRLFNRSFTQAL (SEQ ID NO:372), SLSTFFRLFNRSFTQALG (SEQ ID NO:373), SLSTFFRLFNRSFTQALGK (SEQ ID NO:374), GSL-STFFRLFNR (SEQ ID NO:375), GSLSTFFRLFNRS (SEQ ID NO:376), GSLSTFFRLFNRS (SEQ ID NO:377), GSL-STFFRLFNRSF (SEQ ID NO:378), GSLSTFFRLFNRSFT (SEQ ID NO:379), GSLSTFFRLFNRSFTQ (SEQ ID NO:380), GSLSTFFRLFNRSFTQA (SEQ ID NO:381), GSLSTFFRLFNRSFTQAL (SEQ ID NO:382), GSL-STFFRLFNRSFTQALG (SEQ ID NO:383), GSL-STFFRLFNRSFTQALGK (SEQ ID NO:384), SGSL-STFFRLFNR (SEQ ID NO:385), SGSLSTFFRLFNRS (SEQ ID NO:386), SGSLSTFFRLFNRS (SEQ ID NO:387), SGSLSTFFRLFNRSF (SEQ ID NO:388), SGSL-STFFRLFNRSFT (SEQ ID NO:389), SGSL-STFFRLFNRSFTQ (SEQ ID NO:390), SGSL-STFFRLFNRSFTQA (SEQ ID NO:391), SGSLSTFFRLFNRSFTQAL (SEQ ID NO:392), and SGSL-STFFRLFNRSFTQALG (SEQ ID NO:393).

Embodiment 146

The varnish or varnish system according to any one of embodiments 139 or 142, wherein said targeting peptide comprises or consists of the amino acid sequence $X^1$-$X^2$-F-R-$X^5$-$X^6$-$X^7$-R-$X^9$-$X^{10}$-$X^{11}$-$X^{12}$-$X^{13}$-$X^{14}$-$X^{15}$-$X^{16}$ or the inverse of said amino acid sequence, wherein:

$X^1$ is a polar amino acid, or A;
$X^2$ is F, W, Q, A, or an analog thereof;
$X^5$ is a hydrophobic amino acid;
$X^6$ is a hydrophobic amino acid, N, Q, or an analog thereof;
$X^7$ is a polar amino acid, A, F, or an analog thereof;
$X^9$ is a polar amino acid, A or an analog thereof;
$X^{10}$ is a hydrophobic amino acid, Q, A, or an analog thereof;
$X^{11}$ is a hydrophobic amino acid;
$X^{12}$ is Q, A, or an analog thereof; $X^{13}$ is a non-polar amino acid;
$X^{14}$ is a hydrophobic amino acid;
$X^{15}$ is a non-polar amino acid, N, S, D, or an analog thereof;
$X^{16}$ is a polar amino acid, F, A, or an analog thereof and said peptide ranges in length up to 100 amino acids.

Embodiment 147

The varnish or varnish system of embodiment 146, wherein $X^1$ is A or T.

Embodiment 148

The varnish or varnish system according to any one of embodiments 146-147, wherein $X^2$ is F, W, Q, or A.

Embodiment 149

The varnish or varnish system of embodiment 148, wherein $X^2$ is F.

Embodiment 150

The varnish or varnish system according to any one of embodiments 146-149, wherein $X^5$ is L, A, or an analogue thereof.

Embodiment 151

The varnish or varnish system of embodiment 150, wherein $X^5$ is L.

Embodiment 152

The varnish or varnish system according to any one of embodiments 146-151, wherein $X^6$ is F, L, N, A, Q, or an analog thereof.

Embodiment 153

The varnish or varnish system of embodiment 152, wherein $X^6$ is a hydrophobic amino acid.

Embodiment 154

The varnish or varnish system of embodiment 152, wherein $X^6$ is F.

Embodiment 155

The varnish or varnish system according to any one of embodiments 146-154, wherein $X^7$ is a polar amino acid, A, or F.

Embodiment 156

The varnish or varnish system of embodiment 155, wherein $X^7$ is a polar amino acid or A.

Embodiment 157

The varnish or varnish system of embodiment 155, wherein $X^7$ is N, A, S, D, or F.

Embodiment 158

The varnish or varnish system of embodiment 155, wherein $X^7$ is N or A.

Embodiment 159

The varnish or varnish system of embodiment 155, wherein $X^7$ is N.

Embodiment 160

The varnish or varnish system according to any one of embodiments 146-159, wherein $X^9$ is a polar amino acid, or A.

Embodiment 161

The varnish or varnish system of embodiment 160, wherein $X^9$ is S or A.

Embodiment 162

The varnish or varnish system of embodiment 160, wherein $X^9$ is S.

Embodiment 163

The varnish or varnish system according to any one of embodiments 146-162, wherein $X^{10}$ is a hydrophobic amino acid, Q, or A.

Embodiment 164

The varnish or varnish system of embodiment 163, wherein $X^{10}$ is a hydrophobic amino acid.

Embodiment 165

The varnish or varnish system of embodiment 164, wherein $X^{10}$ is F, L, or an analog thereof.

Embodiment 166

The varnish or varnish system of embodiment 164, wherein $X^{10}$ is F.

Embodiment 167

The varnish or varnish system according to any one of embodiments 146-166, wherein $X^{11}$ is T, A, or an analog thereof.

Embodiment 168

The varnish or varnish system of embodiment 167, wherein $X^{11}$ is T.

Embodiment 169

The varnish or varnish system according to any one of embodiments 146-168, wherein $X^{12}$ is Q or A.

Embodiment 170

The varnish or varnish system of embodiment 169, wherein $X^{12}$ is Q.

Embodiment 171

The varnish or varnish system according to any one of embodiments 146-170, wherein $X^{13}$ is P, A, or an analog thereof.

Embodiment 172

The varnish or varnish system of embodiment 171, wherein $X^{13}$ is A.

Embodiment 173

The varnish or varnish system according to any one of embodiments 146-172, wherein $X^{14}$ is L, A, or an analog thereof.

Embodiment 174

The varnish or varnish system of embodiment 173, wherein $X^{15}$ is L.

Embodiment 175

The varnish or varnish system according to any one of embodiments 146-174, wherein $X^{15}$ is a non-polar amino acid, N, S, or D.

Embodiment 176

The varnish or varnish system of embodiment 175, wherein $X^{15}$ is G, A, F, N, S, D, or an analog thereof.

Embodiment 177

The varnish or varnish system of embodiment 176, wherein $X^{15}$ is G, or A.

Embodiment 178

The varnish or varnish system according to any one of embodiments 146-177, wherein $X^{16}$ is $X^{16}$ is a polar amino acid, F, or A.

Embodiment 179

The varnish or varnish system of embodiment 178, wherein $X^{16}$ is a polar amino acid.

Embodiment 180

The varnish or varnish system of embodiment 179, wherein $X^{16}$ is K, Q, or an analog thereof.

Embodiment 181

The varnish or varnish system of embodiment 179, wherein $X^{16}$ is K.

Embodiment 182

The varnish or varnish system according to any one of embodiments 146-181, wherein said peptide does not comprise the amino acid sequence TFFRLFNRSFTQALGK.

Embodiment 183

The varnish or varnish system of embodiment 146, wherein said peptide comprises or consists of an amino acid sequence selected from the group consisting of AFFRAFNRAFAQALAK (SEQ ID NO:5), TFFRAFARAFAQAAAK (SEQ ID NO:6), AFFRAFARAFAQALAK (SEQ ID NO:7), AFFRLFARAFAQAAAK (SEQ ID NO:8), TLFRLLNRSLTQALGK (SEQ ID NO:9), TFFRLFNRSFTQALFK (SEQ ID NO:10), TFFRLFNRSLTQALGK (SEQ ID NO:11), TFFRLFNRSFTQALNK (SEQ ID NO:12), AFFRAFARAFAQAAAK (SEQ ID NO:13), AFFRAFNRAFAQAAAK (SEQ ID NO:14), TFFRLFNRSFTQALSK (SEQ ID NO:15), AFFRAFARSFAQAAAK (SEQ ID NO:16), AFFRAFARAFAQAAGK (SEQ ID NO:17), AFFRAFARAFTQAAAK (SEQ ID NO:18), TFFRLFNRSFTQALGQ (SEQ ID NO:19), TFFRLLNRSFTQALGK (SEQ ID NO:20), TWFRLFNRSFTQALGK (SEQ ID NO:21), AFFRAFARAFAQAFAK (SEQ ID NO:22), TQFRLFNRSFTQALGK (SEQ ID NO:23), TFFRLFNRSFTQALDK (SEQ ID NO:24), TFFRLFNRSFTQALAK (SEQ ID NO:25), TFFRLFNRSFTQALGE (SEQ ID NO:26), TFFRLFSRSFTQALGK (SEQ ID NO:27), TFFRLFNRSFTQALGA (SEQ ID NO:28), TFFRLFDRSFTQALGK (SEQ ID NO:29), TFFRLFNRSFTQALGF (SEQ ID NO:30), TFFRAFARSFTQAAAK (SEQ ID NO:31), TFFRLFARSFTQAAGK (SEQ ID NO:32), TFFRLFNRSFTQ L K (SEQ ID NO:33), TFFRLFNRSFTQALGS (SEQ ID NO:34), TLFRLFNRSFTQALGK (SEQ ID NO:35), TFFRLNFRSFTQALGK (SEQ ID NO:36), TFFRLFNRSQTQALGK (SEQ ID NO:37), TFFRLFAAAFTQALGK (SEQ ID NO:38), TFFRLFNRSFTQALGK (SEQ ID NO:39), TFFRLFNRSAAAALGK (SEQ ID NO:40), TFFRLFFRSNTQALGK (SEQ ID NO:41), TFFRLFNRSFTQPLGK (SEQ ID NO:42), TAFRLANRSATQALGK (SEQ ID NO:43), TFFRLFNRSFTQAAAA (SEQ ID NO:44), TFFRLQNRSFTQALGK (SEQ ID NO:45), TFFRLFNRSFTQALPK (SEQ ID NO:46), TYYRLFNRSFTQALGK (SEQ ID NO:47), TFFRLF RSFTQALGK (SEQ ID NO:48), and TQFRLQNRSQTQALGK (SEQ ID NO:49).

Embodiment 184

The varnish or varnish system according to any one of embodiments 146-183, wherein the amino acid sequence of said peptide is the inverse of said sequence.

Embodiment 185

The varnish or varnish system according to any one of embodiments 146-184, wherein said targeting peptide ranges in length up to 50 amino acids or up to 25 amino acids, or up to 20 amino acids.

Embodiment 186

The varnish or varnish system according to any one of embodiments 146-185, wherein said targeting peptide is an "L" peptide.

Embodiment 187

The varnish or varnish system according to any one of embodiments 146-185, wherein said targeting peptide is a "D" peptide.

Embodiment 188

The varnish or varnish system according to any one of embodiments 146-185, wherein said targeting peptide is a beta peptide.

Embodiment 189

The varnish or varnish system according to any one of embodiments 139, and 141-188, wherein said targeting peptide is attached to an antimicrobial peptide comprising or consisting of an amino acid sequence found in Table 7.

Embodiment 190

The varnish or varnish system according to any one of embodiments 139, and 141-188, wherein said targeting peptide is attached to an antimicrobial peptide comprising or consisting of an amino acid sequence selected from the group consisting of G2 KNLRIIRKGIHIIKKY* (SEQ ID NO:2), Novispirin G10 KNLRRIIRKGIHIIKKYG (SEQ ID NO:49), Novispirin T10 KNLRRIIRKTIHIIKKYG (SEQ ID NO:50), Novispirin G7 KNLRRIGRKIIHIIKKYG (SEQ ID NO:51), Novispirin T7 KNLRRITRKIIHIIKKYG (SEQ ID NO:52), Ovispirin KNLRRIIRKIIHIIKKYG (SEQ ID NO:53), PGG GLLRRLRKKIGEIFKKYG (SEQ ID NO:54), Protegrin-1 RGGRLCYCRRRFCVCVGR* (SEQ ID NO:55), K-1 GLGRVIGRLIKQIIWRR (SEQ ID NO:56), K-2 VYRKRKSILKIYAKLKGWH (SEQ ID NO:57), K-7 NYRLVNAIFSKIFKKKFIKF (SEQ ID NO:58), K-8 KILKFLFKKVF (SEQ ID NO:59), K-9 FIRKFLKKWLL (SEQ ID NO:60), K-10 KLFKFLRKHLL (SEQ ID NO:61), K-11 KILKFLFKQVF (SEQ ID NO:62), K-12 KILKKLFKFVF (SEQ ID NO:63), K-13 GILKKLFTKVF (SEQ ID NO:64), K-14 LRKFLHKLF (SEQ ID NO:65), K-15 LRKNLRWLF (SEQ ID NO:66), K-16 FIRKFLQKLHL (SEQ ID NO:67), K-17 FTRKFLKFLHL (SEQ ID NO:68), K-18 KKFKKFKVLKIL (SEQ ID NO:69), K-19 LLKLLKLKKLKF (SEQ ID NO:70), K-20 FLKFLKKFFKKLKY (SEQ ID NO:71), K-21 GWLKMFKKIIGKFGKF (SEQ ID NO:72), K-22

GIFKKFVKILYKVQKL (SEQ ID NO:73), and B-33 FKKFWKWFRRF (SEQ ID NO:107).

Embodiment 191

The varnish or varnish system according to any one of embodiments 139, and 141-190, wherein said targeting peptide and/or said antimicrobial peptide is an "L" peptide.

Embodiment 192

The varnish or varnish system according to any one of embodiments 139, and 141-190, wherein said targeting peptide and/or said antimicrobial peptide is a "D" peptide.

Embodiment 193

The varnish or varnish system according to any one of embodiments 139, and 141-190, wherein said targeting peptide and/or said antimicrobial peptide is a beta peptide.

Embodiment 194

The varnish or varnish system according to any one of embodiments 139, and 141-193, wherein said targeting peptide is chemically conjugated to said antimicrobial peptide.

Embodiment 195

The varnish or varnish system of embodiment 194, wherein said targeting peptide is chemically conjugated to said antimicrobial peptide via a linker.

Embodiment 196

The varnish or varnish system of embodiment 195, wherein said targeting peptide is chemically conjugated to said effector via a linker comprising a polyethylene glycol (PEG) or a non-peptide linker found in Table 8.

Embodiment 197

The varnish or varnish system according to any one of embodiments 139, and 141-193, wherein said targeting peptide is attached directly to said antimicrobial peptide (i.e., without a linker).

Embodiment 198

The varnish or varnish system according to any one of embodiments 139, and 141-193, wherein said targeting peptide is attached to said antimicrobial peptide via a peptide linkage.

Embodiment 199

The varnish or varnish system of embodiment 198, wherein said effector comprises an antimicrobial peptide and said construct is a fusion protein.

Embodiment 200

The varnish or varnish system according to any one of embodiments 198 and 199, wherein said targeting peptide is attached to said antimicrobial peptide by a peptide linker comprising or consisting of an amino acid sequence found in Table 8.

Embodiment 201

The varnish or varnish system of embodiment 200, wherein said peptide linker comprises or consists of the amino acid sequence GGG.

Embodiment 202

The varnish or varnish system according to any one of embodiments 139, and 141-201, wherein said peptide bears no terminal protecting groups.

Embodiment 203

The varnish or varnish system according to any one of embodiments 146-201, wherein said specifically targeted antimicrobial peptide bears one or more protecting groups.

Embodiment 204

The varnish or varnish system of embodiment 203, wherein said one or more protecting groups are independently selected from the group consisting of acetyl, amide, 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO), t-butoxymethyl (Bum), t-butoxy (tBuO), t-Butyl (tBu), and Trifluoroacetyl (TFA).

Embodiment 205

The varnish or varnish system of embodiment 203, wherein said specifically targeted antimicrobial peptide comprises a protecting group at a carboxyl and/or amino terminus.

Embodiment 206

The varnish or varnish system of embodiment 205, wherein a carboxyl terminus is amidated.

Embodiment 207

A dental varnish system for the sustained delivery of a fluoride, said varnish system comprising:
a first component that is a dry powder, said first component comprising a fluoride and a bulking agent; and
a second component that is a fluid, said second component comprising a varnish solution;
where combination of said first component with said second component provides a varnish formulation for application to the surface of a tooth.

Embodiment 208

The varnish system of embodiment 207, wherein said varnish formulation provides release of an effective amount of a fluoride for at least 1 hour after application, or for at least 2 hours after application, or for at least 4 hours after application, or for at least 6 hours after application, or for at least 8 hours after application, or for at least 12 hours after application, or for at least 24 hours after application, or for at least 48 hours after application.

Embodiment 209

The varnish system according to any one of claims 207-208, wherein said varnish formulation provides a release of at least 80% of total fluoride within about 8 hours or less, or within about 6 hours or less, or within about 4 hours or less.

Embodiment 210

The varnish system according to any one of embodiments 207-209, wherein said fluoride comprises an agent selected from the group consisting of sodium fluoride, stannous fluoride, sodium monofluorophosphate, zinc hexafluorosilicate, sodium hexafluorosilicate, ammonium fluoride, calcium fluoro-phosphate ($Ca_5[F(PO_4)_3]$) or fluorapatite, fluorine-doped hydroxyapatite (e.g., $Ca_5(PO_4)_3(OH,F)$, calcium fluoride ($CaF_2$) or fluorite or fluorspar, diofluorisilane, $TiF_4$, and acidulated fluoride.

Embodiment 211

The varnish system of embodiment 210, wherein said fluoride comprises sodium fluoride.

Embodiment 212

The varnish system according to any one of embodiments 207-211, wherein said fluoride comprises from about 3 weight percent to about 50 weight percent of said first component.

Embodiment 213

The varnish system according to any one of embodiments 207-212, wherein said fluoride comprises from about 0.5 to about 5 weight percent of the combined varnish formulation.

Embodiment 214

The varnish system according to any one of embodiments 207-213, wherein said bulking agent comprises an agent selected from the group consisting of mannitol, lactose, sucrose, trehalose, sorbitol, glucose, raffinose, arginine, glycine, histidine, dextran, erythritol, glycylglycine, glycine, histidine, polyethylene glycol, and combinations thereof.

Embodiment 215

The varnish system of embodiment 214, wherein said bulking agent comprises mannitol.

Embodiment 216

The varnish system according to any one of embodiments 207-215, wherein said bulking agent comprises from about 50 weight percent to about 97 weight percent of said first component.

Embodiment 217

The varnish system according to any one of embodiments 207-216, wherein said first component and/or said second component comprises a sweetener.

Embodiment 218

The varnish system of embodiment 217, wherein said sweetener comprises a sweetener selected from the group consisting of sucralose, acesulfame potassium, agave nectar, aspartame, high-fructose corn syrup, sucrose, neotame, *stevia*, saccharin, and sugar alcohols.

Embodiment 219

The varnish system of embodiment 218, wherein said sweetener comprises sucralose.

Embodiment 220

The varnish system of embodiment 218, wherein said sweetener comprises a sugar alcohol selected from the group consisting of sorbitol, xylitol, and mannitol.

Embodiment 221

The varnish system according to any one of embodiments 217-220, wherein said sweetener comprises from about 1 weight percent up to about 6 weight percent of said first component or said second component.

Embodiment 222

The varnish system according to any one of embodiments 217-221, wherein said sweetener is in said first component.

Embodiment 223

The varnish system according to any one of embodiments 217-221, wherein said sweetener is in said second component.

Embodiment 224

The varnish system according to any one of embodiments 207-223, wherein said varnish comprises a polymer or copolymer of one or more components selected from the group consisting of acrylic acid, methacrylic acid, and their esters.

Embodiment 225

The varnish system of embodiment 224, wherein said varnish comprises a polymer or copolymer of one or more components selected from the group consisting of dimethylaminoethyl methacrylate, butyl methacrylate, methylmethacrylate, and hydroxyethyl methacrylate (HEMA).

Embodiment 226

The varnish system of embodiment 225, wherein said varnish comprises a copolymer of dimethylaminoethyl methacrylate, butyl methacrylate, and methylmethacrylate.

Embodiment 227

The varnish system of embodiment 226, wherein said varnish comprises dimethylaminoethyl methacrylate, butyl methacrylate, and methylmethacrylate copolymer in a ratio of 2:1:1.

Embodiment 228

The varnish system according to any one of embodiments 207-227, wherein said second component comprises a solvent selected from the group consisting of an alcohol, an ester (e.g., ethylacetate), a ketone (e.g., acetone), and a $C_5$-$C_7$ hydrocarbon solvent.

Embodiment 229

The varnish system of embodiment 228, wherein said solvent comprises an alcohol selected from the group consisting of ethyl alcohol, propyl alcohol (including its isomers n-propyl alcohol and isopropyl alcohol), butyl alcohol (including its isomers, namely n-butyl alcohol, sec-butyl alcohol, iso-butyl alcohol, and t-butyl alcohol), and mixtures thereof.

Embodiment 230

The varnish system of embodiment 228, wherein said solvent comprises ethanol.

Embodiment 231

The varnish system according to any one of embodiments 228-230, wherein said solvent comprises from about 40% up to about 80%, or from about 50% up to about 70%, of said second component.

Embodiment 232

The varnish system of embodiment 231, wherein said solvent comprises about 60% of said second component.

Embodiment 233

The varnish system according to any one of embodiments 207-232, wherein said first component and/or said second component comprises a flavor.

Embodiment 234

The varnish system of embodiment 233, wherein said first component and/or said second component comprises a flavor selected from the group consisting of dinoberry, menthol, peppermint, spearmint, wintergreen, anise, apricot, cinnamon, fennel, lavender, neem, ginger, vanilla, lemon, orange, spearmint, cherry, citric acid, strawberry, vanilla, coconut, bubble gum flavor, and mixtures thereof.

Embodiment 235

The varnish system according to any one of embodiments 233-234, wherein said flavor comprises from about 1% up to about 20%, or from about 5% up to about 15%, or from about 8% up to about 12% of said first component or said second component.

Embodiment 236

The varnish system of embodiment 235, wherein said flavor comprises about 11% of said first component or said second component.

Embodiment 237

The varnish system according to any one of embodiments 233-236, wherein said flavor is in said first component.

Embodiment 238

The varnish system according to any one of embodiments 233-236, wherein said flavor is in said second component.

Embodiment 239

The varnish system according to any one of embodiments 207-238, wherein said first component and/or said second component comprises an antiseptic.

Embodiment 240

The varnish system of embodiment 239, wherein said antiseptic is selected from the group consisting of alcohol, an iodophor, sodium hypochlorite, chlorhexidine, benzalkonium chloride, and cetylpyridinium chloride.

Embodiment 241

The varnish system of embodiment 239, wherein said antiseptic comprises povidone-iodine.

Embodiment 242

The varnish system according to any one of embodiments 239-241, wherein said antiseptic is in said first component.

Embodiment 243

The varnish system according to any one of embodiments 239-241, wherein said antiseptic is in said second component.

Embodiment 244

The varnish system according to any one of embodiments 207-243, wherein said first component and/or said second component comprises an antibiotic.

Embodiment 245

The varnish system of embodiment 244, wherein said antibiotic comprises an antibiotic selected from the group consisting of penicillin, tetracyclines HCl, minocycline HCl, doxycycline HCl metronidazole, ciprofloxacin, clindamycin, amoxicillin, metronidazole, combinations of amoxicillin and metronidazole, and combination of ciprofloxacin and metronidazole.

Embodiment 246

The varnish system according to any one of embodiments 244-245, wherein said antibiotic is in said first component.

Embodiment 247

The varnish system according to any one of embodiments 244-245, wherein said antibiotic is in said second component.

Embodiment 248

The varnish system according to any one of embodiments 207-247, wherein said first component and/or said second component comprises a remineralization agent.

Embodiment 249

The varnish system of embodiment 248, wherein said remineralization agent comprises an agent selected from the group consisting of hydroxyapatite, fluorapatite, Tri-Calcium Phosphate (TCP), $CaKPO_4$, $Ca_2NaK(PO_4)_2$, casein phosphopeptide/amorphous calcium phosphate, bioactive glass, ACP (calcium sulfate and dipotassium phosphate), CPP_ACP, CPP-ACFP, xylitol, and a polyphenol (e.g., proanthocyanidin (PA)).

Embodiment 250

The varnish system of embodiment 248, wherein said remineralization agent comprises xylitol.

Embodiment 251

The varnish system according to any one of embodiments 248-250, wherein said remineralization agent comprises from about 1 weight percent up to about 30 weight percent of said first component or said second component.

Embodiment 252

The varnish system according to any one of embodiments 248-250, wherein said remineralization agent comprises xylitol at about 20 weight percent of said first component or said second component.

Embodiment 253

The varnish system according to any one of embodiments 248-252, wherein said remineralization agent is in said first component.

Embodiment 254

The varnish system according to any one of embodiments 248-252, wherein said remineralization agent is in said second component.

Embodiment 255

The varnish system according to any one of embodiments 207-247, wherein combination of said first component with said second component produces a clear varnish.

Embodiment 256

The varnish system according to any one of embodiments 207-247, wherein said first component and/or said second component comprises a tint that is substantially blue, or green, or yellow, or another color.

Embodiment 257

The varnish system according to any one of embodiments 207-247, wherein said first component and/or said second component comprises a white or substantially white tint.

Embodiment 258

The varnish system of embodiment 257, wherein said tint comprises a compound selected from the group consisting of titanium oxide, zirconium oxide, germanium oxide, tin oxide, zinc oxide, iron oxide, chromium oxide, vanadium oxide, tantalum oxide, niobium oxide, and mixtures thereof.

Embodiment 259

The varnish system of embodiment 258, wherein said tint comprises titanium oxide.

Embodiment 260

The varnish system according to any one of embodiments 257-259, wherein said tint is present in said first component and/or said second component in an amount sufficient to produce a concentration in the combined varnish formulation ranging from about 0.01% weight percent, or from about 0.1% weight percent, or from about 0.5% weight percent up to about 3% weight percent, or up to about 2% weight percent, or up to about 1% weight percent.

Embodiment 261

The varnish system according to any one of embodiments 257-260, wherein said tint is in said first component.

Embodiment 262

The varnish system according to any one of embodiments 257-260, wherein said tint is in said second component.

Embodiment 263

The varnish system of embodiment 207, wherein said first component comprises or consists of NaF, sucralose, and mannitol.

Embodiment 264

The varnish system of embodiment 263, wherein said NaF comprises from about 2% up to about 50% dry weight of said first component.

Embodiment 265

The varnish system according to any one of embodiments 263-264, wherein said sucralose comprises from about 0.1% up to about 6%, or from about 0.5% up to about 2% dry weight percent of said first component.

Embodiment 266

The varnish system according to any one of embodiments 263-265, wherein said mannitol comprises from about 40% up to about 95%, or from about 50% up to about 95%, or from about 59% up to about 95% of said first component.

Embodiment 267

The varnish system of embodiment 263, wherein said first component comprises a formulation shown in Table 11.

Embodiment 268

The varnish system according to any one of embodiments 207, or 263-266, wherein said second component comprises or consists of a methacrylate and/or methacrylate ester varnish and an alcohol, optionally with a flavor.

Embodiment 269

The varnish system of embodiment 268, wherein said varnish comprises a polymer or copolymer of one or more components selected from the group consisting of dimethylaminoethyl methacrylate, butyl methacrylate, and methylmethacrylate.

Embodiment 270

The varnish system of embodiment 269, wherein said varnish comprises dimethylaminoethyl methacrylate, butyl methacrylate, and methylmethacrylate in a ratio of 2:1:1.

Embodiment 271

The varnish system according to any one of embodiments 268-270, wherein said varnish comprises 15% up to about 40% of said second component, or from about 20% up to about 30% of said second component.

Embodiment 272

The varnish system of embodiment 271, wherein said varnish comprises from about 25% up to about 30% of said second component.

Embodiment 273

The varnish system according to any one of embodiments 268-272, wherein said alcohol comprises from about 85% down to about 50% of said second component.

Embodiment 274

The varnish system according to any one of embodiments 268-273, where a flavor is present in said second component.

Embodiment 275

The varnish system according to any one of embodiments 263-267, wherein said second component comprises or consists of a formulation shown in Table 12.

Embodiment 276

A dental varnish, said varnish comprising:
a fluoride;
a bulking agent;
a methacrylate and/or methacrylate ester varnish; and
an alcohol.

Embodiment 277

The varnish of embodiment 276, wherein said dental varnish provides release of an effective amount of a fluoride for at least 1 hour after application, or for at least 2 hours after application, or for at least 4 hours after application, or for at least 6 hours after application, or for at least 8 hours after application, or for at least 12 hours after application, or for at least 24 hours after application, or for at least 48 hours after application.

Embodiment 278

The varnish according to any one of embodiments 276-277, wherein said fluoride comprises an agent selected from the group consisting of sodium fluoride, stannous fluoride, sodium monofluorophosphate, zinc hexafluorosilicate, sodium hexafluorosilicate, ammonium fluoride, calcium fluoro-phosphate ($Ca_5[F(PO_4)_3]$) or fluorapatite, fluorine-doped hydroxyapatite (e.g., $Ca_5(PO_4)_3(OH,F)$), calcium fluoride ($CaF_2$) or fluorite or fluorspar, $TiF_4$, and acidulated fluoride.

Embodiment 279

The varnish of embodiment 278, wherein said fluoride comprises sodium fluoride.

Embodiment 280

The varnish according to any one of embodiments 276-279, wherein said fluoride comprises from about 0.5% up to about 10%, or from about 0.5% up to about 5% weight percent of said varnish.

Embodiment 281

The varnish of embodiment 280, wherein said fluoride comprises about 0.5%, or about 1%, or about 2%, or about 2.5%, or about 5% weight percent of said varnish.

Embodiment 282

The varnish according to any one of embodiments 276-281, wherein said bulking agent comprise an agent selected from the group consisting of mannitol, lactose, sucrose, trehalose, sorbitol, glucose, raffinose, arginine, glycine, histidine, dextran, and polyethylene glycol.

Embodiment 283

The varnish of embodiment 282, wherein said bulking agent comprises mannitol.

Embodiment 284

The varnish according to any one of embodiments 276-283, wherein said bulking agent comprises from about 7 weight percent to about 12.5 weight percent of said final mixed varnish.

Embodiment 285

The varnish according to any one of embodiments 276-284, wherein varnish comprises a sweetener.

Embodiment 286

The varnish of embodiment 285, wherein said sweetener comprises a sweetener selected from the group consisting of sucralose, acesulfame potassium, agave nectar, aspartame, high-fructose corn syrup, sucrose, neotame, stevia, saccharin, and sugar alcohols.

Embodiment 287

The varnish of embodiment 286, wherein said sweetener comprises sucralose.

Embodiment 288

The varnish of embodiment 286, wherein said sweetener comprises a sugar alcohol selected from the group consisting of sorbitol, xylitol, and mannitol.

Embodiment 289

The varnish according to any one of embodiments 285-288, wherein said sweetener comprises from about 0.1 weight percent to about 0.6 weight percent of said final mixed varnish.

Embodiment 290

The varnish according to any one of embodiments 276-289, wherein said varnish comprises a polymer or copolymer of one or more components selected from the group consisting of acrylic acid, methacrylic acid, and their esters.

Embodiment 291

The varnish of embodiment 290, wherein said varnish comprises a polymer or copolymer of one or more components selected from the group consisting of dimethylaminoethyl methacrylate, butyl methacrylate, and methylmethacrylate.

Embodiment 292

The varnish of embodiment 291, wherein said varnish comprises a copolymer of dimethylaminoethyl methacrylate, butyl methacrylate, and methylmethacrylate in a ratio of 2:1:1.

Embodiment 293

The varnish according to any one of embodiments 276-292, wherein said varnish comprises an alcohol.

Embodiment 294

The varnish of embodiment 293, wherein said alcohol comprises ethanol.

Embodiment 295

The varnish of embodiment 294, wherein said alcohol comprises from about 40% up to about 80%, or from about 40% up to about 65%, of said varnish.

Embodiment 296

The varnish of embodiment 295, wherein said alcohol comprises about 55% of said varnish.

Embodiment 297

The varnish according to any one of embodiments 276-296, wherein said varnish comprises a flavor.

Embodiment 298

The varnish of embodiment 297, wherein said varnish comprises a flavor selected from the group consisting of dinoberry, menthol, peppermint, spearmint, wintergreen, anise, apricot, cinnamon, fennel, lavender, neem, ginger, vanilla, lemon, orange, spearmint, cherry, citric acid, strawberry, vanilla, coconut, bubble gum flavor, and mixtures thereof.

Embodiment 299

The varnish according to any one of embodiments 297-298, wherein said flavor comprises from about 1% up to about 20%, or from about 5% up to about 15%, or from about 8% up to about 12% of said varnish.

Embodiment 300

The varnish of embodiment 299, wherein said flavor comprises about 10% of said varnish.

Embodiment 301

The varnish according to any one of embodiments 276-300, wherein said varnish comprises an antiseptic.

Embodiment 302

The varnish of embodiment 301, wherein said antiseptic is selected from the group consisting of alcohol, an iodophor, sodium hypochlorite, chlorhexidine, benzalkonium chloride, cetylpyridinium chloride, benzethonium chloride, diisobutylphenoxyethoxyethyl dimethyl benzyl ammonium chloride, dodecyl trimethyl ammonium bromide, dodecyl dimethyl (2-phenoxyethyl) ammonium bromide, benzyl dimethyl stearyl ammonium chloride, and quaternized 5-amino-1,3-bis (2-ethyl-hexyl)-5-methyl hexa hydropyrimidine.

Embodiment 303

The varnish of embodiment 301, wherein said antiseptic comprises an iodophore selected from the group consisting of povidone-iodine, chlorhexidine, and cetyl pyridinium chloride.

Embodiment 304

The varnish according to any one of embodiments 276-303, wherein said first component and/or said second component comprises an antibiotic.

Embodiment 305

The varnish of embodiment 304, wherein said antibiotic comprises an antibiotic selected from the group consisting of penicillin, tetracyclines HCl, minocycline HCl, doxycycline HCl, metronidazole, ciprofloxacin, clindamycin, amoxicillin, metronidazole, combinations of amoxicillin and metronidazole, and combinations of ciprofloxacin and metronidazole.

Embodiment 306

The varnish according to any one of embodiments 276-305, wherein said varnish comprises a remineralization agent.

Embodiment 307

The varnish of embodiment 306, wherein said remineralization agent comprises an agent selected from the group consisting of hydroxyapatite, fluorapatite, Tri-Calcium Phosphate (TCP), $CaKPO_4$, $Ca_2NaK(PO_4)_2$, Casein Phosphopeptide/Amorphous Calcium Phosphate, bioactive glass, ACP (calcium sulfate and dipotassium phosphate), xylitol, and a polyphenol (e.g., proanthocyanidin (PA)).

Embodiment 308

The varnish of embodiment 306, wherein said remineralization agent comprises xylitol.

Embodiment 309

The varnish according to any one of embodiments 306-308, wherein said remineralization agent comprises from about 1 weight percent to about 30 weight percent of said varnish.

Embodiment 310

The varnish of embodiment 309, wherein said remineralization agent comprises xylitol at about 20 weight percent of said first component or said second component.

Embodiment 311

The varnish according to any one of embodiments 276-310, wherein said varnish is a clear varnish.

Embodiment 312

The varnish according to any one of embodiments 276-310, wherein said varnish comprises a white or substantially white tint.

Embodiment 313

The varnish of embodiment 312, wherein said tint comprises a compound selected from the group consisting of titanium oxide, zirconium oxide, germanium oxide, tin oxide, zinc oxide, iron oxide, chromium oxide, vanadium oxide, tantalum oxide, niobium oxide, and mixtures thereof.

Embodiment 314

The varnish of embodiment 313, wherein said tint comprises titanium oxide.

Embodiment 315

The varnish according to any one of embodiments 312-314, wherein said tint is present in said varnish in an amount ranging from about 0.01 weight percent, or from about 0.1 weight percent, or from about 0.5 weight percent up to about 3 weight percent, or up to about 2 weight percent, or up to about 1 weight percent.

Embodiment 316

The varnish of embodiment 276, wherein the formulation of said varnish comprises or consists of a formulation that would be produced by the combination of the first component with the second component as recited in any one of embodiments 207-275.

Embodiment 317

The varnish of embodiment 316, wherein the formulation of said varnish comprises or consists of the formulation that would be produced by combining the first formulation of Table 11 with a second formulation of Table 12.

Embodiment 318

The varnish according to any one of embodiments 316-317, wherein the formulation of said varnish comprises or consists of the formulation that would be produced by combining a first formulation of Table 11 with the second formulation of Table 12, where the combination ranges from about 50 mg, or from about 100 mg, or from about 125 mg, up to about 200 mg, or up to about 250 mg of the dry powder of the first component with 1 ml of the second component.

Embodiment 319

The varnish of embodiment 318, wherein the formulation of said varnish comprises or consists of the formulation that would be produced by combining about 127 mg of the dry powder of the first component with 1 mL of the second component.

Embodiment 320

A method reducing or preventing dental caries in a mammal, said method comprising:
applying to the surface of a tooth of said mammal a STAMP- or AMP-releasing varnish according to any one of embodiments 86-207; and
permitting said varnish to form a dry film on said surface of a tooth.

Embodiment 321

The method of embodiment 320, wherein said varnish kills *S. mutans*.

Embodiment 322

The according to any one of embodiments 320-321, wherein said method comprises combining a first component as recited in any one of embodiments 1-85 and 139-206 with a second component as recited in any one of embodiments 1-85 and 139-206 to form said varnish.

Embodiment 323

The method according to any one of embodiments 320-322, wherein said applying comprises application with a brush, application with a swab, application with a sponge, and application via spraying.

Embodiment 324

The method according to any one of embodiments 320-323, wherein said mammal is a non-human mammal.

Embodiment 325

The method according to any one of embodiments 320-323, wherein said mammal is a human.

Embodiment 326

The method of embodiment 325, wherein said mammal is a human infant.

Embodiment 327

The method of embodiment 325, wherein said mammal is a human child.

Embodiment 328

A method improving tooth hardness, and/or inhibiting *S. mutans*, and/or reducing dental cavities, and/or desensitizing teeth in a mammal, said method comprising:
  applying to the surface of a tooth of said mammal a fluoride-releasing varnish according to any one of embodiments 276-319; and
  permitting said varnish to form a dry film on said surface of a tooth.

Embodiment 329

The method of embodiment 328, wherein said method comprises improving tooth hardness.

Embodiment 330

The method of embodiment 328, wherein said method comprises inhibiting *S. mutans*.

Embodiment 331

The method of embodiment 328, wherein said method comprises reducing dental cavities.

Embodiment 332

The method of embodiment 328, wherein said method comprises desentizing teeth.

Embodiment 333

The according to any one of embodiments 328-332, wherein said method comprises combining a first component as recited in any one of embodiments 207-275 with a second component as recited in any one of embodiments 207-275 to form said varnish.

Embodiment 334

The method of embodiment 333, wherein said method comprises combining a first formulation of Table 11 with the second formulation of Table 12.

Embodiment 335

The method according to any one of embodiments 333-334, wherein said combining produces proportions that would be produced by combining from about 50 mg, or from about 100 mg, or from about 125 mg, up to about 200 mg, or up to about 250 mg of the dry powder of the first component with 1 ml of the second component.

Embodiment 336

The method according to any one of embodiments 333-334, wherein said combining produces proportions that would be produced by combining about 127 mg of the dry powder of the first component with 1 mL of the second component.

Embodiment 337

The method according to any one of embodiments 328-336, wherein said applying comprises application with a brush, application with a swab, application with a sponge, and application via spraying.

Embodiment 338

The method according to any one of embodiments 328-337, wherein said mammal is a non-human mammal.

Embodiment 339

The method according to any one of embodiments 328-337, wherein said mammal is a human.

Embodiment 340

The method of embodiment 339, wherein said mammal is a human infant.

Embodiment 341

The method of embodiment 339, wherein said mammal is a human child.

Embodiment 342

A dental varnish kit, said kit comprising:
  a container containing a STAMP-releasing varnish according to any one of embodiments 86-206; and/or
  a first container containing a first component of a STAMP-releasing varnish system as recited in any one of embodiments 1-85 and 139-206 and a container containing a second component of a STAMP-releasing varnish system as recited in any one of embodiments 1-85 and 139-206; and/or
  a container containing a fluoride-releasing varnish according to any one of embodiments 276-319; and/or
  a first container containing a first component of a fluoride-releasing varnish system as recited in any one of embodiments 207-275 and a container containing a second component a fluoride-releasing varnish system as recited in any one of embodiments 207-275.

Embodiment 343

The kit of embodiment 342, wherein first container comprises or consists of a first component shown in Table 11.

Embodiment 344

The kit according to any one of embodiments 342-343, wherein said second container contains a second component shown in Table 12.

Embodiment 345

The kit according to any one of embodiments 342-344, wherein said kit provides said first component and said second component in containers that produce proportions that would be produced by combining from about 50 mg, or from about 100 mg, or from about 125 mg, up to about 200 mg, or up to about 250 mg of the dry powder of the first component to about 1 ml of the second component.

Embodiment 346

The kit according to any one of embodiments 342-344, wherein said kit provides said first component and said second component in containers that produce proportions that of about 127 mg of the dry powder of the first component to about 1 mL of the second component.

Embodiment 347

The kit according to any one of embodiments 342-346, wherein said kit further comprises an applicator for application of said varnish to a tooth surface.

Embodiment 348

The kit of embodiment 347, wherein said applicator comprises an applicator selected from the group consisting of a brush, a swab, a sponge, and a sprayer.

Definitions

A "varnish" as used herein refers to a preparation comprising resinous and/or polymeric matter dissolved in a volatile solvent (e.g., oil, alcohol, water, etc.) that when applied to a surface (e.g., to the surface of a tooth) dries to form a hard more or less glossy, often transparent coating.

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

The term "peptide" as used herein refers to a polymer of amino acid residues typically ranging in length from 2 to about 50 or about 60 residues. In certain embodiments the peptide ranges in length from about 2, 3, 4, 5, 7, 9, 10, or 11 residues to about 60, 50, 45, 40, 45, 30, 25, 20, or 15 residues. In certain embodiments the peptide ranges in length from about 8, 9, 10, 11, or 12 residues to about 15, 20 or 25 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, sulfonamide or phosphoramide, carbamate or carbonate, hydroxylate, and the like (see, e.g., Spatola, (1983) *Chem. Biochem. Amino Acids and Proteins* 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "residue"" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine, ornithine, and the like. These modified amino acids are illustrative and not intended to be limiting.

"β-peptides" comprise of "β amino acids", which have their amino group bonded to the β carbon rather than the α-carbon as in the 20 standard biological amino acids. The only commonly naturally occurring β amino acid is β-alanine.

Peptoids, or N-substituted glycines, are a specific subclass of peptidomimetics. They are closely related to their natural peptide counterparts, but differ chemically in that their side chains are appended to nitrogen atoms along the molecule's backbone, rather than to the α-carbons (as they are in natural amino acids).

The terms "conventional" and "natural" as applied to peptides herein refer to peptides, constructed only from the naturally-occurring amino acids: Ala, Cys, Asp, Glu, Phe, Gly, His, Ile, Lys, Leu, Met, Asn, Pro, Gln, Arg, Ser, Thr, Val, Trp, and Tyr. A compound of the invention "corresponds" to a natural peptide if it elicits a biological activity (e.g., antimicrobial activity) related to the biological activity and/or specificity of the naturally occurring peptide. The elicited activity may be the same as, greater than or less than that of the natural peptide. In general, such a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. The following are illustrative, but non-limiting N-substituted glycine replacements: N-(1-methylprop-1-yl)glycine substituted for isoleucine (Ile), N-(prop-2-yl)glycine for valine (Val), N-benzylglycine for phenylanlaine (Phe), N-(2-hydroxyethyl)glycine for serine (Ser), and the like. In certain embodiments substitutions need not be "exact". Thus for example, in certain embodiments N-(2-hydroxyethyl)glycine may substitute for Ser, Thr, Cys, and/or Met; N-(2-methylprop-1-yl)glycine may substitute for Val, Leu, and/or Ile. In certain embodiments N-(2-hydroxyethyl)glycine can be used to substitute for Thr and Ser, despite the structural differences: the side chain in N-(2-hydroxyethyl)glycine is one methylene group longer than that of Ser, and differs from Thr in the site of hydroxy-substitution. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

Where an amino acid sequence is provided herein, L-, D-, or beta amino acid versions of the sequence are also contemplated as well as retro, inversion, and retro-inversion isoforms. In addition, conservative substitutions (e.g., in the binding peptide, and/or antimicrobial peptide, and/or linker peptide) are contemplated. Non-protein backbones, such as PEG, alkane, ethylene bridged, ester backbones, and other backbones are also contemplated. Also fragments ranging in length from about 5, 6, 7, 8, 9, 10, 11, 12, 13, 14, 15, 16, 17, 18, 19, 20, 21, 22, 23, 24, or 25 amino acids up to the full length minus one amino acid of the peptide are contemplated where the fragment retains at least 50%, preferably at least 60% 70% or 80%, more preferably at least 90%, 95%, 98%, 99%, or at least 100% of the activity (e.g., binding specificity and/or avidity, antimicrobial activity, etc.) of the full length peptide are contemplated.

A "compound antimicrobial peptide" or "compound AMP" refers to a construct comprising two or more AMPs joined together. The AMPs can be joined directly or through a linker. They can be chemically conjugated or, where joined directly together or through a peptide linker can comprise a fusion protein.

In certain embodiments, conservative substitutions of the amino acids comprising any of the sequences described herein are contemplated. In various embodiments one, two, three, four, or five different residues are substituted. The term "conservative substitution" is used to reflect amino acid substitutions that do not substantially alter the activity (e.g., antimicrobial activity and/or specificity) of the molecule. Typically conservative amino acid substitutions involve substitution one amino acid for another amino acid with similar chemical properties (e.g. charge or hydrophobicity). Certain conservative substitutions include "analog substitutions" where a standard amino acid is replaced by a non-standard (e.g., rare, synthetic, etc) amino acid differing minimally from the parental residue. Amino acid analogs are considered to be derived synthetically from the standard amino acids without sufficient change to the structure of the parent, are isomers, or are metabolite precursors. Examples of such "analog substitutions" include, but are not limited to, 1) Lys-Orn, 2) Leu-Norleucine, 3) Lys-Lys[TFA], 4) Phe-Phe[Gly], and 5) δ-amino butylglycine-ξ-amino hexylglycine, where Phe[Gly] refers to phenylglycine (a Phe derivative with a H rather than $CH_3$ component in the R group), and Lys[TFA] refers to a Lys where a negatively charged ion (e.g., TFA) is attached to the amine R group. Other conservative substitutions include "functional substitutions" where the general chemistries of the two residues are similar, and can be sufficient to mimic or partially recover the function of the native peptide. Strong functional substitutions include, but are not limited to 1) Gly/Ala, 2) Arg/Lys, 3) Ser/Tyr/Thr, 4) Leu/Ile/Val, 5) Asp/Glu, 6) Gln/Asn, and 7) Phe/Trp/Tyr, while other functional substitutions include, but are not limited to 8) Gly/Ala/Pro, 9) Tyr/His, 10) Arg/Lys/His, 11) Ser/Thr/Cys, 12) Leu/Ile/Val/Met, and 13) Met/Lys (special case under hydrophobic conditions). Various "broad conservative substations" include substitutions where amino acids replace other amino acids from the same biochemical or biophysical grouping. This is similarity at a basic level and stems from efforts to classify the original 20 natural amino acids. Such substitutions include 1) nonpolar side chains: Gly/Ala/Val/Leu/Ile/Met/Pro/Phe/Trp, and/or 2) uncharged polar side chains Ser/Thr/Asn/Gln/Tyr/Cys. In certain embodiments broad-level substitutions can also occur as paired substitutions. For example, Any hydrophilic neutral pair [Ser, Thr, Gln, Asn, Tyr, Cys]+[Ser, Thr, Gln, Asn, Tyr, Cys] can may be replaced by a charge-neutral charged pair [Arg, Lys, His]+[Asp, Glu]. The following six groups each contain amino acids that, in certain embodiments, are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W). Where amino acid sequences are disclosed herein, amino acid sequences comprising, one or more of the above-identified conservative substitutions are also contemplated.

In certain embodiments, targeting peptides, antimicrobial peptides, and/or STAMPs compromising at least 80%, preferably at least 85% or 90%, and more preferably at least 95% or 98% sequence identity with any of the sequences described herein are also contemplated. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides of this invention sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman (1981) *Adv. Appl. Math.* 2: 482, by the homology alignment algorithm of Needleman & Wunsch (1970) *J. Mol. Biol.* 48: 443, by the search for similarity method of Pearson & Lipman (1988) *Proc. Natl. Acad. Sci., USA,* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

The term "specificity" when used with respect to the antimicrobial activity of a peptide indicates that the peptide preferentially inhibits growth and/or proliferation and/or kills a particular microbial species as compared to other related and/or unrelated microbes. In certain embodiments the preferential inhibition or killing is at least 10% greater (e.g., $LD_{50}$ is 10% lower), preferably at least 20%, 30%, 40%, or 50%, more preferably at least 2-fold, at least 5-fold, or at least 10-fold greater for the target species.

The term "consisting essentially of" when used with respect to an antimicrobial peptide (AMP) or AMP motif as described herein, indicates that the peptide or peptides encompassed by the library or variants, analogues, or derivatives thereof possess substantially the same or greater antimicrobial activity and/or specificity as the referenced peptide. In certain embodiments substantially the same or greater antimicrobial activity indicates at least 80%, preferably at least 90%, and more preferably at least 95% of the antimicrobial activity of the referenced peptide(s) against a particular bacterial species (e.g., *S. mutans*).

The term "STAMP" refers to a Specifically Targeted AntiMicrobial Peptide. In various embodiments, a STAMP comprises one or more peptide targeting moieties attached to one or more antimicrobial moieties (e.g., antimicrobial peptides (AMPs)). The term C16G2 refers to a STAMP whose amino acid sequence consists of the sequence TFFRLFNRSFTQALGKGGGKNLRIIRKGIHIIKKY (SEQ ID NO:1). In various embodiments the carboxyl terminus of the sequence is amidated.

The term "simple antimicrobial peptide" or "AMP" refer to antimicrobial peptides that are not attached to a targeting moiety.

As used herein, the term "about" refers to a measurable value such as an amount, a time duration, and the like, and encompasses variations of ±20%, ±10%, ±5%, ±1%, ±0.5%, or ±0.1% from the specified value.

The term "effective amount" or "therapeutically effective amount" as used herein refers to the amount of a pharmaceutical composition comprising one or more peptides as disclosed herein or a mutant, variant, analog or derivative thereof, to decrease the level of Streptococcus mutans and prevent tooth decay, and relates to a sufficient amount of pharmacological composition to provide the desired effect. A therapeutically or prophylactically significant reduction in S. mutans is, for example, at least about 10%, at least about 20%, at least about 30%, at least about 40%, at least about 50%, at least about 60%, at least about 70%, at least about 80%, at least about 90%, at least 2 log 10, at least 3 log 10, at least 4 log 10, or at least 5 log 10 or more in CFU/mL as compared to a control or non-treated subject or the state of the subject prior to administering the oligopeptides described herein. Measured or measurable parameters can include clinically detectable markers of disease, for example, within the process of tooth decay. It will be understood, however, that the total daily usage of the compositions and formulations as disclosed herein will be decided by the attending physician or dentist within the scope of sound professional judgment.

DETAILED DESCRIPTION

Figure 1:
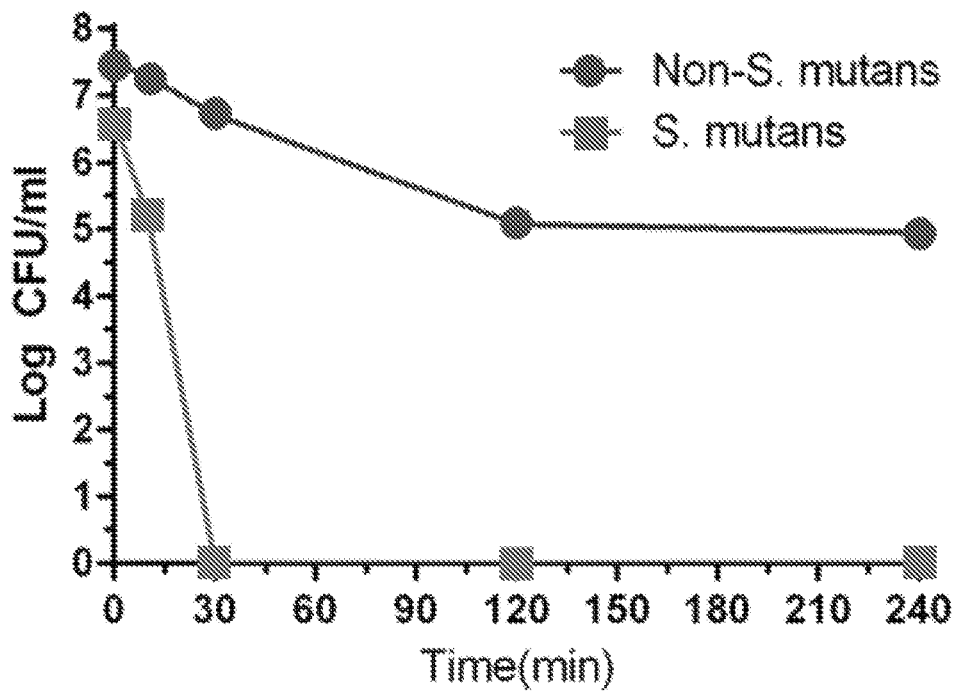
FIG. 1 illustrates the effect on a multispecies biofilm of a varnish formulation containing an antimicrobial peptide (C16G2).

In various embodiments tooth varnishes and varnish systems are provided that provide an improved fluoride release profile and/or that provide for release of an effective dose of one or more specifically targeted antimicrobial peptide(s) (STAMPS) and/or simple antimicrobial peptide(s) (AMPs) during the time a dental varnish is expected to reside on the tooth surface (e.g., a realistic maximum of about 8 hours) before sloughing off due to salivary flow and eating/drinking. In certain embodiments the tooth varnish systems comprise a first component (e.g., a first dry powder component) that contains the fluoride and/or specifically targeted antimicrobial peptide (or AMP) and a second fluid component that comprises the varnish. At the time of use, the two components are combined to produce the final varnish which is then applied to one or more tooth surfaces. The varnish quickly dries to provide a protective, fluoride-releasing and/or STAMP (or AMP) releasing coating on the tooth surface(s).

In certain embodiments the resulting dental varnish produced by the varnish systems described herein may have a transparent or white color, or a substantially transparent color having a white or off-white tint. The dental varnishes disclosed herein are capable of being transparent or substantially transparent, have a high fluoride release over an extended period of time (e.g., over a 2 hour time period, over a 4 hour time period, over a 6 hour timer period) and/or have a STAMP (or AMP) release profile that is capable of killing and/or inhibiting S. mutans in the oral cavity (e.g., on a tooth or gum surface), and is capable of being smoothly coated onto a patient's tooth.

In various embodiments the dental varnishes described herein may be applied to dried teeth using a suitable applicator, such as a brush, as is well understood by those skilled in the art. Methods of using the dental varnish to seal a tooth include applying the dental varnish to a tooth.

In various embodiments the dental varnish systems described herein comprise a first component containing a fluoride (e.g., a fluoridizing agent) or a first component containing a specifically targeted antimicrobial peptide (STAMP) or a simple antimicrobial peptide (AMP), and a second component containing a polymer, preferably a (meth)acrylate and/or (meth)acrylamide varnish. In certain embodiments the first component is provided as a dry powder, while the second component is provided as a liquid solution. In certain embodiments the two components are combined at the point and time of use to produce a dental varnish ready for application to a subject's tooth. In other embodiments the varnish is provided as a single formulation (e.g., a formulation having ingredients equivalent to a varnish produced by combination of the first and second components).

In certain illustrative, but non-limiting embodiments, the STAMP (or AMP)-releasing varnish can comprise formulations as illustrated in Table 1. As illustrated therein, in certain embodiments, the first component can be provided as a dry powder and comprises one or more STAMP(s) (e.g., C16G2), and a buffer (e.g., His), and a bulking agent (e.g., mannitol), while the second component can be provided as a liquid varnish solution (e.g., 2-propenoic acid, 2-methyl-, butyl ester, polymer with 2-(dimethylamino)ethyl 2-methyl-2-propenoate and methyl 2-methyl-2-propenoate, or EUDRAGIT® E PO (Evonik Industries)). In various embodiments the first component and/or the second component can contain one or more additional agents such as a solvent, a sweetener, a flavor, a fluoride agent, a remineralization agent, and a tint, e.g., as illustrated in Table 1 and as described below.

TABLE 1

Illustrative dental STAMP (or AMP) varnish system.

| First Component (Dry Powder) | | Second Component (Liquid) |
|---|---|---|
| One or more STAMP(s) and/or AMP(s) Bulking Agent Buffer | | Varnish solution |
| Optional Ingredients | | |
| Solvent | and/or | Solvent |
| Sweetener | and/or | Sweetener |
| Flavor | and/or | Flavor |
| Fluoride agent | and/or | Fluoride agent |
| In process pH adjuster | and/or | In process pH adjuster |
| Remineralization Agent | and/or | Remineralization Agent |
| Tint | and/or | Tint |

One particular illustrative embodiment of a STAMP-releasing dental varnish is shown in Table 2.

TABLE 2

Illustrative STAMP-releasing dental varnish.

| Component | Function | Amount per dose |
|---|---|---|
| C16G2 | Drug Substance | 13 to 60 mg |
| D-Mannitol, USP | Bulking agent | 100 to 200 mg |
| L-Histidine, USP | Buffer | 1.9 to 4 mg |
| Sucralose, NF | Flavoring Agent | 5 to 12 mg |
| Ethanol, 200 proof, USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1 |

NF = National Formulary,
q.s. = quantity sufficient;
USP = United States Pharmacopeia These components are illustrative and non-limiting and numerous variations will be available to one of skill using the teachings provided herein.

In certain embodiments of the fluoride releasing varnish, as illustrated in Table 3, the first component can be provided as a dry powder and comprises a fluoride (fluoridizing agent such as sodium fluoride) and a bulking agent (e.g., mannitol), while the second component can be provided as a liquid varnish solution (e.g., EUDRAGIT® E PO (Evonik Industries)). In various embodiments the first component and/or the second component can contain one or more additional agents such as a solvent, a sweetener, a flavor, an antiseptic, an antibiotic, a remineralization agent, and a tint, e.g., as illustrated in Table 3 and as described below.

TABLE 3

Illustrative dental fluoride varnish system.

| First Component (Dry Powder) | | Second Component (Liquid) |
|---|---|---|
| Fluoride Bulking Agent | | Varnish solution |
| Optional Ingredients | | |
| Solvent | and/or | Solvent |
| Sweetener | and/or | Sweetener |
| Flavor | and/or | Flavor |

TABLE 3-continued

Illustrative dental fluoride varnish system.

| First Component (Dry Powder) | | Second Component (Liquid) |
|---|---|---|
| Antiseptic | and/or | Antiseptic |
| Antibiotic | and/or | Antibiotic |
| Remineralization Agent | and/or | Remineralization Agent |
| Tint | and/or | Tint |

One particular illustrative embodiment of a dental varnish system is shown in Table 4. As illustrated therein the first component (provided in this example as a dry powder) contains a fluoride (fluoridizing agent such as sodium fluoride), a bulking agent, and a sweetener, while the second component contains a varnish, a solvent (e.g., an alcohol such as ethanol), and a flavor.

TABLE 4

Illustrative dental fluoride varnish system.

| First Component (Dry Powder) | | Second Component (Liquid) |
|---|---|---|
| Fluoride Bulking Agent Sweetener | | Varnish solution Solvent Flavor |
| Optional Ingredients | | |
| Flavor | and/or | Sweetener |
| Antiseptic | and/or | Antiseptic |
| Antibiotic | and/or | Antibiotic |
| Remineralization Agent | and/or | Remineralization Agent |
| Tint | and/or | Tint |

In various embodiments the first component and/or the second component can contain one or more additional agents such as a flavor, an antiseptic, an antibiotic, a remineralization agent, a tint, and the like, e.g., as illustrated in Table 4 and as described below.

These components are illustrative and non-limiting and numerous variations will be available to one of skill using the teachings provided herein.

Specifically Targeted Antimicrobial Peptide(s).

In certain embodiments the STAMP-delivering varnishes described herein contain one or more STAMPs and/or simple AMPs active at a level where upon use, the varnish promotes the benefit sought by the wearer (e.g., inhibition of *S. mutans*, decrease in caries formation, etc.) without detriment to the oral surface it is applied to.

In certain embodiments the specifically targeted antimicrobial peptide(s) incorporated into the varnishes described herein comprise a targeting peptide that binds *Streptococcus mutans*. In various embodiments the targeting peptide is attached to an antimicrobial via chemical conjugation. In other embodiments, the targeting peptide is attached directly to an antimicrobial or is attached to the antimicrobial peptide by an amino acid, or is attached to the antimicrobial peptide through a peptide linker to form a single polypeptide comprising at least one targeting domain and at least one antimicrobial domain.

In certain embodiments the STAMP is the C16G2 STAMP whose amino acid sequence consists of the sequence TFFRLFNRSFTQALGKGGGKNLRIIRKGI-HIIKKY (SEQ ID NO:2). In certain embodiments the STAMP comprises this sequence. In certain embodiments the STAMP comprises this sequence and contains 1, 2, 3, 4, 5, 6, 7, 8, 9, or 10 additional amino acids at one or both termi. The C16G2 STAMP comprises a fragment of the competence stimulating peptide (CSP) having the amino acid sequence TFFRLFNRSFTQALGK (SEQ ID NO:3) as a targeting peptide attached to the antimicrobial peptide KNLRIIRKGIHIIKKY (SEQ ID NO:4) by a Gly₃ linker. In various embodiments the peptide is amidated at the carboxyl terminus.

The STAMPs contemplated for use in the varnishes described herein are not limited to C16G2. Any of a number of targeting peptides (e.g., *S. mutans* targeting peptides) can be attached to any of a number of antimicrobial peptides, e.g., as described below.

It will be noted that in various embodiments the targeting peptide comprises a peptide that ranges in length from 5 amino acid, or from 6 amino acids, or from 7 amino acids, or from 8 amino acids up to about 50 amino acids, or up to about 40 amino acids, or up to about 30 amino acids, or up to about 20 amino acids. Similarly, in various embodiments, the antimicrobial peptide comprises a peptide that ranges in length from 5 amino acids, or from 6 amino acids, or from 7 amino acids, or from 8 amino acids, or from 9 amino acids, or from 10 amino acids up to about 100 amino acids, or up to about 80 amino acids, or up to about 60 amino acids, or up to about 50 amino acids, or up to about 40 amino acids, or up to about 30 amino acids, or up to about 20 amino acids.

Targeting Peptides that Bind *S. mutans*.

A number of peptides can be used as targeting peptides in the targeted antimicrobial peptides contemplated herein. In certain embodiments the targeting peptide is one that binds, inter alia to *S. mutans*. In certain embodiments the targeting peptide specifically binds to *S. mutans*.

Illustrative peptides that bind *S. mutans* include, but are not limited to a peptide that comprises or consists of an amino acid sequence selected from the group consisting of SGSLSTFFRLFNRSFTQALGK (CSP, SEQ ID NO:5) or a fragment thereof, EMRLSKFFRDFILQRKK (CSP1, (SEQ ID NO:6) or a fragment thereof, and EMRISRIILD-FLFLRKK (CSP2, (SEQ ID NO:7), NIFEYFLE (SEQ ID NO:8). or a fragment thereof.

In certain embodiments the targeting peptide comprises or consists of an the amino acid sequence of competence stimulating peptide (CSP) or a fragment thereof. Illustrative CSP fragments that bind *S. mutans* are shown in Table 5.

TABLE 5

Illustrative CSP fragments.

| Amino Acid Sequence | SEQ ID NO |
|---|---|
| TFFRLFNR | 9 |
| TFFRLFNRS | 10 |
| TFFRLFNRS | 11 |
| TFFRLFNRSF | 12 |
| TFFRLFNRSFT | 13 |
| TFFRLFNRSFTQ | 14 |
| TFFRLFNRSFTQA | 15 |
| TFFRLFNRSFTQAL | 16 |
| TFFRLFNRSFTQALG | 17 |
| TFFRLFNRSFTQALGK | 18 |

TABLE 5 -continued

Illustrative CSP fragments.

| Amino Acid Sequence | SEQ ID NO |
|---|---|
| STFFRLFNR | 19 |
| STFFRLFNRS | 20 |
| STFFRLFNRS | 21 |
| STFFRLFNRSF | 22 |
| STFFRLFNRSFT | 23 |
| STFFRLFNRSFTQ | 24 |
| STFFRLFNRSFTQA | 25 |
| STFFRLFNRSFTQAL | 26 |
| STFFRLFNRSFTQALG | 27 |
| STFFRLFNRSFTQALGK | 28 |
| LSTFFRLFNR | 29 |
| LSTFFRLFNRS | 30 |
| LSTFFRLFNRS | 31 |
| LSTFFRLFNRSF | 32 |
| LSTFFRLFNRSFT | 33 |
| LSTFFRLFNRSFTQ | 34 |
| LSTFFRLFNRSFTQA | 35 |
| LSTFFRLFNRSFTQAL | 36 |
| LSTFFRLFNRSFTQALG | 37 |
| LSTFFRLFNRSFTQALGK | 38 |
| SLSTFFRLFNR | 39 |
| SLSTFFRLFNRS | 40 |
| SLSTFFRLFNRS | 41 |
| SLSTFFRLFNRSF | 42 |
| SLSTFFRLFNRSFT | 43 |
| SLSTFFRLFNRSFTQ | 44 |
| SLSTFFRLFNRSFTQA | 45 |
| SLSTFFRLFNRSFTQAL | 46 |
| SLSTFFRLFNRSFTQALG | 47 |
| SLSTFFRLFNRSFTQALGK | 48 |
| GSLSTFFRLFNR | 49 |
| GSLSTFFRLFNRS | 50 |
| GSLSTFFRLFNRS | 51 |
| GSLSTFFRLFNRSF | 52 |
| GSLSTFFRLFNRSFT | 53 |
| GSLSTFFRLFNRSFTQ | 54 |
| GSLSTFFRLFNRSFTQA | 55 |
| GSLSTFFRLFNRSFTQAL | 56 |

TABLE 5 -continued

Illustrative CSP fragments.

| Amino Acid Sequence | SEQ ID NO |
|---|---|
| GSLSTFFRLFNRSFTQALG | 57 |
| GSLSTFFRLFNRSFTQALGK | 58 |
| SGSLSTFFRLFNR | 59 |
| SGSLSTFFRLFNRS | 60 |
| SGSLSTFFRLFNRS | 61 |
| SGSLSTFFRLFNRSF | 62 |
| SGSLSTFFRLFNRSFT | 63 |
| SGSLSTFFRLFNRSFTQ | 64 |
| SGSLSTFFRLFNRSFTQA | 65 |
| SGSLSTFFRLFNRSFTQAL | 66 |
| SGSLSTFFRLFNRSFTQALG | 67 |

Other suitable targeting peptides that bind *S. mutans* include, but are not limited to peptides that comprise or consist of the amino acid sequence $X^1$-$X^2$-R-R-$X^5$-$X^6$-$X^7$-R-$X^9$-$X^{10}$-$X^{11}$-$X^{12}$-$X^{13}$-$X^{14}$-$X^{15}$-$X^{16}$ (SEQ ID NO: 68) or the inverse of said amino acid sequence, wherein $X^1$ is a polar amino acid, or A; $X^2$ is F, W, Q, A, or an analog thereof; $X^5$ is a hydrophobic amino acid; $X^6$ is a hydrophobic amino acid, N, Q, or an analog thereof; $X^7$ is a polar amino acid, A, F, or an analog thereof; $X^9$ is a polar amino acid, A or an analog thereof; $X^{10}$ is a hydrophobic amino acid, Q, A, or an analog thereof; $X^{11}$ is a hydrophobic amino acid; $X^{11}$ is Q, A, or an analog thereof; $X^{11}$ is a non-polar amino acid; X14 is a hydrophobic amino acid; X15 is a non-polar amino acid, N, S, D, or an analog thereof; X16 is a polar amino acid, F, A, or an analog thereof; and said peptide ranges in length up to 100 amino acids. The peptide does not comprise or consist of the amino acid sequence of C16 (TFFRLFNRSFTQALGK (SEQ ID NO:69).

In certain embodiments, $X^1$ is a polar amino acid or A, and in certain embodiments A or T; and/or $X^2$ is F, W, Q, A, and in certain embodiments F; and/or $X^5$ is a hydrophobic amino acid in certain embodiments L or A; and in certain embodiments L; and/or $X^6$ is a hydrophobic amino acid, N or Q, in certain embodiments F, L, N, A, or Q; in certain embodiments hydrophobic; and in certain embodiments F; and/or $X^7$ is a polar amino acid, A, or F; in certain embodiments a polar amino acid or A; in certain embodiments N, A, S, D, or F; in certain embodiments N or A, and in certain embodiments N; and/or $X^9$ is a polar amino acid or A, in certain embodiments S or A, and in certain embodiments preferably S; and/or $X^{10}$ is a hydrophobic amino acid, Q, or A, in certain embodiments a hydrophobic amino acid, in certain embodiments F or L, and in certain embodiments F; $X^{11}$ is a hydrophobic amino acid, in certain embodiments T or A, and in certain embodiments T; and/or $X^{12}$ is a Q or A, and in certain embodiments Q; and/or $X^{13}$ is a non-polar amino acid, in certain embodiments P or A, and in certain embodiments preferably X; and/or $X^{14}$ is a hydrophobic amino acid, in certain embodiments L or A, and in certain embodiments L; and/or $X^{15}$ is a non-polar amino acid, N, S, or D, in certain embodiments G, A, F, N, S, or D, and in certain embodiments G or A; and/or $X^{16}$ is a polar amino acid, F, or A, in certain embodiments a polar amino acid, in certain embodiments K or Q, and in certain embodiments K.

In certain embodiments the targeting peptide comprises or consists of one or more of the amino acid sequences shown in Table 6.

TABLE 6

S. mutans targeting peptides.

| Name | Amino Acid Sequence | SEQ ID NO | % viability remaining |
|---|---|---|---|
| C16AG2 (N7, L14) | AFFRAFNRAFAQALAK | 70 | 16 |
| C16AG2 (T1) | TFFRAFARAFAQAAAK | 71 | 18 |
| C16AG2 (L14) | AFFRAFARAFAQALAK | 72 | 20 |
| C16AG2 (L5) | AFFRLFARAFAQAAAK | 73 | 21 |
| F2F6F10-L2L6L10_C16G2 | TLFRLLNRSLTQALGK | 74 | 26 |
| G15-F15_C26G2 | TFFRLFNRSFTQALFK | 75 | 29 |
| F10-L10_C16G2 | TFFRLFNRSLTQALGK | 76 | 30 |
| G15-N15_C16G2 | TFFRLFNRSFTQALNK | 77 | 30 |
| C16AG2 | AFFRAFARAFAQAAAK | 78 | 30 |
| C16AG2 (N7) | AFFRAFNRAFAQAAAK | 79 | 34 |
| G15-S15_C16G2 | TFFRLFNRSFTQALSK | 80 | 37 |
| C16AG2 (S9) | AFFRAFARSFAQAAAK | 81 | 38 |
| C16AG2 (G15) | AFFRAFARAFAQAAGK | 82 | 38 |
| C16AG2 (T11) | AFFRAFARAFTQAAAK | 83 | 39 |
| K16-Q16_C16G2 | TFFRLFNRSFTQALGQ | 84 | 42 |
| F6-L6_C16G2 | TFFRLLNRSFTQALGK | 85 | 43 |
| F2-W2_C16G2 | TWFRLFNRSFTQALGK | 86 | 45 |
| C16AG2 (F14) | AFFRAFARAFAQAFAK | 87 | 46 |
| F2 to Q2_C16G2 | TQFRLFNRSFTQALGK | 88 | 47 |
| G15-D15_C16G2 | TFFRLFNRSFTQALDK | 89 | 47 |
| G15-A15_C16G2 | TFFRLFNRSFTQALAK | 90 | 47 |
| K16-E16_C16G2 | TFFRLFNRSFTQALGE | 91 | 48 |
| N7-S7_C16G2 | TFFRLFSRSFTQALGK | 92 | 50 |
| K16-A16_C16G2 | TFFRLFNRSFTQALGA | 93 | 51 |
| N7-D7_C16G2 | TFFRLFDRSFTQALGK | 94 | 52 |
| K16-F16_C16G2 | TFFRLFNRSFTQALGF | 95 | 53 |
| C16AG2 (T1, S9, T11) | TFFRAFARSFTQAAAK | 96 | 56 |
| C16AG2 (T1, L5, S9, T11, G15) | TFFRLFARSFTQAAGK | 97 | 57 |
| ΔA13_ΔG15_C16G2 | TFFRLFNRSFTQLK | 98 | 57 |
| K16-S16_C16G2 | TFFRLFNRSFTQALGS | 99 | 59 |
| F2-L2_C16G2 | TLFRLFNRSFTQALGK | 100 | 63 |
| N7-F6/N21424 | TFFRLNFRSFTQALGK | 101 | 65 |

TABLE 6 -continued

S. mutans targeting peptides.

| Name | Amino Acid Sequence | SEQ ID NO | % viability remaining |
|---|---|---|---|
| F10 to Q10_C16G2 | TFFRLFNRSQTQALGK | 102 | 73 |
| Scan-16 | TFFRLFAAAFTQALGK | 103 | 73 |
| Scan-24 | TFFRLFNRSFTQALGK** | 104 | 75 |
| Scan-17 | TFFRLFNRSAAAALGK | 105 | 76 |
| N7-F10/N21432 | TFFRLFFRSNTQALGK*** | 106 | 76 |
| Scan-22 | TFFRLFNRSFTQPLGK | 107 | 77 |
| F2/6/10-A2/6/10_C16G2 | TAFRLANRSATQALGK | 108 | 78 |
| Scan-18 | TFFRLFNRSFTQAAAA | 109 | 78 |
| F6 to Q6_C16G2 | TFFRLQNRSFTQALGK | 110 | 79 |
| Scan-23 | TFFRLFNRSFTQALPK | 111 | 79 |
| TFF-TYY_C16G2 | TYYRLFNRSFTQALGK | 112 | 80 |
| ΔN7_C16G2 | TFFRLFRSFTQALGK | 113 | 84 |
| F7/11/15 sub Q_C16G2 | TQFRLQNRSQTQALGK | 114 | 93 |

Anti-biofilm activity level (% viability remaining for S. mutans) is shown.

Antimicrobial Peptides.

In certain embodiments, the targeting peptides described herein (e.g., peptides shown in Table 5 and Table 6) can be attached to one or more antimicrobial peptides to form selectively targeted antimicrobial peptides (STAMPS) that are incorporated into the first component of the varnish system(s) and/or the varnishes described herein. In certain embodiments the antimicrobial peptides (e.g., the AMPs described herein) are used as simple AMPs without attachment of targeting moieties. Numerous antimicrobial peptides are well known to those of skill in the art.

In certain embodiments the antimicrobial peptides comprise one or more amino acid sequences described for example below in Table 7). In certain embodiments the antimicrobial peptides comprise one or more amino acid sequences described in the "Collection of Anti-Microbial Peptides" (CAMP) an online database developed for advancement the understanding of antimicrobial peptides (see, e.g., Thomas et al. (2009) Nucleic Acids Res., 1-7.doi: 10.1093/nar/gkp1021) available at www.bicnirrh.res.in/antimicrobial.

TABLE 7

Novel antimicrobial peptides, target microorganisms and MIC values.

| ID | Organism/MIC | Sequence | SEQ ID NO |
|---|---|---|---|
| G2 | | KNLRIIRKGIHIIKKY* | 115 |
| Novispirin G10 | | KNLRRIIRKGIHIIKKYG | 116 |
| Novispirin T10 | | KNLRRIIRKTIHIIKKYG | 117 |
| Novispirin G7 | | KNLRRIGRKIIHIIKKYG | 118 |
| Novispirin T7 | | KNLRRITRKIIHIIKKYG | 119 |
| Ovispirin | | KNLRRIIRKIIHIIKKYG | 120 |
| PGG | | GLLRRLRKKIGEIFKKYG | 121 |
| Protegrin-1 | | RGGRLCYCRRRFCVCVGR* | 122 |
| K-1 | S. mutans, 25 µM | GLGRVIGRLIKQIIWRR | 123 |
| K-2 | S. mutans, 12.5 µM | VYRKRKSILKIYAKLKGWH | 124 |
| K-7 | S. mutans, 12.5 µM | NYRLVNAIFSKIFKKKFIKF | 125 |
| K-8 | S. mutans, 4 µM | KILKFLFKKVF | 126 |
| K-9 | S. mutans, 4 µM | FIRKFLKKWLL | 127 |
| K-10 | S. mutans, 4 µM | KLFKFLRKHLL | 128 |
| K-11 | S. mutans, 4 µM | KILKFLFKQVF | 129 |

TABLE 7 -continued

Novel antimicrobial peptides, target microorganisms and MIC values.

| ID | Organism/MIC | Sequence | SEQ ID NO |
|---|---|---|---|
| K-12 | S. mutans, 8 μM | KILKKLFKFVF | 130 |
| K-13 | S. mutans, 16 μM | GILKKLFTKVF | 131 |
| K-14 | S. mutans, 8 μM | LRKFLHKLF | 132 |
| K-15 | S. mutans, 4 μM | LRKNLRWLF | 133 |
| K-16 | S. mutans, 8 μM<br>P. aeruginosa, 12.5 μM<br>MRSA, 25 μM | FIRKFLQKLHL | 134 |
| K-17 | S. mutans, 8 μM | FTRKFLKFLHL | 135 |
| K-18 | S. mutans, 16 μM | KKFKKFKVLKIL | 136 |
| K-19 | S. mutans, 16 μM | LLKLLKLKKLKF | 137 |
| K-20 | S. mutans, 8 μM | FLKFLKKFFKKLKY | 138 |
| K-21 | S. mutans, 8 μM | GWLKMFKKIIGKFGKF | 139 |
| K-22 | S. mutans, 8 μM | GIFKKFVKILYKVQKL | 140 |
| 1T-88 | | GRLVLEITADEVKALGEALANAKI | 141 |
| PF-531 | A. baumannii, 25 μM<br>P. aeruginosa, 50 μM<br>T. rubrum, 50 μM<br>A. niger, 25 μM<br>B. subtilis, 25 μM<br>C. difficile, 12.5 μM<br>C. jeikeium, 6.25 μM<br>S. epidermidis, 50 μM<br>S. mutans, 12.5 μM | YIQFHLNQQPRPKVKKIKIFL | 142 |
| PF-527 | P. aeruginosa, 50 μM<br>T. rubrum, 25 μM<br>A. niger, 50 μM<br>B. subtilis, 12.5 μM<br>C. jeikeium, 6.25 μM<br>MRSA, 50 μM<br>S. epidermidis, 25 μM | GSVIKKRRKRMAKKKHRKLLKKTRIQRRRAGK | 143 |
| PF-672 | C. albicans, 1.56 μM<br>T. rubrum, 0.78 μM<br>A. niger, 3 μM<br>B. subtilis, 0.78 μM<br>E. faecalis, 3.13 μM<br>MRSA, 1.56 μM<br>S. epidermidis, 0.39 μM | MRFGSLALVAYDSAIKHSWPRPSSVRRLRM | 144 |
| PF-606 | E. coli, 50 μM<br>MRSA, 50 μM<br>S. epidermidis, 50 μM<br>S. mutans, 50 μM<br>S. pneumoniae, 50 μM | FESKILNASKELDKEKKVNTALSFNSHQDFAKAYQNGKI | 145 |
| PF-547 | T. rubrum, 25 μM<br>B. subtilis, 25 μM<br>S. mutans, 12.5 μM | WSRVPGHSDTGWKVWHRW | 146 |
| PF-006 | A. baumannii, 50 μM<br>B. subtilis, 25 μM<br>MRSA, 50 μM | MGIIAGIIKFIKGLIEKFTGK | 147 |
| PF-545 | A. niger, 50 μM<br>B. subtilis, 25 μM<br>MRSA, 50 μM | RESKLIAMADMIRRRI | 148 |
| PF-278 | C. albicans, 50 μM<br>T. rubrum, 50 μM<br>S. epidermidis, 50 μM | LSLATFAKIFMTRSNWSLKRFNRL | 149 |

TABLE 7 -continued

Novel antimicrobial peptides, target microorganisms and MIC values.

| ID | Organism/MIC | Sequence | SEQ ID NO |
|---|---|---|---|
| PF-283 | T. rubrum, 50 µM<br>B. subtilis, 50 µM<br>S. epidermidis, 50 µM | MIRIRSPTKKKLNRNSISDWKS NTSGRFFY | 150 |
| PF-307 | C. albicans, 50 µM<br>T. rubrum, 50 µM<br>B. subtilis, 50 µM | MKRRRCNWCGKLFYLEEK SK EAYCCKECRKKAKKVKK | 151 |
| PF-168 | T. rubrum, 50 µM<br>A. niger, 50 µM<br>MRSA, 50 µM | VLPFPAIPLSRRRACVAAPRPR SRQRAS | 152 |
| PF-538 | A. baumannii, 25 µM<br>C. difficile, 25 µM | KNKKQTDILEKVKEILDKKKK TKSVGQKLY | 153 |
| PF-448 | A. niger, 25 µM<br>S. pneumoniae, 50 µM | SLQSQLGPCLHDQRH | 154 |
| PF-583 | MRSA, 50 µM<br>S. epidermidis, 50 µM | KFQGEFTNIGQSYIVSASHMST SLNTGK | 155 |
| PF-600 | E. coli, 50 µM<br>S. pneumoniae, 50 µM | TKKIELKRFVD AF VKKSYENY ILERELKKLIKAINEELPTK | 156 |
| PF-525 | A. niger, 50 µM<br>S. pneumoniae, 50 µM | KF SD Q IDK GQD ALKDKLGDL | 157 |
| PF-529 | A. niger, 50 µM<br>S. pneumoniae, 50 µM | LSEMERRRLRKRA | 158 |
| PF-148 | A. niger, 50 µM<br>B. subtilis, 50 µM | RRGCTERLRRMARRNAWDLY AEHFY | 159 |
| PF-530 | A. baumannii, 25 µM | SKFKVLRKIIIKEYKGELMLSI QKQR | 160 |
| PF-522 | C. difficile, 25 µM | FELVDWLETNLGKILKSKSA | 161 |
| PF-497 | B. subtilis, 50 µM | LVLRICTDLFTFIKWTIKQRKS | 162 |
| PF-499 | B. subtilis, 50 µM | VYSFLYVLVIVRKLLSMKKRI ERL | 163 |
| PF-322 | B. subtilis, 50 µM | GIVLIGLKLIPLLANVLR | 164 |
| PF-511 | S. pneumoniae, 50 µM | VMQSLYVKPPLILVTKLAQQN | 165 |
| PF-512 | S. pneumoniae, 50 µM | SFMPEIQKNTIPTQMK | 166 |
| PF-520 | S. pneumoniae, 50 µM | LGLTAGVAYAAQPTNQPTNQ PTNQPTNQPTNQPTNQPRW | 167 |
| PF-521 | S. pneumoniae, 50 µM | CGKLLEQKNFFLKTR | 168 |
| PF-523 | S. pneumoniae, 50 µM | ASKQASKQASKQASKQASKQ ASRSLKNHLL | 169 |
| PF-524 | S. pneumoniae, 50 µM | PDAPRTCYHKPILAALSRIVVT DR | 170 |
| PF-209 | MRSA, 50 µM | NYAVVSHT | 171 |
| PF-437 | S. pneumoniae, 50 µM | FQKPFTGEEVEDFQDDDEIPTII | 172 |
| CAM135 | | GWRLIKKILRVFKGL | 173 |
| B-33 | | FKKFWKWFRRF | 174 |
| B-34 | | LKRFLKWFKRF | 175 |
| B-35 | | KLFKRWKHLFR | 176 |
| B-36 | | RLLKRFKHLFK | 177 |
| B-37 | | FKTFLKWLHRF | 178 |

TABLE 7-continued

Novel antimicrobial peptides, target microorganisms and MIC values.

| ID | Organism/MIC | Sequence | SEQ ID NO |
|---|---|---|---|
| B-38 | | IKQLLHFFQRF | 179 |
| B-39 | | KLLQTFKQIFR | 180 |
| B-40 | | RILKELKNLFK | 181 |
| B-41 | | LKQFVHFIHRF | 182 |
| B-42 | | VKTLLHIFQRF | 183 |
| B-43 | | KLVEQLKEIFR | 184 |
| B-44 | | RVLQEIKQILK | 185 |
| B-45 | | VKNLAELVHRF | 186 |
| B-46 | | ATHLLHALQRF | 187 |
| B-47 | | KLAENVKEILR | 188 |
| B-48 | | RALHEAKEALK | 189 |
| B-49 | | FHYFWHWFHRF | 190 |
| B-50 | | LYHFLHWFQRF | 191 |
| B-51 | | YLFQTWQHLFR | 192 |
| B-52 | | YLLTEFQHLFK | 193 |
| B-53 | | FKTFLQWLHRF | 194 |
| B-54 | | IKTLLHFFQRF | 195 |
| B-55 | | KLLQTFNQIFR | 196 |
| B-56 | | TILQ SLKNIFK | 197 |
| B-57 | | LKQFVKFIHRF | 198 |
| B-58 | | VKQLLKIFNRF | 199 |
| B-59 | | KLVQQLKNIFR | 200 |
| B-60 | | RVLNQVKQILK | 201 |
| B-61 | | VKKLAKLVRRF | 202 |
| B-62 | | AKRLLKVLKRF | 203 |
| B-63 | | KLAQKVKRVLR | 204 |
| B-64 | | RALKRIKHVLK | 205 |
| 1C-1 | | RRRRWWW | 206 |
| 1C-2 | | RRWWRRW | 207 |
| 1C-3 | | RRRWWWR | 208 |
| 1C-4 | | RWRWRWR | 209 |
| 2C-1 | | RRRFWWR | 210 |
| 2C-2 | | RRWWRRF* | 211 |
| 2C-3 | | RRRWWWF* | 212 |
| 2C-4 | | RWRWRWF* | 213 |
| 3C-1 | | RRRRWWK | 214 |
| 3C-2 | | RRWWRRK | 215 |

TABLE 7-continued

Novel antimicrobial peptides, target microorganisms and MIC values.

| ID | Organism/MIC | Sequence | SEQ ID NO |
|---|---|---|---|
| 3C-3 | | RRRWWWK | 216 |
| 3C-4 | | RWRWRWK | 217 |
| 4C-1 | | RRRKWWK | 218 |
| 4C-2 | | RRWKRRK | 219 |
| 4C-3 | | RRRKWWK | 220 |
| 4C-4 | | RWRKRWK | 221 |
| a-3 | | LHLLHQLLHLLHQF* | 222 |
| a-4 | | AQAAHQAAHAAHQF* | 223 |
| a-5 | | KLKKLLKKLKKLLK | 224 |
| a-6 | | LKLLKKLLKLLKKF* | 225 |
| a-7 | | LQLLKQLLKLLKQF* | 226 |
| a-8 | | AQAAKQAAKAAKQF* | 227 |
| a-9 | | RWRRWWRHFHHFFH* | 228 |
| a-10 | | KLKKLLKRWRRWWR | 229 |
| a-11 | | RWRRLLKKLHHLLH* | 230 |
| a-12 | | KLKKLLKHLHHLLH* | 231 |
| BD-1 | | FVFRHKWVWKHRFLF | 232 |
| BD-2 | | VFIHRHVWVHKHVLF | 233 |
| BD-3 | | WRWRARWRWRLRWRF | 234 |
| BD-4 | | WRIHLRARLHVKFRF | 235 |
| BD-5 | | LRIHARFKVHIRLKF | 236 |
| BD-6 | | FHIKFRVHLKVRFHF | 237 |
| BD-7 | | FHVKIHFRLHVKFHF | 238 |
| BD-8 | | LHIHAHFHVHIHLHF | 239 |
| BD-9 | | FKIHFRLKVHIRFKF | 240 |
| BD-10 | | FKAHIRFKLRVKFHF | 241 |
| BD-11 | | LKAKIKFKVKLKIKF | 242 |
| BD-12 | | WIWKHKFLHRHFLF | 243 |
| BD-13 | | VFLHRHVIKHKLVF | 244 |
| BD-14 | | FLHKHVLRHRIVF | 245 |
| BD-15 | | VFKHKIVHRHILF | 246 |
| BD-16 | | FLFKHLFLHRIFF | 247 |
| BD-17 | | LFKHILIHRVIF | 248 |
| BD-18 | | FLHKHLFKHKLF | 249 |
| BD-19 | | VFRHRFIHRHVF | 250 |
| BD-20 | | FIEIKLVHKHVLF | 251 |
| BD-21 | | VLRHLFRHRIVF | 252 |
| BD-22 | | LVHKLILRHLLF | 253 |

TABLE 7-continued

Novel antimicrobial peptides, target microorganisms and MIC values.

| ID | Organism/MIC | Sequence | SEQ ID NO |
|---|---|---|---|
| BD-23 | | VFKRVLIHKLIF | 254 |
| BD-24 | | IVRKFLFRHKVF | 255 |
| BD-25 | | VLKHVIAHKRLF | 256 |
| BD-26 | | FIRKFLFKHLF | 257 |
| BD-27 | | VIRHVWVRKLF | 258 |
| BD-28 | | FLFRHRFRHRLVF | 259 |
| BD-29 | | LFLHKHAKHKFLF | 260 |
| BD-30 | | FKHKFKHKFIF | 261 |
| BD-31 | | LRHRLRHRLIF | 262 |
| BD-32 | | LILKFLFKFVF | 263 |
| BD-33 | | VLIRILVRVIF | 264 |
| BD-34 | | FRHRFRHRF | 265 |
| BD-35 | | LKHKLKHKF | 266 |
| BD-36 | | FKFKHKLIF | 267 |
| BD-37 | | LRLRHRVLF | 268 |
| BD-38 | | FKFLFKFLF | 269 |
| BD-39 | | LRLFLRWLF | 270 |
| BD-40 | | FKFLFKHKF | 271 |
| BD-41 | | LRLFLRHRF | 272 |
| BD-42 | | FKFLFKF | 273 |
| BD-43 | | LRLFLRF | 274 |
| AA-1 | | HHFFHHFHHFFHHF* | 275 |
| AA-2 | | FHFFHHFFHFFHHF* | 276 |
| AA-3 | | KLLKGATFHFFHHFFHFFHHF | 277 |
| AA-4 | | KLLKFHFFHHFFHFFHHF | 278 |
| AA-5 | | FHFFHHFFHFFHHFKLLK | 279 |
| RIP | | YSPWTNF* | 280 |
| LL-37 | | LLGDFFRKSKEKIGKEFKRIVQRIKDFLRNLVPRTES | 281 |
| Cys-LL-37 | | CLLGDFFRKSKEKIGKEFKRIVQRIKDFLRNLVPRTES | 282 |
| LL-37(17-32) | | FKRIVQRIKDFLRNLV | 283 |
| Cys-LL-37-Cys | | CLLGDFFRKSKEKIGKEFKRIVQRIKDFLRNLVPRTESC | 284 |
| LL-37FK-13 | | FKRIVQRIKDFLR | 285 |
| LL-37FKR | | FKRIVQRIKDFLRNLVPRTES | 286 |
| LL-37GKE | | GKEFKRIVQRIKDFLRNLVPR | 287 |
| LL-37KRI | | KRIVQRIKDFLRNLVPRTES | 288 |
| LL-37LLG | | LLGDFFRKSKEKIGKEFKRIV | 289 |

TABLE 7 -continued

Novel antimicrobial peptides, target microorganisms and MIC values.

| ID | Organism/MIC | Sequence | SEQ ID NO |
|---|---|---|---|
| LL-37RKS | | RKSKEKIGKEFKRIVQRIKDFLRNLVPRTES | 290 |
| LL-37SKE | | SKEKIGKEFKRIVQRIKDFLR | 291 |
| LL-37-Cys | | LLGDFFRKSKEKIGKEFKRIVQRIKDFLRNLVPRTESC | 292 |
| BD2.21 | | KLFKFLRKHLL | 293 |
| AFS | | FLKFLKKFFKKLK | 294 |
| | | FIGAIARLLSKIFGKR | 295 |
| | | GIFSKLAGKKIKNLLISG | 296 |
| | | GIFSKLAGKKIKNLLISGLKG | 297 |
| | | GLFSKFVGKGIKNFLIKGVK | 298 |
| | | KAYSTPRCKGLFRALMCWL | 299 |
| | | KIFGAIWPLALGALKNLIK | 300 |
| | | GWGSFFKKAAHVGKHVGKAALTHYL | 301 |
| | | RGLRRLGRKIAHGVKKYG | 302 |
| | | RGLRRLGRKIAHGVKKYGPTVLRIIRIAG | 303 |
| | | KIAHGVKKYGPTVLRIIR | 304 |
| | | LLGDFFRKSKEKIGKEFKRIVQRIKDFLRNLVPRTES | 305 |
| | | FLPLIGRVLSGIL | 306 |
| | | IGKFLKKAKKFGKAFVKILKK | 307 |
| | | GKFLKKAKKFGKAFVKIL | 308 |
| | | WFLKFLKKFFKKLKY | 309 |
| | | RGLRRLGRKIAHGVKKY | 310 |
| | | LLGDFFRKSKEKI | 311 |
| | | ILRWPWWPWRRK | 312 |
| | | KLFGALWPLALGALKNLLK | 313 |

A number of antimicrobial peptides are also disclosed in U.S. Pat. Nos. 7,271,239, 7,223,840, 7,176,276, 6,809,181, 6,699,689, 6,420,116, 6,358,921, 6,316,594, 6,235,973, 6,183,992, 6,143,498, 6,042,848, 6,040,291, 5,936,063, 5,830,993, 5,428,016, 5,424,396, 5,032,574, 4,623,733, which are incorporated herein by reference for the disclosure of particular antimicrobial peptides.

In certain embodiments the antimicrobial peptides comprise one or more amino acid sequences described in the "Collection of Anti-Microbial Peptides" (CAMP) an online database developed for advancement the understanding of antimicrobial peptides (see, e.g., Thomas et al. (2009) Nucleic Acids Res., 2009, 1-7.doi:10.1093/nar/gkp1021) available at www.bicnirrh.res.in/antimicrobial.

In certain embodiments, the antimicrobial peptide is a novaspririn, a novaspirin fragment or analog, e.g., as shown above in Table 7. In certain embodiments constructs are contemplated where one or more of the targeting peptides described herein are attached (e.g., directly or through a linker) to a modulated version of novispirin G10 designated G2 (KNLRIIRKGIHIIKKY (SEQ ID NO:314). In this case, the C terminal amino acids can be removed and an internal arginine can be eliminated to facilitate chemical synthesis. Novispirin G10 (the "parent molecule") is an antimicrobial alpha-helical octadecapeptide structurally related to cathelicidins and other innate immunity peptides.

Joining Targeting Peptides to Antimicrobial Peptides.

Chemical Conjugation.

In certain embodiments the targeting peptides are attached directly to the antimicrobial peptides antimicrobial peptides via naturally occurring reactive groups or the targeting peptide(s) and/or the antimicrobial peptides can be functionalized to provide such reactive groups.

In various embodiments the targeting peptides are attached to the antimicrobial peptides via one or more linking agents. Thus, in various embodiments the targeting peptides and the antimicrobial peptides can be conjugated via a single linking agent or multiple linking agents. For example, the targeting peptide and the antimicrobial peptide can be conjugated via a single multifunctional (e.g., bi-, tri-, or tetra-) linking agent or a pair of complementary linking agents. In another embodiment, the targeting peptide and the antimicrobial peptides are conjugated via two, three, or more linking agents. Suitable linking agents include, but are not limited to, e.g., functional groups, affinity agents, stabilizing groups, and combinations thereof.

In certain embodiments the linking agent is or comprises a functional group. Functional groups include monofunctional linkers comprising a reactive group as well as multifunctional crosslinkers comprising two or more reactive groups capable of forming a bond with two or more different functional targets (e.g., labels, proteins, macromolecules, semiconductor nanocrystals, or substrate). In some preferred embodiments, the multifunctional crosslinkers are heterobifunctional crosslinkers comprising two or more different reactive groups.

Suitable reactive groups include, but are not limited to thiol (—SH), carboxylate (COOH), carboxyl (—COOH), carbonyl, amine (NH$_2$), hydroxyl (—OH), aldehyde (—CHO), alcohol (ROH), ketone (R$_2$CO), active hydrogen, ester, sulfhydryl (SH), phosphate (—PO$_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyl-diimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful in forming chimeric moieties (targeted antimicrobial peptides) include those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) *Advanced Organic Chemistry*, 3rd Ed., John Wiley & Sons, New York, Hermanson (1996) *Bioconjugate Techniques*, Academic Press, San Diego; and Feeney et al. (1982) *Modification of Proteins; Advances in Chemistry Series*, Vol. 198, American Chemical Society, Washington, D.C.

A "linker" or "linking agent" as used herein, is a molecule that is used to join two or more molecules. In certain embodiments the linker is typically capable of forming covalent bonds to both molecule(s) (e.g., the targeting peptide and the antimicrobial peptide). Suitable linkers are well known to those of skill in the art and include, but are not limited to, straight or branched-chain carbon linkers, heterocyclic carbon linkers, or peptide linkers. In certain embodiments the linkers can be joined to the constituent amino acids through their side groups (e.g., through a disulfide linkage to cysteine). However, in certain embodiments, the linkers will be joined to the alpha carbon amino and carboxyl groups of the terminal amino acids.

A bifunctional linker having one functional group reactive with a group on one molecule (e.g., a targeting peptide), and another group reactive on the other molecule (e.g., an antimicrobial peptide), can be used to form the desired conjugate. Alternatively, derivatization can be performed to provide functional groups. Thus, for example, procedures for the generation of free sulfhydryl groups on peptides are also known (See U.S. Pat. No. 4,659,839).

In certain embodiments the linking agent is a heterobifunctional crosslinker comprising two or more different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In one embodiment, the heterobifunctional crosslinker is SMCC.

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680, 338; 4,569,789; and 4,589,071; and Borlinghaus et al. (1987) *Cancer Res.* 47: 4071-4075).

Fusion Proteins.

In certain embodiments the targeted antimicrobial peptide can be chemically synthesized or expressed as a recombinant fusion protein (i.e., a chimeric fusion protein).

In certain embodiments the chimeric fusion proteins are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151;

the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding targeted antimicrobial peptides may be cloned using DNA amplification methods such as polymerase chain reaction (PCR). Thus, for example, the nucleic acid encoding a targeting peptide is PCR amplified, using a sense primer containing the restriction site for NdeI and an antisense primer containing the restriction site for HindIII. This produces a nucleic acid encoding the targeting sequence and having terminal restriction sites. Similarly nucleic acids encoding an antimicrobial peptide and/or antimicrobial peptide/linker/spacer can be provided having complementary restriction sites. Ligation of sequences and insertion into a vector produces a vector encoding the fusion protein.

While the targeting peptides and AMPS can be directly joined together, one of skill will appreciate that they can be separated by a peptide spacer/linker consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli,* other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification,* Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J Biol. Chem.,* 268: 14065-14070; Kreitman and Pastan (1993) *Bioconjug. Chem.,* 4: 581-585; and Buchner, et al. (1992) *Anal. Biochem.,* 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

As indicated above, in various embodiments an amino acid, or a peptide linker/spacer is used to join the one or more targeting peptides to one or more antimicrobial peptide(s). In various embodiments the peptide linker is relatively short, typically less than about 10 amino acids, preferably less than about 8 amino acids and more preferably about 1 or to or 3 to about 5 amino acids. Suitable illustrative linkers include, but are not limited to PSGSP ((SEQ ID NO:315), ASASA (SEQ ID NO: 316), or GGG. In certain embodiments longer linkers such as (GGGGS)3 (SEQ ID NO:317) can be used. Illustrative linking amino acids and peptide linkers and other linkers are shown in Table 8.

TABLE 8

Illustrative peptide and non-peptide linkers.

| Linker | SEQ ID NO: |
|---|---|
| P | |
| S | |
| G | |
| AAA | |
| GGG | |
| SGG | |
| SAT | |
| PYP | |
| ASA | |
| GGGG | 318 |
| PSPSP | 319 |
| PSPSP | 320 |
| KKKK | 321 |

TABLE 8-continued

Illustrative peptide and non-peptide linkers.

| Linker | SEQ ID NO: |
|---|---|
| RRRR | 322 |
| ASASA | 323 |
| GGSGGS | 324 |
| GGGGS | 325 |
| GGGGS GGGGS | 326 |
| GGGGS GGGGS GGGGS | 327 |
| GGGGS GGGGS GGGGS GGGGS | 328 |
| GGGGS GGGGS GGGGS GGGGS GGGGS | 329 |
| GGGGS GGGGS GGGGS GGGGS GGGGS GGGGS | 330 |
| 2-nitrobenzene or O-nitrobenzyl | |
| Nitropyridyl disulfide | |
| Dioleoylphosphatidylethanolamine (DOPE) | |
| S-acetylmercaptosuccinic acid | |
| 1,4,7,10-tetraazacyclododecane-1,4,7,10-tetracetic acid (DOTA) | |
| β-glucuronide and β-glucuronide variants | |
| Poly(alkylacrylic acid) | |
| Benzene-based linkers (for example: 2,5-Bis(hexyloxy)-1,4-bis[2,5-bis(hexyloxy)-4-formyl-phenylenevinylene]benzene) and like molecules | |
| Disulfide linkages | |
| Poly(amidoamine) or like dendrimers linking multiple target and killing peptides in one molecule | |
| Carbon nanotubes | |
| Hydrazone and hydrazone variant linkers | |
| PEG of any chain length | |
| Succinate, formate, acetate butyrate, other like organic acids | |
| Aldols, alcohols, or enols | |
| Peroxides | |
| alkane or alkene groups of any chain length | |
| One or more porphyrin or dye molecules containing free amide and carboxylic acid groups | |
| One or more DNA orR NA nucleotides, including polyamine and polycarboxyl-containing variants | |

TABLE 8-continued

Illustrative peptide and non-peptide linkers.

| Linker | SEQ ID NO: |
|---|---|
| Inulin, sucrose, glucose, or other single, di or polysaccharides | |
| Linoleic acid or other polyunsaturated fatty acids | |
| Variants of any of the above linkers containing halogen or thiol groups | |

(In various embodiments any of the amino-acid-based linkers could be L peptides, D peptides, combinations of L and D residues, β-peptides, and the like).

Multiple Targeting Peptides and/or AMPs.

As indicated above, in certain embodiments, the chimeric moieties described herein can comprise multiple targeting peptides attached to a single antimicrobial peptide or multiple antimicrobial peptides attached to a single targeting peptide, or multiple targeting peptides attached to multiple antimicrobial peptides.

Where the chimeric construct is a fusion protein this is easily accomplished by providing multiple domains that are targeting domains attached to one or more antimicrobial peptide domains. In various embodiments the multiple targeting domains and/or multiple effector domains can be attached to each other directly or can be separated by linkers (e.g., amino acid or peptide linkers as described above).

When the chimeric construct is a chemical conjugate linear or branched configurations are readily produced by using branched or multifunctional linkers and/or a plurality of different linkers.

Protecting Groups.

While the various peptides described herein may be shown with no protecting groups, in certain embodiments they can bear one, two, three, four, or more protecting groups. In various embodiments, the protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus.

Fluoride (Fluoridizing Agent)

In various embodiments, fluoride (fluoridizing) agents suitable for use in the dental varnishes described herein include, but are not limited to sodium fluoride, stannous fluoride, sodium monofluorophosphate, zinc hexafluorosilicate, and sodium hexafluorosilicate, ammonium fluoride, calcium fluoro-phosphate ($Ca_5[F(PO_4)_3]$) or fluorapatite, fluorine-doped hydroxyapatite (e.g., $Ca_5(PO_4)_3(OH,F)$, calcium fluoride ($CaF_2$) or fluorite or fluorspar, diofluorisilane, $TiF_4$, and acidulated fluoride. In certain embodiments the fluoridizing agent may be present in the dental varnish in amounts of from about 0.1 weight percent to about 10 weight percent, such as from about 1 weight percent to about 7.5 weight percent or from about 2 weight percent to about 6 weight percent of the dental varnish (e.g., after combination of the first component with the second component. In certain embodiments the fluoride agent comprises about 0.5 weight percent, or about 1 weight percent, or about 2.5 weight percent, or about 5 weight percent of the varnish.

Bulking Agent

In various embodiments the dental varnishes described herein can comprise a bulking agent that may be provided in the first component or the second component, or in both components. In certain embodiments the bulking agent (e.g., mannitol) is provided in the first component.

Illustrative bulking agents include, but are not limited to, mannitol, lactose, sucrose, trehalose, sorbitol, glucose, raffinose, arginine, glycine, histidine, dextran, erythritol, glycylglycine, glycine, histidine, polyethylene glycol, and combinations thereof.

In various embodiments the bulking agent may be present in the dental varnish in amounts of from about 1 weight percent to about 95 weight percent, such as from about 5 weight percent to about 35 weight percent, or from about 8 weight percent to about 30 weight percent, or from about 7 weight percent up to about 12 weight percent. In certain embodiments the bulking agent comprises about 8.5 weight percent of the dental varnish (e.g., after combination of the first component with the second component).

Varnish

In various embodiments the dental varnishes and varnish systems described herein typically comprise a polymerized varnish that is comprised of polymer monomers that when said polymerized varnish is applied to the tooth surface forms a dry varnish coating on the tooth surface. In certain embodiments the varnish comprises one, two, three, or a plurality of, or all the plurality of polymer monomers selected from the group of (meth)acrylates and methacrylate esters. Illustrative monomers include, but are not limited to, ethylene glycol dimethacrylate, hydroxyethyl methacrylate (HEMA), and the like.

In certain embodiments the varnish systems and varnishes comprises dimethylaminoethyl methacrylate, butyl methacrylate, and methylmethacrylate. In certain embodiments the varnish comprises dimethylaminoethyl methacrylate, butyl methacrylate, and methylmethacrylate in a ratio of 2:1:1 (also known as poly(butyl methacrylate-co-(2-dimethylaminoethyl) methacrylate-co-methyl methacrylate) 1:2:1, CAS NO: 24938-16-7). This formulation is commercially available as EUDRAGIT® E PO (Evonik Industries).

In various embodiments the varnish polymers may be present in the dental varnish formulation in amounts of from about 5 weight percent to 90 weight percent, such as from about 10 weight percent to about 50 weight percent or from about 12 weight percent to about 35 weight percent (e.g., after combination of the first component with the second component). In certain embodiments the varnish comprises about 26 weight percent of the dental varnish formulation (e.g., after combination of the first component with the second component).

Solvent

In various embodiments the dental varnishes and varnish systems described herein can comprise a solvent that may be provided in the first component, in the second component, or in both components. In certain embodiments the solvent (e.g., ethanol, acetone, or ethyl acetate, or similar solvents known by those skilled in the art) is provided in the second component along with the varnish.

Illustrative solvents suitable for use in the dental varnish systems and varnishes described herein include one or more alcohols, one or more hydrocarbons, ketones, esters, or combinations thereof. In some embodiments, the solvent comprises a mixture of alcohol and hydrocarbons. In various embodiments the dental varnish formulations may include individual solvents (e.g. ethyl alcohol only) or mixtures of alcohols, individual hydrocarbons or their mixtures, or mixtures of alcohols with hydrocarbons.

Alcohols suitable for use in the dental varnish systems and varnishes described herein include, but are not limited to, $C_2$-$C_4$ alcohols, including $C_3$ alcohols, wherein said alcohols may be linear, branched and/or cyclic. Alcohols include ethyl alcohol, propyl alcohol (including its isomers n-propyl alcohol and isopropyl alcohol), butyl alcohol (including its isomers, namely n-butyl alcohol, sec-butyl alcohol, iso-butyl alcohol, and t-butyl alcohol), and blends thereof. In certain embodiments the use of alcohols outside the $C_2$-$C_4$ range is also contemplated. In certain embodiments the solvent comprises or consists of ethyl alcohol.

Suitable hydrocarbons include, but are not limited to, $C_5$-$C_7$ hydrocarbons, wherein the hydrocarbons may be linear, branched and/or cyclic, and may be alkanes and/or alkenes. A hydrocarbon component may comprise a single hydrocarbon or a blend of two or more hydrocarbons. Specific suitable hydrocarbons include, but are not limited to isopentane, n-pentane, n-hexane, isohexanes, cyclohexene, cyclohexane, methylcyclopentane, n-heptane, methyl cyclohexane, 2,5-dimethylhexane, cyclohexene, methyl cyclohexene, 1-heptene, and mixtures thereof. In certain embodiments the use of hydrocarbons outside the $C_5$-$C_7$ range is also contemplated.

In various embodiments the solvent may be present in the dental varnish systems and varnishes in amounts of from about 10 weight percent to about 90 weight percent, such as from about 20 weight percent to about 80 weight percent or from about 50 weight percent to about 75 weight percent. In certain embodiments where the solvent comprises hexane, the solvent may be present in an amount ranging from about 1 weight percent or from about 10 weight percent up to about 15 weight percent, where the solvent comprises alcohol, the solvent may be present in an amount ranging from about 1 weight percent or from about 10 weight percent up to about 84 weight percent, or up to about 50 weight percent, or up to about 30 weight percent, or up to about 25 weight percent, or up to about 15 weight percent, or in certain embodiments from about 1 weight percent up to about 15 weight percent, or from about 10 weight percent up to about 25 weight percent, or from about 20 weight percent up to about 30 weight percent. In certain embodiments the solvent comprises about 55 weight percent of the dental varnish (e.g., after combination of the first component with the second component.

Sweetener

In various embodiments the dental varnish systems and varnishes disclosed herein may include one or more sweeteners. The sweeteners can be provided in the first component or in the second component, or in both components. In certain embodiments the sweetener (e.g., sucralose) is provided in the first component.

Illustrative sweeteners include, but are not limited to, sucralose, xylitol, sorbitol, aspartame, sodium saccharin, acesulfame potassium (potassium salt of 6-methyl-1,2,3-oxathiazin-4(3H)-one-dioxide), and mixtures thereof. Such sweeteners may be in the dental varnish in amounts of from about 0.01 weight percent to about 4 weight percent, such as from about 0.05 weight percent to about 1 weight percent, or from about 0.1 weight percent up to about 0.5 weight percent or up to about 1.5 weight percent or from about 0.1 weight percent to about 1 weight percent.

Flavor

In various embodiments the dental varnish systems and varnishes disclosed herein may include one or more flavors.

The flavors can be provided in the first component or in the second component, or in both components. In certain embodiments the flavor (e.g., dinoberry) is provided in the second component (e.g., in the varnish solution).

Illustrative flavors include, but are not limited to, dinoberry, menthol, peppermint, spearmint, wintergreen, anise, apricot, cinnamon, fennel, lavender, neem, ginger, vanilla, lemon, orange, spearmint, cherry, citric acid, strawberry, vanilla, coconut, bubble gum flavor, and mixtures thereof.

In various embodiments the flavors (flavoring additives) may be in the dental varnish in amounts of from about 0.1 weight percent to about 20 weight percent, such as from about 1 weight percent to about 15 weight percent or from about 7 weight percent to about 13 weight percent of the dental varnish (e.g., after combination of the first component with the second component).

Antiseptic Agents.

In various embodiments the dental varnish systems and varnishes disclosed herein may include one or more antiseptic agents. When present, the antiseptic agent(s) can be provided in the first component or in the second component, or in both components.

As used herein, the term "antiseptic agent" includes both bactericidal and bacteriostatic agents. Such an agent can be an anti-plaque agent and/or an anti-caries agent, if, when provided in an effective amount to a recipient, it is capable of preventing or attenuating the accumulation of plaque or caries. A variety of antiseptic agents can be utilized in the dental varnishes described herein.

Illustrative, but non-limiting antiseptics include the cationic nitrogen-containing antibacterial materials that are well known to the art (see, e.g., the section on "Quaternary Ammonium and Related Compounds" in the article on "Antiseptics and Disinfectants" in Kirk-Othmer Encyclopedia of Chemical Technology, 2nd ed. (Vol. 2, pp. 632-6455). Such materials have been used in oral compositions to counter plaque formation caused by bacteria in the oral cavity. Among the most common and efficacious of these antibacterial, antiplaque quaternary ammonium compounds are cetylpyridinium chloride and benzalkonium chloride. Other cationic ammonium antibacterial agents of this type are described in U.S. Pat. Nos. 2,984,639, 3,325,402, 3,431,208, 3,703,583, and 4,339,430, British Patent No. 1,319,396, and German Patent No. 2,332,383, which are incorporated herein by reference for the antibacterial/antiseptic agents described therein.

In certain embodiments the antiseptic agent comprises an agent selected from the group consisting of alcohol, an iodophor, sodium hypochlorite, chlorhexidine, benzalkonium chloride, cetylpyridinium chloride, benzethonium chloride, diisobutylphenoxyethoxyethyl dimethyl benzyl ammonium chloride, dodecyl trimethyl ammonium bromide, dodecyl dimethyl (2-phenoxyethyl) ammonium bromide, benzyl dimethyl stearyl ammonium chloride, cetyl pyridinium chloride, and quaternized 5-amino-1,3-bis (2-ethyl-hexyl)-5-methyl hexa hydropyrimidine.

In certain embodiments the antiseptic agent comprises an iodophor such as povidone iodine.

In certain embodiments the antiseptic agent comprises cetylpyridinium chloride, which is efficacious, compatible with the other components of the dental varnish, and inexpensive.

In various embodiments the antiseptic agent may be present in the dental varnish in amounts of from about 0.01 weight percent up to about 35 weight percent, or up to about 20 weight percent, or up to about 15 weight percent, or up to about 10 weight percent, such as from about 0.05 weight percent to about 5 weight percent or from about 0.1 weight percent to about 3 weight percent (e.g., after combination of the first component with the second component). In certain embodiments the antiseptic agent comprises about 1 weight percent of the dental varnish (e.g., after combination of the first component with the second component).

Antibiotic

In various embodiments the dental varnish systems and varnishes disclosed herein may include one or more antibiotics. When present, the antibiotic(s) can be provided in the first component or in the second component, or in both components.

Illustrative antibiotics include, but are not limited to penicillins, tetracyclines (e.g., tetracycline HCl), minocycline, doxycycline, metronidazole, ciprofloxacin, clindamycin, amoxicillin, metronidazole, combinations of amoxicillin-metronidazole, combinations of ciprofloxacin-metronidazole, and the like.

In various embodiments the antibiotic may be present in the dental varnish in amounts of from about 2 weight percent to about 30 weight percent, such as from about 10 weight percent to about 25 weight percent or from about 20 weight percent to about 25 weight percent (e.g., after combination of the first component with the second component). In certain embodiments the antibiotic comprises about 21.4 weight percent of the dental varnish (e.g., after combination of the first component with the second component).

Remineralization Agent(s).

In various embodiments the dental varnish systems and varnishes disclosed herein may include one or more remineralization agents to aid remineralization and/or tooth hardness. When present, the remineralization agent(s) can be provided in the first component or in the second component, or in both components.

Illustrative remineralization agents include, but are not limited to, hydroxyapatite, fluorapatite, Tri-Calcium Phosphate (TCP), $CaKPO_4$, $Ca_2NaK(PO_4)_2$, casein phosphopeptide/amorphous calcium phosphate, bioactive glass, ACP (calcium sulfate and dipotassium phosphate), xylitol, and a polyphenol (e.g., proanthocyanidin (PA).

Tri-Calcium phosphate (TCP) is a hybrid material created with a milling technique that fuses beta tricalcium phosphate and sodium lauryl sulfate or fumaric acid. This blending results in a "functionalized" calcium and a "free" phosphate, designed to increase the efficacy of fluoride remineralization. TCP provides catalytic amounts of calcium to boost fluoride efficacy and can coexist with fluoride in a dental varnish as contemplated herein.

In casein phosphopeptide/amorphous calcium phosphate remineralization agents, casein phosphopeptides (CPPs) are typically produced from the tryptic digest of casein, aggregated with calcium phosphate and purified through ultrafiltration. Casein has the ability to stabilize calcium and phosphate ions by releasing small sequences of casein phosphopeptides (CPPs) through partial enzymic digestion that led to the development of a remineralization technology based on casein phosphopeptide-stabilized amorphous calcium phosphate complexes (CPP-ACP) and casein phosphopeptide-stabilized amorphous calcium fluoride phosphate complexes (CPP-ACFP).

The ACP technology utilizes a two-phase delivery system to keep the calcium and phosphorous components from reacting with each other before use. Accordingly, the two phases of the ACP technology can be incorporated into the two components comprising the dental varnish systems described herein. Current sources of calcium and phosphorous are two salts, calcium sulfate and dipotassium phosphate. When the two salts are mixed, they rapidly form ACP that can precipitate on to the tooth surface. This precipitated ACP can then readily dissolve into the saliva and can be available for tooth remineralization.

Bioactive glass (BIOGLASS®) acts as a biomimetic mineralizer matching the body's own mineralizing traits while also affecting cell signals in a way that benefits the restoration of tissue structure and function. Bioglass® in an aqueous environment immediately begins surface reaction in three phases, leaching and exchange of cations, network dissolution of $SiO_2$ and precipitation of calcium and phosphate to form an apatite layer. The critical stages for glass surface reactions, the initial $Na^+$ and $H^+/H_3O^+$ ion exchange and de-alkalinization of the glass surface layer are quite rapid, within minutes of implantation and exposure to body fluids. The net negative charge on the surface and loss of sodium causes localized breakdown of the silica network with the resultant formation of silanol (SiOH) groups, which then repolymerize into a silica-rich surface layer. Within 3-6 h in vitro, the calcium phosphate layer will crystallize into the carbonated hydroxyapatite (CAP) layer, which is essentially the bonding layer. Chemically and structurally, this apatite is nearly identical to bone and tooth mineral. Bioactive glass formulations commonly used contain 45 wt % $SiO_2$ 4.5 wt % $Na_2O$ and CaO and 6 wt % $P_2O_5$. NOVAMIN®, a trade name for bioactive glass, is manufactured by Novamin Technologies Inc. (Alachua, Fla., USA). It has been demonstrated that fine particulate bioactive glasses (<90 μm) incorporated into an aqueous dentifrice have the ability to clinically reduce the tooth hypersensitivity through the occlusion of dentinal tubules by the formation of the CAP layer.

In certain embodiments, peptides or proteins comprising repeats of the tripeptides DSS or ESS can be incorporated into the first or second component of the varnish. Proteins and peptides containing DSS-like repeats are involved in the rebuilding of tooth structure, such as remineralization of enamel and rebuilding of dentin. Synthetic peptides comprising DSS or ESS repeats are contemplated, as well as proteins that contain these sequence repeats, such as dentin sialophosphoprotein and dentin phosphoprotein.

In certain embodiments, a combination of arginine and insoluble calcium compounds can be present in the first or second component of the varnish. Arginine-calcium carbonate compounds have been shown to occlude exposed dentinal tubules and reduce dental sensitivity, and may contribute to enamel remineralization. In certain embodiments, the amount of arginine-calcium carbonate is from about 1 to 10%, or about 8% by weight.

Xylitol is a non-cariogenic five-carbon sugar alcohol that occurs naturally in plants and is used as a substitute for sugar. Xylitol has the ability to reduce dental plaque formation, make plaque less adhesive, neutralize plaque acids by decreasing the production of lactic acid, reduce the levels of *S. mutans*, reduce cavities by up to 80%, demonstrate significant long-term reduction in caries (88-93%), assist in the remineralization of tooth enamel, reduce gum tissue inflammation, and help with dry mouth and bad breath.

In certain embodiments, antibacterial or antiseptic with general positive charge can be incorporated into the first or second component. This agents include but are not limited to chlorhexidine, cetylpyridimium chloride, positively charged antimicrobial nanoparticles, and polyhexamethylene biguanide (PHMB). The cationic character of these agents allows for rapid release from the varnish during use.

It has been suggested that the preservation and stability of dentin collagen may be essential during the remineralization process, because it acts as a scaffold for mineral deposition. It has also been suggested that the presence of an organic matrix may reduce the progression of erosion in dentin. One of the important strategies regarding preventive therapies for root caries is to promote remineralization of demineralized dentin.

Polyphenols are plant-derived substances that have antioxidant and anti-inflammatory properties. They are believed to interact with microbial membrane proteins, enzymes and lipids, thereby altering cell permeability and permitting the loss of proteins, ions and macromolecules. One such polyphenol is proanthocyanidin (PA), which is a bioflavanoid-containing benzene-pyran-phenolic acid molecular nucleus. The PA accelerates the conversion of soluble collagen to insoluble collagen during development and increases collagen synthesis to potentially aid in the remineralization of demineralized dentin.

The foregoing remineralization agents are illustrative and non-limiting. Numerous other remineralization agents are known and can readily be incorporated into the varnish systems described herein.

In various embodiments the remineralization agent(s) may be present in the dental varnish in amounts of from about 1 weight percent to about 20 weight percent, or up to about 15 weight percent, or up to about 10 weight percent, or up to about 5 weight percent, such as from about 2 weight percent up to about 5 weight percent (e.g., after combination of the first component with the second component). In certain embodiments the remineralization agent(s) comprise about 2 weight percent of the dental varnish (e.g., after combination of the first component with the second component). In certain embodiments CPP-ACT is present in the dental varnish at about 1 weight percent up to about 2 weight percent. In certain embodiments TCP is present at about 5 weight percent or less. In certain embodiments xylitol (when used as a remineralization is present at about 1 weight percent or about 2 weight percent or about 5 weight percent up to about 30 weight percent. In certain embodiments xylitol is present at about 20 weight percent.

Oxide/Tint

In embodiments, the dental varnish systems and varnishes disclosed herein may be clear or substantially transparent. In alternative embodiments, the dental varnish may include a white or substantially white tint. In further alternative embodiments, the formulation may include blue, green, yellow, or other colored tints. Where a tint is present, the tint can be provided in the first component, in the second component, or in both components.

In certain embodiments when the dental varnish systems or varnishes has such a tint, the varnish will include a tint selected from the group consisting of titanium oxide, zirconium oxide, germanium oxide, tin oxide, zinc oxide, iron oxide, chromium oxide, vanadium oxide, tantalum oxide, niobium oxide, and mixtures thereof. In certain embodiments, the oxide may be present in the dental varnish (e.g., in a varnish produced by combination of the first component with the second component) in amounts of from about 0.01 weight percent to about 3 weight percent or to about 2 weight percent, such as from about 0.01 weight percent to about 1 weight percent or from about 0.08 weight percent to about 1 weight percent.

In certain embodiments where the varnish is provided by the combination of two components, the tint can be provided in the first component or in the second component.

Illustrative STAMP-Releasing Formulations.

Illustrative, but non-limiting formulations of the STAMP-releasing dental varnish systems contemplated here are shown in Tables 9 and 10. These illustrative dental varnish systems comprise a first component that, in various embodiments, is provided as a dry powder containing one or more STAMP(s) and/or AMP(s) (e.g., C16G2) and a second component that provides a liquid varnish formulation. Combination of the first component with the second component provides a varnish formulation for application to the surface of a tooth.

Tables 9 illustrates various embodiments of the first component. As shown therein, the first component can comprise or consist of a STAMP (or AMP), a bulking agent (e.g., mannitol), and a buffer (e.g., His).

TABLE 9

Illustrative formulations for the first component of a two component dental varnish system.

| STAMP % in Final Dental Varnish*: | 1.4% | 2.6% | 4.9% |
|---|---|---|---|
| | Weight Percent in Freeze-Dried Powder (Component 1) | | |
| STAMP | 10.71% | 14.3% | 21.43% |
| HIS | 1.55% | 1.55% | 1.55% |
| Mannitol. | 83.54% | 79.96% | 72.82% |
| Sucralose | 4.20% | 4.20% | 4.20% |

*After combination with the second component (e.g. as shown in Table 12).

The first component can be formulated simply by mixing the components at room temperature until fully dissolved. The solution can, optionally be filtered. Then the solution can be lyophilized to form a dry powder.

Tables 10 shows one illustrative, but non-limiting embodiment of the second component. As illustrated therein, the second component can comprises or consist of a varnish (e.g., a (meth)acrylate and/or (meth)acrylamide varnish), a solvent (e.g., ethanol), and optionally a flavor agent, and/or sweetener.

TABLE 10

An illustrative formulation for the second component of a two component dental varnish system.

| Component | Amount (% w/w) |
|---|---|
| Solvent (e.g., ethanol) | 59.95% |
| Varnish (e.g., EUDRAGIT ® E) | 28.65% |
| Flavor (e.g. Watermelon Lavender Mint) | 11.39% |

The second component can be formulated simply by combining the various ingredients at room temperature and mixing until fully dissolved. The resulting varnish solution can be stored in a closed vessel at 4-8° C. or room temperature.

At the time and point of use the dental varnish can be reconstituted by simply combining the second component with the first component and mixing/shaking until the powder component is fully suspended and/or dissolved. The resulting varnish is then ready for reconstitution.

In one illustrative but non-limiting embodiment, 127 mg of the freeze-dried powder is combined with 1 mL of varnish solution. The resulting solution is mixed for about 10 seconds to 5 min, or from about 30 seconds to 2 min, or about 30 seconds and then is ready for application to the surface(s) of a tooth. The first component and second component can be mixed immediately to about 4 hours prior to use, or from immediately to about 2 hours before use, or from immediately to about 1 hour before use, or immediately before use.

Illustrative Fluoride-Releasing Formulations.

Illustrative, but non-limiting formulations of the fluoride-releasing dental varnish systems contemplated here are shown in Tables 11 and 12. These illustrative dental varnish systems comprise a first component that, in various embodiments, is provided as a dry powder containing a fluoride (fluoridizing agent) and a second component that provides a liquid varnish formulation. Combination of the first component with the second component provides a varnish formulation for application to the surface of a tooth.

Tables 11 illustrates various embodiments of the first component. As shown therein, the first component can comprise or consist of a fluoridizing agent (e.g., sodium fluoride), a bulking agent (e.g., mannitol), and a sweetener (e.g., sucralose).

TABLE 11

Illustrative formulations for the first component of a two component dental varnish system.

| Fluoride % in Final Dental Varnish*: | 0.50% | 1% | 2% | 2.50% | 5% |
|---|---|---|---|---|---|
| | Weight Percent in Freeze-Dried Powder (Component 1) | | | | |
| NaF | 3.94% | 7.87% | 15.75% | 19.69% | 39.37% |
| Mannitol | 94.66% | 90.73% | 82.85% | 78.91% | 59.23% |
| Sucralose | 1.40% | 1.40% | 1.40% | 1.40% | 1.40% |

*After combination with the second component (e.g. as shown in Table 12).

The first component can be formulated simply by mixing the components at room temperature until fully dissolved. The solution can, optionally be filtered. Then the solution is lyophilized or spray dried, followed by milling if required, to form a dry powder. The first component can also be formulated by making a dry blend of the components using common techniques for those skilled in the art.

Tables 12 shows one illustrative, but non-limiting embodiment of the second component. As illustrated therein, the second component can comprises or consist of a varnish (e.g., a (meth)acrylate and/or (meth)acrylamide varnish), a solvent (e.g., ethanol), and optionally a flavor agent.

TABLE 12

An illustrative formulation for the second component of a two component dental varnish system.

| Component | Amount (% w/w) |
|---|---|
| Solvent (e.g., ethanol) | 59.96% |
| Varnish (e.g., EUDRAGIT ® E) | 28.65% |
| Flavor (e.g., dinoberry) | 11.39% |

The second component can be formulated simply by combining the various ingredients at room temperature and mixing until fully dissolved. The resulting varnish solution can be stored in a closed vessel at 4-8° C. or room temperature.

At the time and point of use the dental varnish can be reconstituted by simply combining the second component with the first component and mixing/shaking until the powder component is fully suspended and/or dissolved. The resulting varnish is then ready for reconstitution.

In one illustrative but non-limiting embodiment, 127 mg of the freeze-dried powder is combined with 1 mL of varnish solution. The resulting solution is mixed for about 30 seconds and then is ready for application to the surface(s) of a tooth.

Combined Varnish Solution.

In various embodiments the dental varnishes contemplated herein can be provided as a two component system as described above. However, in other embodiments, the dental varnish is provided as a single component system, e.g. a single varnish solution containing the various ingredients as described above. Thus, for example, in certain embodiments, the fluoride dental varnish comprises a fluoride (e.g., NaF), a bulking agent (e.g., mannitol), a methacrylate and/or methacrylamide varnish (e.g., EUDRAGIT® varnish), a solvent (e.g., alcohol), and optionally a sweetener (e.g., sucralose, xylitol, etc.), and/or a flavoring agent.

An illustrative varnish composition is shown in Table 13. As indicated therein, a number of ingredients can be optional and the recited amounts will vary depending on the ingredients incorporated into a particular varnish.

TABLE 13

Illustrative dental fluoride varnish system.

| Ingredients | Weight % Range | Illustrative Formulation |
|---|---|---|
| Fluoride | 1-5 | 5 |
| Varnish | 12-35 | 25 |
| Bulking Agent | 6-30 | 7.5 |
| Solvent | 50-75 | 52.3 |
| Optional Ingredients Solvent | | |
| Sweetener | 0.5-1.5 | 0.2 |
| Flavor | 7-13 | 10 |
| Antiseptic | 0-5 | 0 |
| Antibiotic | 0-30 | 0 |
| Remineralization Agent | 0-20 | 0 |
| Tint | 0-0.1 | 0 |

In certain embodiments the varnish provides release of an effective amount of a fluoride and/or a STAMP (and/or AMP) for at least 1 hour after application, or for at least 2 hours after application, or for at least 4 hours after application, or for at least 6 hours after application, or for at least 8 hours after application, or for at least 12 hours after application, or for at least 24 hours after application, or for at least 48 hours after application.

In certain embodiments the formulation of the varnish comprises or consists of a formulation that would be produced by combining a first formulation comprising or consisting of the formulation shown in Table 11 with a second formulation comprising or consisting of the formulation shown in Table 12. In certain embodiments the formulation of the varnish comprises or consists of the formulation that would be produced by combining a first formulation comprising or consisting of the formulation shown in Table 11 with a second formulation comprising or consisting of the formulation shown in Table 12, where the combination ranges from about 50 mg, or from about 100 mg, or from about 125 mg, up to about 200 mg, or up to about 300 mg of the dry powder of the first component with 1 ml of the second component. In certain embodiments the formulation of the varnish comprises or consists of the formulation that would be produced by combining about 127 mg of the dry powder of a first formulation comprising or consisting of the formulation shown in Table 11 with about 1 mL of a second formulation comprising or consisting of the formulation shown in Table 12.

Methods of Use.

In various embodiments methods of use of the varnishes and/or varnish systems described herein are provided. Thus, for example, in certain embodiments a method improving tooth hardness, and/or inhibiting *S. mutans*, and/or reducing dental cavities in a mammal, is provided where the method involves applying to the surface of a tooth of the mammal a varnish as described herein, and permitting the varnish to form a dry film on said surface of a tooth.

In certain embodiments the method involves combining the first component of the varnish system (e.g., the powder component containing the fluoride agent) with the second component of the varnish system (e.g., a fluid component containing the varnish) to form the dental varnish ready for application. In certain embodiments the combining comprises combining from about 50 mg, or from about 100 mg, or from about 125 mg, up to about 200 mg, or up to about 250 mg of the dry powder of the first component with 1 ml of the second component or combining different amounts of the first and second component to produce the same proportions as these combinations.

In certain embodiments the combining comprises combining a first formulation comprising or consisting of the formulation shown in Table 11 with a second formulation comprising or consisting of the formulation shown in Table 12, where the combination ranges from about 50 mg, or from about 100 mg, or from about 125 mg, up to about 200 mg, or up to about 250 mg of the dry powder of the first component with 1 ml of the second component. In certain embodiments the combining comprises combining about 127 mg of the dry powder of a first formulation comprising or consisting of the formulation shown in Table 11 with about 1 mL of a second formulation comprising or consisting of the formulation shown in Table 12.

The resulting dental varnish is then applied to one or more surfaces of the teeth using methods known to those of skill in the art. For example, the varnish can readily be applied with a brush, a swab, a sponge, via spraying, and in certain embodiments via a dental tray or a mouthwash.

In various embodiments the subject is a non-human mammal. More typically however, the subject will be a human. In various embodiments the human is a human infant or child, an adolescent, an adult, and/or the elderly or infirm.

Illustrative Application Procedure.

Although it is typically not necessary to perform a professional prophylaxis prior to the application of the fluoride varnishes or STAMP-delivering varnishes described herein, in certain embodiments, the teeth are cleaned, e.g., with a toothbrush prior to application. Typically, although not necessarily in certain embodiments, the teeth are dried prior to application by wiping with a cotton gauze and/or by air drying. While drying may be preferred it is not absolutely necessary. Typically, the varnish will adhere even if the teeth are moist. If desired, the teeth can be isolated (e.g. with cotton rolls) to prevent recontamination with saliva. A small amount of the varnish is typically dispensed (e.g., 0.5 ml) and, in various embodiments, the entire dentition may be treated with as little as 0.3-0.6 ml. The varnish is applied with a brush or other means (e.g., as described above). In certain embodiments as a result of the time needed for frequent reloading of the brush/applicator, an alternative technique utilizing, for example, a plastic syringe (e.g., a 5 ml syringe) can be employed. This method allows an efficient application of the varnish which can be particularly useful in cases where speed is important, such as with a difficult pediatric patient. In certain embodiments the subject is instructed to avoid brushing for the rest of the day and normal oral hygiene procedures resume again the following day.

The varnish may be provided in individual dose systems and, in embodiments where the varnish system is utilized, the dose system may provide the first component and second component pre-measured in containers that can provide for rapid and easy combination and mixing of the components.

In certain embodiments, in order to improve efficacy in decay prevention, the varnish is reapplied quarterly, or at least twice yearly.

In certain embodiments the varnishes described herein can be provided in flow through applicators that can be applied to wet or dry teeth without leaving the mouth to re-load the brush or swab.

In various embodiments the dental varnishes and varnish systems described herein are indicated for use as a topical fluoride agent and/or anti-S. mutans agent on moderate and high-risk patients, especially children age 5 and younger. In various embodiments the varnishes and varnish systems can be used: 1) as desensitizing agents for exposed root surfaces, 2) as a fluoridated or anti-S. mutans (anti-caries) cavity varnish, 3) in circumstances where a high concentration of fluoride or STAMP is needed for high caries risk patients, 4) in the elderly to prevent increasingly prevalent root dentin lesions, which may require higher concentration of fluoride and/or STAMP, 5) on advanced enamel carious lesions, which may also require higher fluoride concentration for remineralization and/or STAMP compositions, 6) as a fluoride and/or STAMP treatment for institutionalized patients or in other situations where setting, equipment and patient management might preclude the use of other fluoride (or STAMP) delivery methods, 7) for caries prevention on exposed root surfaces, 8) for remineralization of lesions in root dentin, 9) for fluoride and/or STAMP application around orthodontic bands and brackets, and 10) as a fluoride or STAMP-treatment on patients when there is a concern that a fluoride or STAMP rinse, gel or foam might be swallowed.

Kits.

In various embodiments kits are provided for the delivery and use of the varnish systems and varnishes described herein. In certain illustrative, but non-limiting embodiments, the kit comprises a container containing a fluoride dental varnish or a STAMP- (or AMP-) delivering varnish as described herein, or the kit can contain a varnish system for a fluoride-delivering varnish or for a STAMP-delivering varnish as described herein. Where the kit provides a two-component system, the kit may comprise a first container containing the first component of the varnish system as described herein and a container containing the second component of the varnish system as described herein. In certain embodiments the first container and second container are provided as separate containers. In certain embodiments the first container and second container are separate chambers in a single container device (e.g., a dual barrel syringe, two blisters on a blister pack, etc.). In certain embodiments the kit further comprises an applicator (e.g., brush, a swab, a sponge, a sprayer, etc.) for application of the varnish to a tooth surface.

In addition, the kits can optionally include labeling and/or instructional materials providing directions (i.e., protocols) for the use of the varnish systems and/or varnishes described herein. Certain instructional materials describe how to combine the first component and second component of a varnish system using materials provided in the kit to produce the dental varnish. The instructional materials may also, optionally, teach preferred amounts, application methods, indications and counter indications, etc.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

EXAMPLE

The following example is offered to illustrate, but not to limit, the claimed invention.

Example 1

STAMP-Releasing Varnish

A novel varnish was formulated that enables rapid release of small and large molecules. The varnish sticks well to dried teeth at application, provides a smooth mouthfeel and lasts 4-6 hours. In certain embodiments the varnish is flavored. In certain illustrative embodiments the varnish comprises a formulation as illustrated in Table 14.

Figure 7:
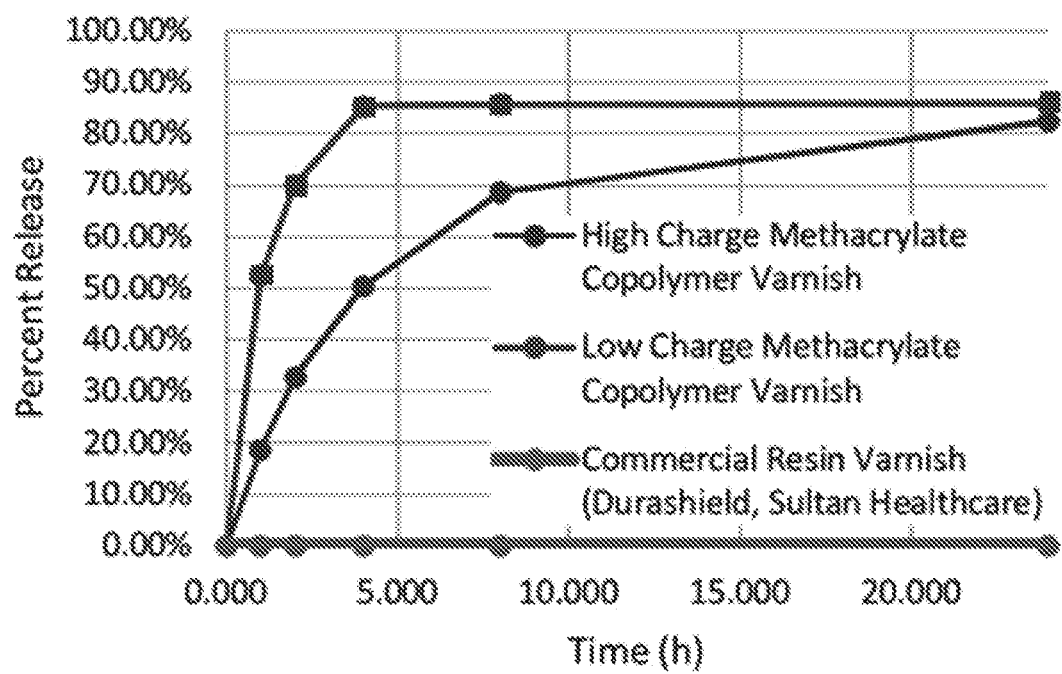
FIG. 7 shows a comparison of the release profiles of a targeted antimicrobial peptide (C16G2) from two varnish formulations (a high charge methacrylate and a low charge methacrylate) compared to a resin-based varnish.

FIG. 7 shows a comparison of the release profiles of a targeted antimicrobial peptide (C16G2) from two methacrylate copolymer varnish formulations with 33.3 mg/mL C16G2 (Eudragit RS PO "high charge", and Eudragit RL PO "low charge") compared to a shellac-based varnish with 50 mg/mL C16G2.

TABLE 14

Three illustrative targeted antimicrobial peptide releasing methacrylate polymer tooth varnishes, 15, 30 and 60 mg dose levels (in components and after reconstitution)

| Lyopowder: | | | |
| --- | --- | --- | --- |
| Sucralose | Targeted antimicrobial peptide (e.g., C16G2) | Mannitol | Histidine |
| 4.20% | 10.71 to 21.4% | 73-84% | 1.6% |

| Varnish Liquid: | | |
| --- | --- | --- |
| Ethanol | Methacrylate Polymer | Flavor |
| 60.00% | 28.60% | 11.40% |

| Examples of Dry Powder Formulation: | | | |
| --- | --- | --- | --- |
| Dose level: | 13.6 mg | 27.2 mg | 54.4 mg |
| C16G2 (targeted AMP) | 10.7% | 14.3% | 21.4% |
| Mannitol | 84% | 80% | 73% |
| Histidine | 1.6% | 1.6% | 1.6% |
| Surcalose | 4.2% | 4.2% | 4.2% |

TABLE 14-continued

Three illustrative targeted antimicrobial peptide releasing methacrylate polymer tooth varnishes, 15, 30 and 60 mg dose levels (in components and after reconstitution)

| mg FDP mixed with 1 ml second formulation solution | 127 mg | 190 mg | 254 mg |
|---|---|---|---|

FDP = Freeze-dried Powder

There was no release of C16G2 from the resin-based varnish over 48 hours at 20° C. or 37° C. Additionally, minimal C16G2 could be recovered by extraction and a large unknown peak seen in HPLC suggests a reaction between C16G2 and the Rosin/Shellac varnish. In contrast the three varnish formulations showed good release characteristics.

In various embodiments the varnishes containing the targeted antimicrobial peptide (e.g., C16G2) can also contain fluoride.

FIG. 1 illustrates the effect on a multispecies biofilm of a varnish formulation containing an antimicrobial peptide (C16G2).

Figure 2:
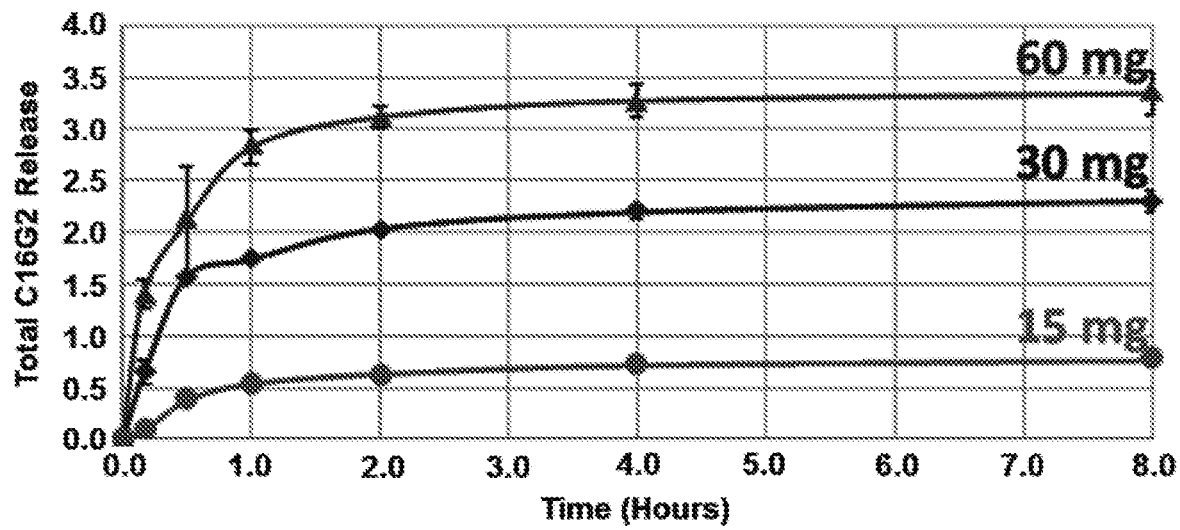
FIG. 2 illustrates the time course of release of a targeted antimicrobial (C16G2) peptide from a poly(meth)acrylate polymer varnish described herein at different peptide concentrations.

FIG. 2 illustrates the time course of release of a targeted antimicrobial (C16G2) peptide from a poly(meth)acrylate polymer varnish described herein at different peptide concentrations.

Example 2

C16G2 Varnish Formulation

In certain embodiments a C16G2 varnish drug product is manufactured for administration as a dental varnish product. This varnish product utilizes generally recognized as safe (GRAS) or compendia excipients. In certain embodiments, as noted above, the C16G2 varnish product is provided in two vials (e.g., glass vials), whose content is combined prior to application. In one illustrative, but non-limiting embodiment, one vial contains a powder blend of C16G2 at doses of 13.6, 27.2, and 54.4 mg and other required excipients. The other vial contains a vehicle solution. The qualitative and quantitative composition of several C16G2 varnish products is shown in Table 15, Table 16, and Table 17 below.

TABLE 15

Qualitative and quantitative composition of a 13.6 mg C16G2 varnish drug product.

| Component | Function | Amount per dose |
|---|---|---|
| C16G2 | Active (anti-S. mutans) agent | 13.60 mg |
| D-Mannitol, USP | Bulking agent | 105.92 mg |
| L-Histidine, USP | Buffer | 1.97 mg |
| Sucralose, NF | Flavoring Agent | 5.33 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1 |

NF = National Formulary, q.s. = quantity sufficient; USP = United States Pharmacopeia

TABLE 16

Qualitative and quantitative composition of a 27.2 mg C16G2 varnish drug product.

| Component | Function | Amount per dose |
|---|---|---|
| C16G2 | Drug Substance | 27.21 mg |
| D-Mannitol, USP | Bulking agent | 152.33 mg |
| L-Histidine, USP | Buffer | 2.95 mg |
| Sucralose, NF | Flavoring Agent | 8.00 mg |
| Ethanol, 200 proof, USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1 |

NF = National Formulary, q.s. = quantity sufficient; USP = United States Pharmacopeia

TABLE 17

Qualitative and quantitative composition of a 54.4 mg C16G2 varnish drug product.

| Component | Function | Amount per dose |
|---|---|---|
| C16G2 | Drug Substance | 54.43 mg |
| D-Mannitol, USP | Bulking agent | 184.97 mg |
| L-Histidine, USP | Buffer | 3.94 mg |
| Sucralose, NF | Flavoring Agent | 10.67 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide NF | In process pH, adjustment | q.s. to pH 6.0 ± 0.1 |

NF = National Formulary, q.s. = quantity sufficient; USP = United States Pharmacopeia Placebo Varnish Formulation In certain embodiments for evaluation purposes a placebo varnish is formulated. Typically the placebo varnish utilizes GRAS or compendia excipients. To maintain a study blind, the Placebo product can also be provided in two vials, whose content is combined prior to application. One vial contains a powder blend of the same excipients as the active vial but without C16G2. The other vial contains a vehicle solution. Placebo products also have a similar qualitative and quantitative composition as shown in Table 15, but do not contain C16G2 drug substance and the omitted weight of the active product is compensated for with additional mannitol or other bulking material.

The foregoing varnish formulations are illustrative and not limiting. Using the teachings provided herein numerous other STAMP-releasing varnish formulations will be available to one of skill in the art.

Example 3

Evaluation of Fluoride Varnish System

A varnish system designated C3, was evaluated for its fluoride-release properties. The C3 system comprises a fluoride powder with a bulking agent suspended in a solution of methacrylate polymer dissolved in ethanol.

Figure 3:
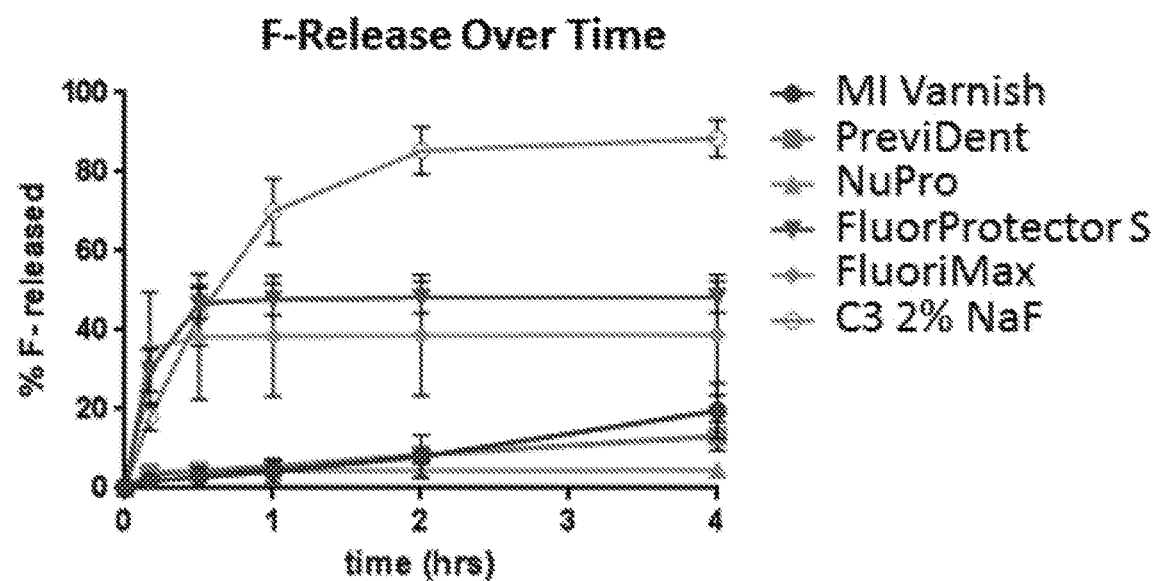
FIG. 3 shows the release of fluoride from various varnishes over time.
Figure 4:
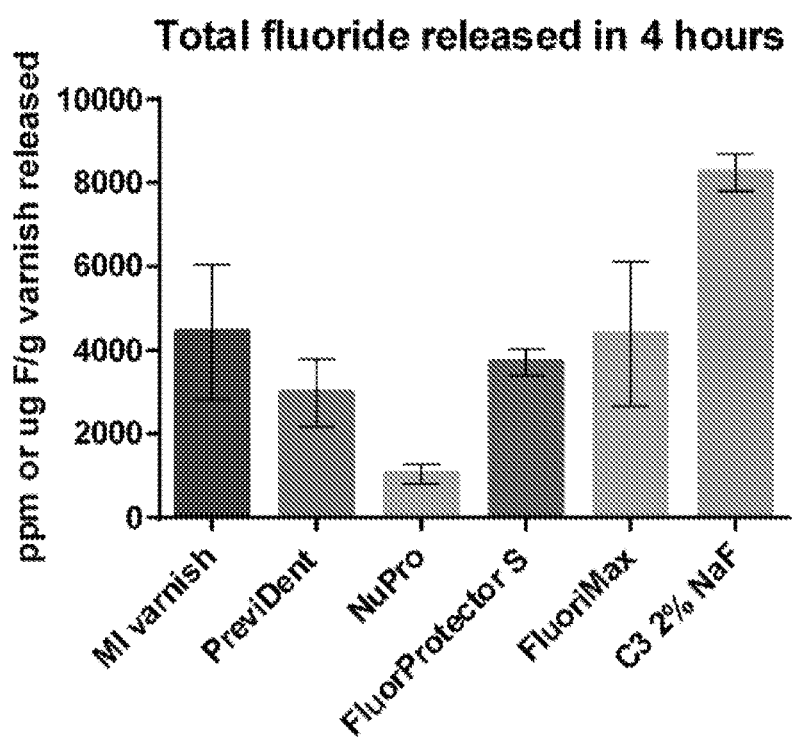
FIG. 4 shows the total fluoride released in four hours from various varnishes.

FIG. 3 shows the fluoride release over time from our methacrylate-based polymer varnish (designated C3) as compared to fluoride release from other varnishes. The C3 varnish provided significantly greater fluoride release over time. FIG. 4 shows the total fluoride release from our methacrylate-based polymer varnish (designated C3) as compared to total fluoride release from other varnishes. The C3 varnish provided significantly greater total fluoride release.

Figure 5A:
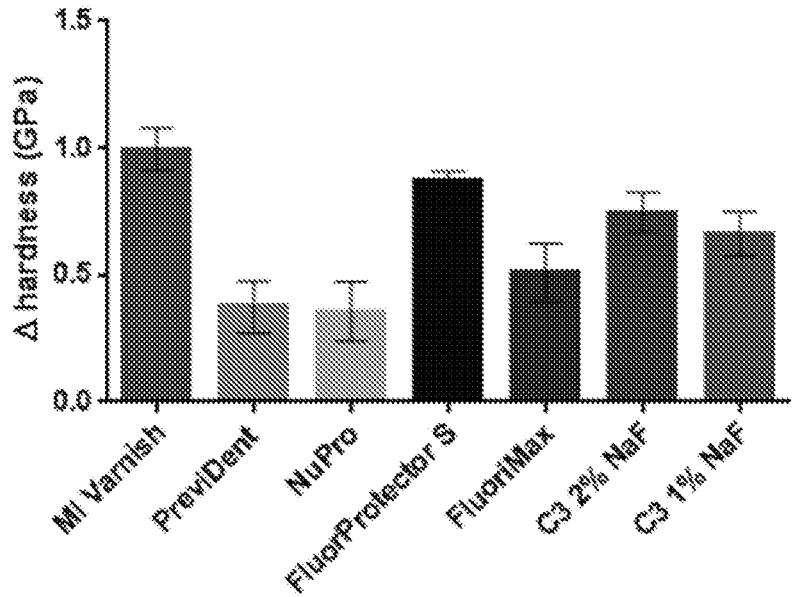
FIGS. 5A and 5B show the improvement in hardness after varnish treatment with various varnishes.
Figure 5B:
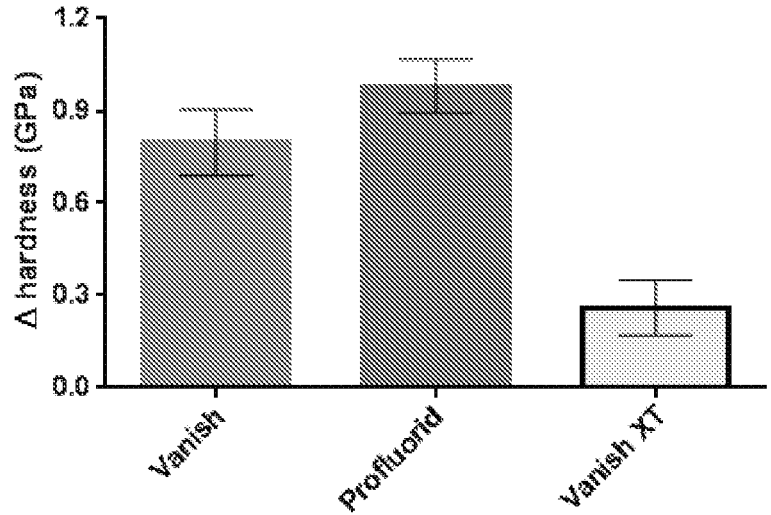
Figure 6:
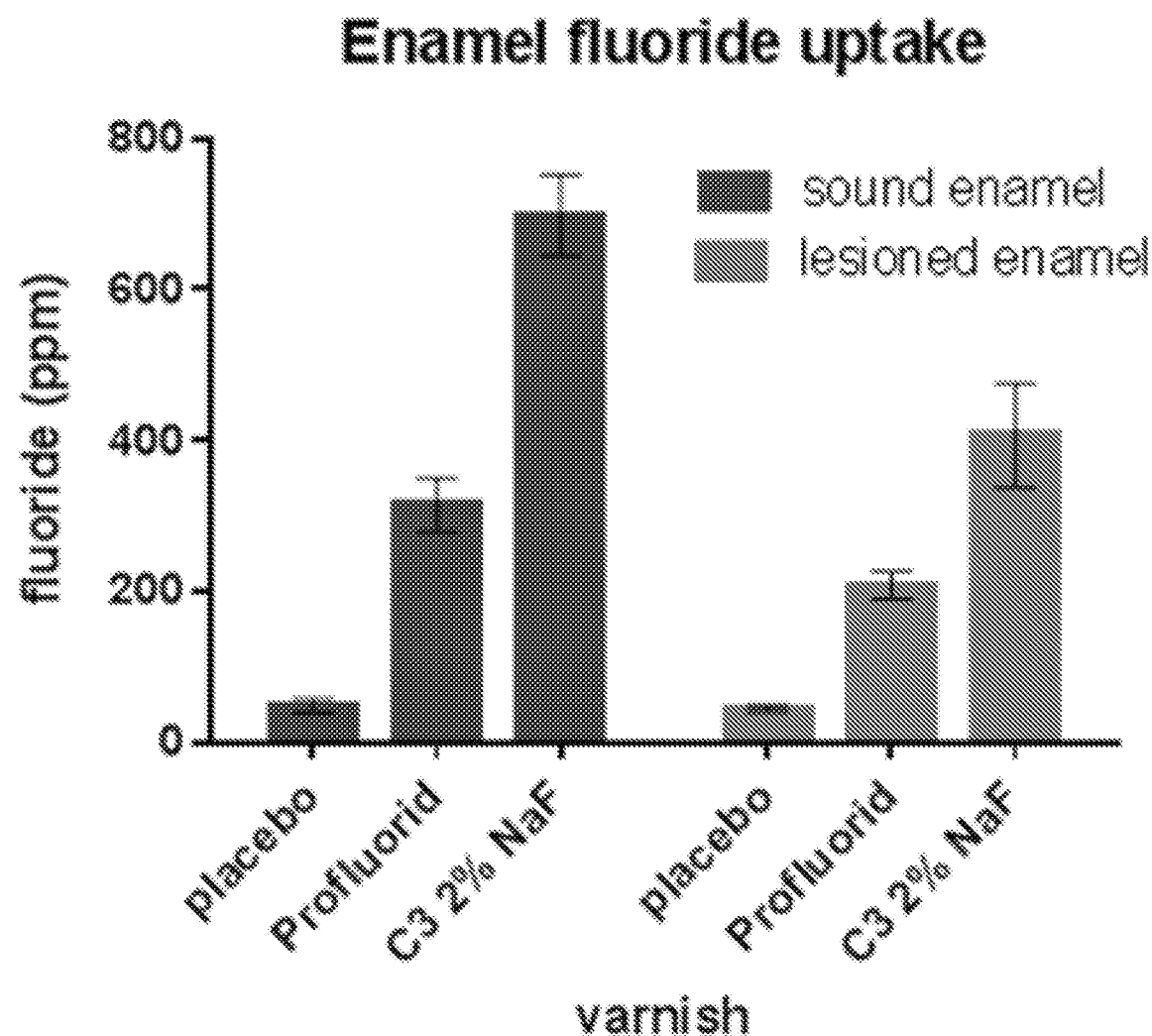
FIG. 6 shows the uptake of fluoride from varnish into sound enamel after 4 hours at the site of varnish application and the uptake of fluoride into lesioned enamel adjacent to the site of varnish application.

FIGS. 5A and 5B show the hardness improvement produced by treatment with the C3 varnish compared to other commercial products. The C3 varnish produced a hardness improvement comparable to or better than various commercial products. FIG. 6 shows the uptake of fluoride from varnish into sound enamel after 4 hours at the site of varnish application and the uptake of fluoride into lesioned enamel adjacent to the site of varnish application. In both cases, the C3 varnish allows significantly more fluoride uptake than a commercial product.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A dental varnish system for the sustained delivery of a specifically targeted antimicrobial peptide (STAMP), said varnish system comprising:
   a first component that is a dry powder, said first component comprising a specifically targeted antimicrobial peptide (STAMP) comprising the amino acid sequence TFFRLFNRSFTQAL GKGGGKNLRIIRKGIHIIKKY (C16G2, SEQ ID NO:1); and
   a second component that is a fluid, said second component comprising a varnish solution wherein said solution comprises an aminomethacrylate polymer and ethanol 200 proof USP;
   where combination of said first component with said second component provides a fluid varnish formulation in which said ethanol is a solvent for said dry powder first component, where said formulation when applied to the surface of a tooth delivers an effective amount of said STAMP that retains antimicrobial activity to said surface of said tooth for at least 4 hours after application.

2. The varnish system of claim 1, wherein:
   said varnish formulation provides release of an effective amount of said STAMP for at least 6 hours after application, or for at least 8 hours after application, or for at least 12 hours after application, or for at least 24 hours after application, or for at least 48 hours after application; and/or
   said varnish formulation provides a release of at least 80% of said STAMP or AMP within about 8 hours or less, or within about 6 hours or less, or within about 4 hours or less, or within about 2 hours or less, or within about 1 hour or less.

3. The varnish system of claim 1, wherein said first component comprises said STAMP and a pH adjuster.

4. The varnish system of claim 1, wherein:
   combination of said first component with said second component in substantially equal parts as fluid, or where the first component is a dry powder in a ratio of powder to fluid second component ranging from about 100 mg powder up to about 260 mg powder mixed with 1 ml fluid second component produces a formulation having a pH ranging from about 5.0 to about 7.5, or from about 5.9 to about 6.1, and containing said STAMP or AMP in a form and concentration that is effective to kill *S. mutans*; or
   said first component is a dry powder in a ratio of powder to fluid second component of about 127 mg dry powder to 1 ml fluid second component; or
   said first component is a dry powder in a ratio of powder to fluid second component of about 190 mg dry powder to 1 ml fluid second component; or
   said first component is a dry powder in a ratio of powder to fluid second component of about 254 mg dry powder to 1 ml fluid second component; or
   said first component contains only said specifically targeted antimicrobial peptide; or
   first component contains only said specifically targeted antimicrobial peptide, and a thickener; or
   said first component contains only said specifically targeted antimicrobial peptide and a preservative; or
   said first component contains only said specifically targeted antimicrobial peptide, a thickener, and a preservative; and/or wherein:
   the second component comprises a buffer; and/or
   said first component or the second component further comprises a salt to adjust tonicity; and/or said first component or said second component further comprises a bulking agent; and/or said first component or said second component further comprises one or more solubilizing/emulsifying agents; and/or said first component or said second component further comprises a chelating agent; and/or said first component or said second component further comprises a preservative; and/or said first component or said second component further comprises a sweetener; and/or said first component or said second component further comprises a colorant; and/or said first component or said second component further comprises flavoring agent; and/or said first component and/or said second component further comprises a thickener; and/or said second component comprises a cationic (positively charged, permanently or pH dependent) random co-polymer based on dimethylaminoethyl methacrylate; and/or said second component comprises Poly(butyl methacrylate-co-(2-dimethylaminoehtyl) methacrylate-co-methyl methacrylate) at 1:2:1 mol ratio.

5. The varnish system of claim 1, wherein:

said second component comprises about 28.6 varnish polymer, about 60% ethanol, and about 11.4% flavor; and/or said first component comprises a powder comprising about 10.7% antimicrobial peptide, about 84% Mannitol, about 1.6% Histidine, about 4.2% sucralose and said first component is combined with the second component in a ratio of about 127 mg dry powder to 1 ml of said second component (varnish solution); or said first component comprises a powder comprising about 14.3% antimicrobial peptide, about 80% Mannitol, about 1.6% histidine, about 4.2% sucralose; and said first component is combined with the second component in a ratio of about 190 mg dry powder to 1 ml of said second component (varnish solution); or said first component comprises a powder comprising about 21.4% antimicrobial peptide, about 73% mannitol, about 1.6% histidine, about 4.2% sucralose; and said first component is combined with the second component in a ratio of about 254 mg dry powder to 1 ml of said second component (varnish solution); or said second component comprises poly(butyl methacrylate-co-(2-dimethylaminoehtyl) methacrylate-co-methyl methacrylate at 1:2:1 mol ratio and about 11.4% flavor in 60% ethanol.

6. The varnish system of claim 1, wherein:

when said first component is combined with said second component said system forms a varnish comprising:
  a specifically targeted antimicrobial peptide;
  D-mannitol;
  L-histidine;
  Amino Methacrylate Copolymer; and
  ethanol; or wherein combination of said first component with said second component provides a varnish formulation selected from the group consisting of:

| Component | Function | Amount per dose |
|---|---|---|
| C16G2 STAMP | Active (anti-S. mutans) agent | 13.60 mg |
| D-Mannitol, USP | Bulking agent | 105.92 mg |
| L-Histidine, USP | Buffer | 1.97 mg |
| Sucralose, NF | Flavoring Agent | 5.33 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1, |

NF = National Formulary,
q.s. = quantity sufficient;
USP = United States Pharmacopeia and

| Component | Function | Amount per dose |
|---|---|---|
| C16G2 STAMP | Active Agent | 27.21 mg |
| D-Mannitol, USP | Bulking agent | 152.33 mg |
| L-Histidine, USP | Buffer | 2.95 mg |
| Sucralose, NF | Flavoring Agent | 8.00 mg |
| Ethanol, 200 proof, USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1, | and

| Component | Function | Amount per dose |
|---|---|---|
| C16G2STAMP | Active Agent | 54.43 mg |
| D-Mannitol, USP | Bulking agent | 184.97 mg |
| L-Histidine, USP | Buffer | 3.94 mg |
| Sucralose, NF | Flavoring Agent | 10.67 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1. |

7. The varnish system of claim 1, wherein said first component and/or said second component further comprises a fluoride.

8. A dental varnish for the sustained delivery of a specifically targeted antimicrobial peptide (STAMP), said varnish comprising:

a specifically targeted antimicrobial peptide (STAMP) comprising the amino acid sequence TFFRLFNRSFTQAL GKGGGKNLRIIRKGIHIIKKY (C16G2, SEQ ID NO:1); and a varnish solution comprising an aminomethacrylate polymer and ethanol 200 proof USP;

where said dental varnish provides a fluid varnish formulation in which said ethanol is a solvent for said specifically targeted antimicrobial peptide, where said formulation when applied to the surface of a tooth delivers a tooth and delivery of an effective amount of said STAMP that retains antimicrobial activity to said surface of said tooth for at least 4 hours after application.

9. The varnish of claim 8, wherein:

said varnish provides release of an effective amount of said STAMP for at least 6 hours after application, or for at least 8 hours after application, or for at least 12 hours after application, or for at least 24 hours after application, or for at least 48 hours after application; and/or said varnish formulation provides a release of at least 80% of said STAMP within about 8 hours or less, or within about 6 hours or less, or within about 4 hours or less, or within about 2 hours or less, or within about 1 hour or less.

10. The varnish of claim 8, wherein:

said varnish solution comprises a cationic (positively charged, permanently or pH dependent) random copolymer based on dimethylaminoethyl methacrylate; or said varnish solution comprises Poly(butyl methacrylate-co-(2-dimethylaminoehtyl) methacrylate-co-methyl methacrylate) at 1:2:1 mol ratio.

11. The varnish of claim 8, wherein said varnish comprises one or more agents selected from the group consisting of a bulking agent, a buffer, a flavoring agent, a solvent, an emulsifying agent, a chelating agent, a coloring agent, a sweetener, and an in process pH adjustor.

12. The varnish of claim 8, wherein said varnish comprises:

- a specifically targeted antimicrobial peptide;
- D-mannitol;
- L-histidine;
- Amino Methacrylate Copolymer; and
- ethanol; or said varnish comprises a formulation selected from the group consisting of:

| Component | Function | Amount per dose |
|---|---|---|
| C16G2 STAMP | Active (anti-S. mutans) agent | 13.60 mg |
| D-Mannitol, USP | Bulking agent | 105.92 mg |
| L-Histidine, USP | Buffer | 1.97 mg |
| Sucralose, NF | Flavoring Agent | 5.33 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1, |

NF = National Formulary,
q.s. = quantity sufficient;
USP = United States Pharmacopeia and

| Component | Function | Amount per dose |
|---|---|---|
| C16G2 STAMP | Active Agent | 27.21 mg |
| D-Mannitol, USP | Bulking agent | 152.33 mg |
| L-Histidine, USP | Buffer | 2.95 mg |
| Sucralose, NF | Flavoring Agent | 8.00 mg |
| Ethanol, 200 proof, USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1, | and

| Component | Function | Amount per dose |
|---|---|---|
| C16G2 STAMP | Active Agent | 54.43 mg |
| D-Mannitol, USP | Bulking agent | 184.97 mg |
| L-Histidine, USP | Buffer | 3.94 mg |
| Sucralose, NF | Flavoring Agent | 10.67 mg |
| Ethanol, 200 proof USP | Solvent | 521.57 mg |
| Watermelon, Lavender, Mint Flavor | Flavoring agent | 99.09 mg |
| Amino Methacrylate Copolymer, USP | Polymer | 249.26 mg |
| FD&C Blue No. 1 | Coloring Agent | 0.09 mg |
| Sodium Hydroxide, NF | In process pH adjustment | q.s. to pH 6.0 ± 0.1. |

13. The varnish of claim 8, wherein said first formulation and/or said dental varnish further comprises a fluoride.

14. A dental varnish kit, said kit comprising:

a container containing dental varnish according to claim 8.

15. A kit for providing a dental varnish system of claim 1, said kit comprising:

a container containing said first component; and
a second container containing said second component.

* * * * *